US011263793B2

(12) United States Patent
Schieke et al.

(10) Patent No.: US 11,263,793 B2
(45) Date of Patent: *Mar. 1, 2022

(54) METHOD AND SYSTEM FOR ASSESSING IMAGES USING BIOMARKERS

(71) Applicants: Moira F. Schieke, Madison, WI (US); Erica Lin, Cambridge, MA (US)

(72) Inventors: Moira F. Schieke, Madison, WI (US); Erica Lin, Cambridge, MA (US)

(73) Assignee: Moira F. Schieke, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,514

(22) Filed: Jul. 8, 2019

(65) Prior Publication Data

US 2020/0167976 A1 May 28, 2020

Related U.S. Application Data

(63) Continuation of application No. 15/925,082, filed on Mar. 19, 2018, now Pat. No. 10,347,015, which is a (Continued)

(51) Int. Cl.
*G06T 11/00* (2006.01)
*G06T 7/00* (2017.01)
(Continued)

(52) U.S. Cl.
CPC .......... *G06T 11/008* (2013.01); *A61B 5/0091* (2013.01); *A61B 5/7275* (2013.01);
(Continued)

(58) Field of Classification Search
CPC combination set(s) only.
See application file for complete search history.

(56) References Cited

U.S. PATENT DOCUMENTS 6,123,647 A 9/2000 Mitchell
6,567,684 B1 5/2003 Chenevert et al.
(Continued)

FOREIGN PATENT DOCUMENTS

EP 3 043 318 7/2016
EP 3 117 771 A2 1/2017
(Continued)

OTHER PUBLICATIONS

Non-Final Office Action on U.S. Appl. No. 14/821,700 dated Apr. 28, 2020.
(Continued)

*Primary Examiner* — Tahmina N Ansari
(74) *Attorney, Agent, or Firm* — Foley & Lardner LLP

(57) ABSTRACT

A method of forming a probability map is disclosed. According to one embodiment, a method may include: (1) obtaining multiple measures of multiple imaging parameters for every stop of a moving window on an image, wherein two neighboring ones of the stops of the moving window are partially overlapped with each other; (2) obtaining first probabilities of an event for the stops of the moving window by matching the measures of the imaging parameters to a classifier; and (3) obtaining second probabilities of the event for multiple voxels of a probability map based on information associated with the first probabilities.

20 Claims, 75 Drawing Sheets

Related U.S. Application Data continuation of application No. 14/821,703, filed on Aug. 8, 2015, now Pat. No. 9,922,433.

(60) Provisional application No. 62/167,940, filed on May 29, 2015.

(51) Int. Cl.

| | | |
|---|---|---|
| *A61B 5/00* | (2006.01) | |
| *G06K 9/62* | (2022.01) | |
| *G16H 50/30* | (2018.01) | |
| *G16H 30/40* | (2018.01) | |
| *A61B 5/055* | (2006.01) | |
| *A61B 6/03* | (2006.01) | |

(52) U.S. Cl.
CPC ......... *G06K 9/6278* (2013.01); *G06K 9/6281* (2013.01); *G06T 7/0012* (2013.01); *G16H 30/40* (2018.01); *G16H 50/30* (2018.01); *A61B 5/0075* (2013.01); *A61B 5/055* (2013.01); *A61B 6/032* (2013.01); *A61B 6/037* (2013.01); *A61B 2576/02* (2013.01); *G06K 2209/053* (2013.01); *G06T 2207/10081* (2013.01); *G06T 2207/10088* (2013.01); *G06T 2207/10104* (2013.01); *G06T 2207/10108* (2013.01); *G06T 2207/20076* (2013.01); *G06T 2207/30068* (2013.01); *G06T 2207/30081* (2013.01); *G06T 2207/30096* (2013.01)

(56) References Cited

U.S. PATENT DOCUMENTS

| | | | |
|---|---|---|---|
| 6,956,373 | B1 | 10/2005 | Brown et al. |
| 8,509,570 | B2 | 8/2013 | Degani et al. |
| 8,605,980 | B2 | 12/2013 | Li et al. |
| 8,768,431 | B2 | 7/2014 | Ross et al. |
| 8,781,214 | B2 | 7/2014 | Davis et al. |
| 8,805,619 | B2 | 8/2014 | Sorensen et al. |
| 8,818,484 | B2 | 8/2014 | Liew et al. |
| 8,873,836 | B1 | 10/2014 | Dietrich et al. |
| 9,092,691 | B1 | 7/2015 | Beaumont et al. |
| 9,165,362 | B2 | 10/2015 | Siewerdsen et al. |
| 9,424,639 | B2 | 8/2016 | Jacob |
| 9,615,028 | B2 | 4/2017 | Mizutani et al. |
| 2002/0186818 | A1 | 12/2002 | Arnaud et al. |
| 2002/0193677 | A1 | 12/2002 | Thornton |
| 2003/0072479 | A1 | 4/2003 | Sofia Totterman et al. |
| 2006/0269476 | A1 | 11/2006 | Kuo |
| 2008/0097186 | A1 | 4/2008 | Biglieri et al. |
| 2009/0161928 | A1* | 6/2009 | Khamene .............. G06T 7/0012 382/128 |
| 2009/0208075 | A1 | 8/2009 | Fischer et al. |
| 2010/0158332 | A1 | 6/2010 | Rico et al. |
| 2010/0284927 | A1 | 11/2010 | Lu et al. |
| 2011/0243417 | A1* | 10/2011 | Madabhushi ........ G06K 9/3233 382/131 |
| 2011/0312520 | A1 | 12/2011 | Kennedy et al. |
| 2013/0004044 | A1 | 1/2013 | Ross et al. |
| 2013/0197349 | A1 | 8/2013 | Blumhagen et al. |
| 2013/0329973 | A1 | 12/2013 | Cao et al. |
| 2014/0003697 | A1 | 1/2014 | Qian et al. |
| 2014/0010429 | A1 | 1/2014 | Highnam et al. |
| 2014/0010430 | A1 | 1/2014 | Chandelier et al. |
| 2014/0037172 | A1 | 2/2014 | Madabhushi et al. |
| 2014/0064580 | A1 | 3/2014 | Madabhushi et al. |
| 2014/0079302 | A1 | 3/2014 | Sato et al. |
| 2014/0086836 | A1 | 3/2014 | Burnham et al. |
| 2014/0101080 | A1 | 4/2014 | Lee et al. |
| 2014/0126794 | A1 | 5/2014 | Ahn et al. |
| 2014/0153795 | A1 | 6/2014 | Lenox |
| 2014/0185888 | A1 | 7/2014 | Kelm et al. |
| 2014/0185900 | A1 | 7/2014 | Lee et al. |
| 2014/0195472 | A1 | 7/2014 | Kawagishi |
| 2014/0205163 | A1 | 7/2014 | Stark et al. |
| 2014/0219535 | A1 | 8/2014 | Chen et al. |
| 2014/0228667 | A1 | 8/2014 | Dankerl et al. |
| 2014/0233826 | A1 | 8/2014 | Agaian et al. |
| 2014/0241606 | A1 | 8/2014 | Park et al. |
| 2014/0309511 | A1* | 10/2014 | Stal ...................... A61B 5/7267 600/365 |
| 2015/0003706 | A1 | 1/2015 | Eftestol et al. |
| 2015/0093007 | A1 | 4/2015 | Beaumont et al. |
| 2015/0198688 | A1 | 7/2015 | Cetingul |
| 2015/0352363 | A1 | 12/2015 | McIntyre et al. |
| 2016/0019693 | A1 | 1/2016 | Silbersweig et al. |
| 2016/0038095 | A1 | 2/2016 | Schieke |
| 2016/0086326 | A1 | 3/2016 | Raschke et al. |
| 2016/0117816 | A1 | 4/2016 | Taylor |
| 2016/0217576 | A1 | 7/2016 | Kabus et al. |
| 2016/0292194 | A1 | 10/2016 | Farkash |
| 2016/0350933 | A1 | 12/2016 | Schieke |
| 2016/0350946 | A1* | 12/2016 | Schieke ................ G16H 30/40 |
| 2017/0046839 | A1 | 2/2017 | Paik et al. |
| 2017/0261584 | A1 | 9/2017 | James et al. |
| 2017/0263023 | A1 | 9/2017 | Zhou |
| 2018/0114312 | A1 | 4/2018 | Palma |
| 2020/0281539 | A1 | 9/2020 | Hoernig et al. |

FOREIGN PATENT DOCUMENTS

| | | |
|---|---|---|
| WO | WO-2015/175746 A1 | 11/2015 |
| WO | WO-2016/206942 A1 | 12/2016 |

OTHER PUBLICATIONS

Notice of Allowance on U.S. Appl. No. 15/640,107 dated Mar. 10, 2020.

"Determining Single Voxel Value from Larger Region of Interest (ROI)," Dec. 18, 2014, 21 pages.

Antipolis, "MEDIAN Technologies strengthens IP portfolio with US patent," MEDIAN Technologies (ALMDT), Sep. 10, 2015, 4 pages.

Ashraf, et al., "Identification of Intrinsic Imaging Phenotypes for Breast Cancer Tumors: Preliminary Associations with Gene Expression Profiles," Radiology, Aug. 2014, pp. 374-384, vol. 272, No. 2.

Baselga, et al., "Everolimus in Postmenopausal Hormone-Receptor 2013 Positive Advanced Breast Cancer," New England Journal of Medicine, Feb. 9, 2012, pp. 520-529, vol. 366, No. 6.

Boes, et al., "Image Registration for Quantitative Parametric Response Mapping of Cancer Treatment Response," Translational Oncology, Feb. 2014, pp. 101-110, vol. 7, No. 1.

Bornn, et al., "Herded Gibbs Sampling," Mar. 16, 2013, 21 pages.

Buckley,"Uncertainty in the Analysis of Tracer Kinetics Using Dynamic Contrast-Enhanced T1-Weighted MRI," Magnetic Resonance in Medicine, Feb. 20, 2002, pp. 601-606, vol. 47.

Chan, et al., "Detection of Prostate Cancer by Integration of Line-Scan Diffusion, T2-Mapping and T2-Weighted Magnetic Resonance Imagine; a Multichannel Statistical Classifier," Medical Physics, Sep. 2003, pp. 2390-2398, vol. 30, No. 9.

Colen, et al., "NCI Workshop Report: Clinical and Computational Requirements for Correlating Imaging Phenotypes with Genomics Signatures," Translational Oncology, Oct. 2014, pp. 565-569, vol. 7, No. 5.

Ellingson, et al., "Volumetric Analysis of Functional Diffusion Maps is a Predictive Imaging Biomarker for Cytotoxic and Anti-Angiogenic Treatments in Malignant Gliomas," Journal of Neuro-Oncology, Mar. 2011, pp. 95-103, vol. 102, Issue 1.

Ellingson, et al.,"Graded Functional Diffusion Map 2013 Defined Characteristics of Apparent Diffusion Coefficients Predict Overall Survival in Recurrent Glioblastoma Treated with Bevacizumab," Neuro-Oncology, Oct. 2011, pp. 1151-1161, vol. 13, No. 10.

Final Office Action on U.S. Appl. No. 14/821,700 dated Mar. 18, 2019.

Galavis, et al.,"Variability of Textural Features in FDG PET Images Due to Different Acquisition Modes and Reconstruction Parameters," Acta Oncologica, Sep. 2010, pp. 1012-1016, vol. 49, Issue 7.

(56) References Cited

OTHER PUBLICATIONS

Galban, et al., "The Parametric Response Map: An Imaging Biomarker for Early Cancer Treatment Outcome," Nature Medicine, 2009, pp. 572-576, vol. 15, No. 5.
Galbraith, et al., Reproducibility of Dynamic Contrast-Enhanced MRI in Human Muscle and Tumours: Comparison of Quantitative and Semi-Quantitative Analysis, NMR in Biomedicine, Apr. 2002, pp. 132-142, vol. 15, Issue 2.
Gillies, et al., "MRI of the Tumor Microenvironment," Journal of Magnetic Resonance Imaging, Oct. 2002, pp. 430-450, vol. 16, Issue 4.
Haq, et al., "A Data-Driven Approach to Prostate Cancer Detection From Dynamic Contrast Enhanced MRI," Computerized Medical Imaging and Graphics, Apr. 2015, pp. 37-45, vol. 41.
International Preliminary Report on Patentability in International Application No. PCT/US2017/040456 dated Jan. 10, 2019 (10 pages).
International Search Report and Written Opinion in International Application No. PCT/US2017/040456 dated Oct. 19, 2017 (14 pages).
International Search Report and Written Opinion in PCT/US2018/028679 dated Jan. 29, 2019 (14 pages).
Irani, et al., "Motion Analysis for Image Enhancement: Resolution Occlusion, and Transparency," Journal of Visual Communication and Image Representation, Dec. 1993, pp. 324-335, vol. 4, No. 4.
Kwak, et al., "Automated Prostate Cancer Detection Using T2-Weighted and High-B-Value Diffusion-Weighted Magnetic Resonance Imaging," The International Journal of Medical Physics Research and Practice, May 2015, pp. 2368-2378, vol. 42, Issue 5.
Kwak, et ai., "correlation or Magnetic Resonance Imaging With Digital Histopathology in Prostate," International Journal of Computer Assisted Radiology and Surgery, Apr. 2016, pp. 657-666, vol. 11, Issue 4.
Kwak, et al., "Prostate Cancer: A Correlative Study of Multiparametric MR Imaging and Digital Histopathology," Radiology, Oct. 2017, pp. 1-10, vol. 285, Issue 1.
Langer, et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, Aug. 2009, pp. 327-334, vol. 30, Issue 2.
Lee, et al., "Maximum Entropy and Bayesian Methods," Kluwer Academic Publishers, 1993, 414 pages.
Li, et al., "Cell Membrane Water Exchange Effects in Prostate DCE-MRI," Journal of Magnetic Resonance, May 2012, pp. 77-85, vol. 218.
Maani, et al., "Voxel-Based Texture Analysis of the Brain," Plos One, Mar. 10, 2015, pp. 1-19.
Maenpaa, et al., "Texture Analysis With Local Binary Patterns," WSPC, May 13, 2004, pp. 1-20, vol. 8, Issue 19.
Method for Determining in Vivo Tissue Biomarker Characteristics Using Multiparameter MRI Matrix Creation and Big Data Analytics (Draft application), 22 pages.
Moffat, et al., "Functional Diffusion Map: A Noninvasive MRI Biomarker for Early Stratification of Clinical Brain Tumor Response," Proceedings of the National Academy of Sciences, Apr. 2005, pp. 5524-5529, vol. 102, Issue 15.
Moradi, et al., "Multiparametric MRI Maps for Detection and Grading of Dominant Prostate Tumors," Journal of Magnetic Resonance Imaging, Jun. 2012, pp. 1403-1413 Vol. 35, Issue 6.
Nasrollahi, et al., "Super-resolution: A Comprehensive survey," Machine Vision & Applications, Aug. 2014, pp. 1423-1468, vol. 25, Issue 6.
Niaf, et al., "Computer-Aided Diagnosis of Prostate Cancer in the Peripheral Zone Using Multiparametric MRI," Physics in Medicine Biology, May 2012, pp. 3833-3851, vol. 57, No. 12.
Non-Final Office Action on U.S. Appl. No. 15/640,107 dated Jan. 23, 2019.
Non-Final Office Action on U.S. Appl. No. 15/925,082 dated Jul. 24, 2018.
Non-Final Rejection Office Action in U.S. Appl. No. 14/821,703 dated Mar. 22, 2017 (56 pages).
Non-Final Rejection Office Action on U.S. Appl. No. 15/165,644 dated Nov. 30, 2017 (40 pages).
Oto, et al., "Diffusion-Weighted and Dynamic Contrast-Enhanced MRI of Prostate Cancer: Correlation of Quantitative MR Parameters With Gleason Score and Tumor Angiogenesis," American Journal of Roentgenology, Dec. 2011, pp. 1382-1390, vol. 197, No. 6.
Padhani, et al., "Reproducibility of Quantitative Dynamic MRI of Normal Human Tissues," NMR in Biomedicine, Apr. 2002, pp. 143-153, vol. 15, Issue 2.
Peng, et al., "Quantitative Analysis of Multiparametric Prostate MR Images: Differentiation Between Prostate Cancer and Normal Tissue and Correlation with Gleason Score—A Computer-aided Diagnosis Developmental Study," Radiology, Jun. 2013, pp. 787-796, vol. 267, No. 3.
Purysko, et al., "Li-Rads: A Case-based Review of the New Categorization of Liver Findings in Patients With End-Stage Liver Disease," RadioGraphics, November-Dec. 2012, pp. 1977-2012, vol. 32, Issue 7.
Rijpkema, et al., "Method for Quantitative Mapping of Dynamic MRI Contrast Agent Uptake in Human Tumors," Journal of Magnetic Resonance Imaging, Oct. 2001, pp. 457-463, vol. 14, Issue 4.
Roberts, et al., "The Effect of Blood Inflow and B1 -Field Inhomogeneity on Measurement of the Arterial Input Function in Axial3D Spoiled Gradient Echo Dynamic Contrast-Enhanced MRI," Magnetic Resonance in Medicine, Jan. 2010, pp. 108-119, vol. 65, Issue 1.
Senseney, et al., "Tumor Treatment Response Identification Using Combination Post-Treatment Mapping to Quantify Voxel-Wise Multiparameter MRI Biomarker Changes: A Simulation Study," International Symposium on Biomedical Imaging, May 2012, Barcelona, Spain.
Shah, et al., "Decision Support System for Localizing Prostate Cancer based on Multiparametric Magnetic Resonance Imaging," Medical Physics, Jul. 2012, pp. 4093-4103, vol. 39, No. 7.
US Office Action on U.S. Appl. No. 14/821,700 dated May 31, 2018.
Wang, et al., "Computer Aided-Diagnosis of Prostate Cancer on Multi para metric MRI: A Technical Review of Current Research," BioMed Research International, Aug. 2014, pp. 1-12, vol. 2014.
Yang, et al., "Comparison of Quantitative Parameters in Cervix Cancer Measured by Dynamic Contrast 2013 Enhanced MRI and CT," Magnetic Resonance in Medicine, Jun. 2010, pp. 1601-1609, vol. 63, Issue 6.
Yang, et al., "Reproducibility Assessment of a Multiple Reference Tissue Method for Quantitative Dynamic Contrast Enhanced 2013 MRI Analysis," Magnetic Resonance in Medicine, Apr. 2009, pp. 851-859, vol. 61, Issue 4.
3D Human Models from 1D, 2D & 3D Inputs @3DBODY.TECH Oct. 17, 2018. Retrieved from the Internet on Feb. 17, 2021 URL: https://www.slideshare.net/AlfredoBallesterFern/3-dbt2018-id36ballesterv04pdf.
Corads-AI—Grand Challenge. Retrieved from the Internet on Feb. 17, 2021 URL: https://github.com/microsoft/lnnerEye-DeepLearning.
Extended European Search Report in EP 18788304.6 dated Jan. 13, 2021 (9 pages).
GitHub—Microsoft InnerEye DeepLearning Medical Imaging Deep Learning library to train and deploy models on Azure Machine Learning and Azure Stack. Retrieved from the Internet on Feb. 17, 2021 URL: https://grand-challenge.org/algorithms/corads-ai/.
Lessmann et al., Automated Assessment of COVID-19 Reporting and Data System and Chest CT Severity Scores in Patients Suspected of Having COVID-19 Using Artificial Intelligence. Radiology: vol. 298: No. 1—Jan. 2021 , https://pubs.rsna.org/doi/10.1148/radiol.2020202439.
MedSeg—free medical segmentation online. Retrieved from the Internet on Feb. 17, 2021 URL: https://www.medseg.ai.
Photo Tourism: Exploring Photo Collections in 3D. Retrieved from the Internet on Feb. 17, 2021 URL: http://phototour.cs.washington.edu/Photo_Tourism.pdf.

(56) References Cited

OTHER PUBLICATIONS

Point set registration—Wikipedia. Retrieved from the Internet on Feb. 17, 2021 URL: https://en.wikipedia.org/wiki/Point_set_registration.
Project InnerEye—Democratizing Medical Imaging AI—Microsoft Research. Retrieved from the Internet on Feb. 17, 2021 URL: https://www.microsoft.com/en-US/research/project/medical-image-analysis/.
Extended European Search Report in EP 17821418.5 dated Jul. 17, 2020 (10 pages).

* cited by examiner

| | A | B | C | D | E | F | G | H |
|---|---|---|---|---|---|---|---|---|
| 1 | T1 Mapping (ms) | T2 raw signal (ms) | T2 Mapping | delta Ktrans | tau (s) | Dt IVIM (x10-3mm^2/s) | fp IVIM | ADC (high b-values) (50-500-1000) |
| 2 | 1010 | 97 | 120 | 0.1 | 0.2 | 1.3 | 0.4 | 1.24 |
| 3 | | 59 | 97 | 0.4 | 1.0 | 0.5 | 1 | 0.8 |
| 4 | 1530 | 112 | 139 | 0 | 0.6 | 1.8 | 0.04 | 1.7 |
| 5 | | 30 | 75 | 0.4 | 1.4 | 1.3 | 1 | 1 |
| 6 | 2030 | 122 | 168 | -0.2 | 1.2 | 2.15 | 0.06 | 1.92 |
| 7 | | 108 | 88 | 0.3 | 0.4 | 1.4 | 0.5 | 1.24 |
| ... | ... | ... | ... | ... | ... | ... | ... | ... |
| N | 1030 | 102 | 114 | -0.025 | 0 | 1.45 | 0.02 | 1.48 |

Fig. 1B

| | I | J | K | L | M | N | O | P | Q |
|---|---|---|---|---|---|---|---|---|---|
| 1 | nADC (high b-values) (50-500-1000) | R* (s-1) | Ktrans$^{TM}$ (min-1) | Ktrans (ETM) | Ktrans (SSM) | Ve$^{TM}$ | Ve (SSM) | Average Ve | Average Ktrans |
| 2 | 0.53 | 12 | 0.298 | 0.22 | 0.2 | 0.5 | 0.7 | 0.6 | 0.23933 |
| 3 | 0.4 | 20 | 2.798 | 0.5 | 0.5 | 0.4 | 0.4 | 0.4 | 1.26600 |
| 4 | 0.7 | 1 | 0.253 | 0.19 | 0.25 | 0.25 | 0.4 | 0.325 | 0.23100 |
| 5 | 0.4 | 45 | 1.298 | 0.55 | 0.8 | 0.2 | 0.3 | 0.25 | 0.88267 |
| 6 | 0.55 | 1.2 | 0.753 | 0.25 | 0.45 | 0.45 | 0.8 | 0.625 | 0.48433 |
| 7 | 0.41 | 10 | 1.798 | 0.3 | 0.5 | 0.47 | 0.5 | 0.485 | 0.88600 |
| ... | ... | ... | ... | ... | ... | ... | ... | ... | ... |
| N | 0.85 | 0.8 | 0.003 | 0.13 | 0.05 | 0.05 | 0 | 0.025 | 0.06100 |

Fig. 1C

| | R | S | T | U | V | W | X | Y |
|---|---|---|---|---|---|---|---|---|
| 1 | Prostate biopsy result | The percentage of cancer in a prostate biopsy tissue | Gleason score | Primary Gleason grade | Secondary Gleason grade | Biopsy tissue diameter | Biopsy tissue length | The number of MRI slices through a prostate biopsy tissue |
| 2 | Cancer | 30% | 6 | 3 | 3 | 1.194 mm | 13 mm | 4 |
| 3 | Cancer | 70% | 9 | 5 | 4 | 1.067 mm | 18 mm | 6 |
| 4 | Normal | 0% | 0 | 0 | 0 | 0.838 mm | 9 mm | 3 |
| 5 | Cancer | 40% | 10 | 5 | 5 | 0.838 mm | 15 mm | 5 |
| 6 | Benign | 0% | 0 | 0 | 0 | 1.194 mm | 12 mm | 4 |
| 7 | Cancer | 50% | 7 | 3 | 4 | 1.067 mm | 18 mm | 6 |
| ... | ... | ... | ... | ... | ... | ... | ... | ... |
| N | Normal | 0% | 0 | 0 | 0 | 1.194 mm | 9 mm | 3 |

Fig. 1D

| | Z | AA | AB | AC | AD | AE | AF | AG |
|---|---|---|---|---|---|---|---|---|
| | MRI area resolution | MRI slice thickness (T) | PSA (ng/dl) | PSA Velocity (ng/mL/year) | % free PSA | Histology subtype | Location within a given anatomical structure of gland | Tumor size (mm³) |
| 1 | | | | | | | | |
| 2 | 0.796 mm² | 3 mm | 10 | 0.3 | 10 | adenocarcinoma | Peripheral gland | |
| 3 | 0.94 mm² | 3 mm | 4 | 0.6 | 4 | adenocarcinoma | Transitional zone | |
| 4 | 0.597 mm² | 3 mm | | | 18 | | | |
| 5 | 0.524 mm² | 3 mm | 35 | 0.75 | 5 | mucinous | Peripheral gland | |
| 6 | 0.796 mm² | 3 mm | | | 30 | | | |
| 7 | 0.597 mm² | 3 mm | 3 | 0.5 | 3 | small cell | Peripheral gland | |
| ... | ... | ... | ... | ... | ... | ... | ... | ... |
| N | 0.94 mm² | 3 mm | | | 7 | | | |

Fig. 1E

| AH | AI | AJ | AK | AL |
|---|---|---|---|---|
| PRADS | Pathological Diagnosis | Pimonidazole Immunoscore (hypoxia marker) | Pimonidazole Genescore (hypoxia marker) | Primary Tumor (T) |
| 1 | | | | |
| 3 | | 1 | -0.3 | T1a |
| 4 | | 2 | 0.3 | T3b |
| 2 | Prostatitis | | | |
| 5 | BPH | 5 | 0.3 | T4 |
| 1 | | | | |
| 3 | | 2 | 0 | T2a |
| ... | ... | ... | ... | ... |
| 3 | PIN | | | |

Fig. 1F

| | AM | AN | AO | AP | AQ | AR |
|---|---|---|---|---|---|---|
| | Regional Lymph Nodes (N) | Distant Metastasis (M) | Sex | Age | Race | Weight (Kg) |
| 1 | N0 | M0 | Male | 60 | Yellow | 65 |
| 2 | N1 | M0 | Male | 65 | Black | 80 |
| 3 | | | Male | 68 | White | 85 |
| 4 | N1 | M1a | Male | 59 | Black | 82 |
| 5 | | | Male | 55 | Yellow | 75 |
| 6 | N0 | M0 | Male | 63 | White | 79 |
| ... | ... | ... | ... | ... | ... | ... |
| N | | | Male | 60 | Black | 78 |

Fig. 1G

|   | A | B | C | D | E | F | G | H |
|---|---|---|---|---|---|---|---|---|
|   | T1 Mapping (ms) | T2 raw signal (ms) | T2 Mapping | delta Ktrans | tau (s) | Dt IVIM (x10-3mm^2/s) | fp IVIM | ADC (high b-values) (50-500-1000) |
| 1 |  |  |  |  |  |  |  |  |
| 2 | 0.69 |  |  | 0.03 | 0.95 | 0.64 | 11.1 | 1.2 |
| 3 | 0.4 |  |  | 0.033 | 1 | 0.71 | 12.3 | 0.6 |
| 4 |  |  |  | 0.002 |  |  |  |  |
| 5 | 0.6 |  |  | 0.05 | 2 | 0.82 | 13.3 | 1 |
| 6 |  |  |  | 0 |  |  |  |  |
| 7 | 0.15 |  |  | 0.06 | 4 | 0.66 | 15.3 | 1.1 |
| ... |  |  | ... |  | ... |  | ... |  |
| N |  |  |  | 0.015 |  |  |  |  |

Fig. 1H

| | I | J | K | L | M | N | O | P | Q |
|---|---|---|---|---|---|---|---|---|---|
| 1 | MD from DTI | R* (s-1) | Ktrans™ (min-1) | Ktrans (ETM) | Ktrans (SSM) | Ve™ | Ve (SSM) | Average Ve | Average Ktrans |
| 2 | 0.71 | 2.4 | 0.110 | 0.42 | 0.180 | 0.57 | 0.32 | 0.445 | 0.237 |
| 3 | 0.94 | 11.6 | 0.087 | 0.68 | 0.131 | 0.79 | 0.2 | 0.495 | 0.299 |
| 4 | 1.26 | | | | | | | | |
| 5 | 0.48 | 12.5 | 0.164 | 0.2 | 0.254 | 0.35 | 0.4 | 0.375 | 0.206 |
| 6 | | | 0.033 | 0.3 | 0.034 | 0.21 | | | 0.122 |
| 7 | 0.86 | 2.7 | 0.559 | 0.21 | 1.63 | 0.47 | 0.6 | 0.535 | 0.800 |
| ... | ... | ... | ... | ... | ... | ... | ... | ... | ... |
| N | 0.7 | | | | | | | | |

Fig. 1I

| | R | S | T | U | V | W | X | Y | Z | |
|---|---|---|---|---|---|---|---|---|---|---|
| | Kep (TM) | Kep (SSM) | (DCE HETERO) CKC-TTP | (DCE HETERO) P | (DCE HETERO) CKC-WOS | (DCE HETERO) sigma | (DCE HETERO) mu | (DCE HETERO) CKC-PE | (DCE HETERO) CKC-WIS | |
| 1 | | | | | | | | | | |
| 2 | 0.452 | 0.447 | -0.5 | 0.05 | 0.025 | 0.0005 | | 0.0075 | 0.008 | |
| 3 | 0.161 | 0.147 | -1 | 0.05 | -0.03 | 0.0006 | | 2.5 | 3.0 | |
| 4 | | | | | | | | | | |
| 5 | 0.532 | 0.432 | -0.05 | 2.0 | -0.05 | -2 | | 2.0 | 2.2 | |
| 6 | 0.11 | 0.053 | | | | | | | | |
| 7 | 1.8 | 2.96 | | | | | | | | |
| ... | ... | ... | ... | ... | ... | ... | ... | ... | ... | |
| N | | | | | | | | | | |

Fig. 1J

| | AA | AB | AC | AD | AE | AF | AG | AH |
|---|---|---|---|---|---|---|---|---|
| 1 | Breast biopsy result | The percentage of cancer in a breast biopsy tissue | Biopsy tissue diameter | Biopsy tissue length | The number of MRI slices through a breast biopsy tissue | MRI area resolution | MRI slice thickness (T) | (PET) SUVmax |
| 2 | Cancer | 30% | 2.997 mm | 13 mm | 4 | 0.796 mm² | 3 mm | 7.5 |
| 3 | Cancer | 70% | 2.997 mm | 18 mm | 6 | 0.94 mm² | 3 mm | 6 |
| 4 | Benign Tissue | 0% | 2.997 mm | 9 mm | 3 | 0.597 mm² | 3 mm | |
| 5 | Cancer | 40% | 2.692 mm | 15 mm | 5 | 0.524 mm² | 3 mm | 10 |
| 6 | Benign Lesion | 0% | 2.692 mm | 12 mm | 4 | 0.796 mm² | 3 mm | |
| 7 | Cancer | 50% | 2.997 mm | 18 mm | 6 | 0.597 mm² | 3 mm | 7 |
| ... | ... | ... | ... | ... | ... | ... | ... | ... |
| N | Normal | 0% | 2.997 mm | 9 mm | 3 | 0.94 mm² | 3 mm | |

Fig. 1K

| | AI | AJ | AK | AL | AM | AN | AO | AP |
|---|---|---|---|---|---|---|---|---|
| | ER+ | PR+ | HER2/neu+ | Immunohistochemistry Subtype | Path | BIRADS | Oncotype DX Score | Primary Tumor (T) |
| 1 | | | | | | | | |
| 2 | Y | | | luminal A | IDC/DCIS | 4 | 10 | |
| 3 | Y | | | luminal A | IDC/DCIS | 4 | 15 | |
| 4 | | | | | Fibroadenoma | | | |
| 5 | Y | | | luminal A | IDC/DCIS | 5 | 20 | |
| 6 | | | | | Lobular carcinoma in situ | 5 | | |
| 7 | | | | triple negative | IDC/DCIS | 5 | | |
| ... | ... | ... | ... | ... | ... | ... | ... | ... |
| N | | | | | Cyst | | | |

Fig. 1L

| AQ | AR | AS | AT | AU | AV | AW | AX |
|---|---|---|---|---|---|---|---|
| Regional Lymph Nodes (N) | Distant Metastasis (M) | Tumor size | Location | Sex | Age | Race | Weight (Kg) |
| | | | | Female | 45 | Yellow | 48 |
| | | | | Female | 50 | White | 55 |
| | | | | Female | 45 | White | 56 |
| | | | | Female | 40 | White | 53 |
| | | | | Female | 50 | Yellow | 46 |
| | | | | Female | 38 | Black | 58 |
| . . . | . . . | . . . | . . . | . . . | . . . | . . . | . . . |
| | | | | Female | 48 | White | 57 |

Fig. 1M

|  | MRI Slice $SI_1$ | MRI Slice $SI_2$ | MRI Slice $SI_3$ | MRI Slice $SI_4$ |
|---|---|---|---|---|
| T1 mapping for Voxel 96a | 1010 | 1003 | 1021 | 1014 |
| T1 mapping for Voxel 96b | 1000 | 1011 | 1016 | 1030 |
| T1 mapping for Voxel 96c | 1005 | 1014 | 1007 | 1015 |
| T1 mapping for Voxel 96d | 1020 | 1001 | 1013 | 1025 |
| T1 mapping for Voxel 96e | 1019 | 1003 | 1031 | 1002 |
| T1 mapping for Voxel 96f | 1022 | 1009 | 1028 | 1000 |
| The percentage of the area A1 occupying the ROI 94 | 6% | 6% | 6% | 6% |
| The percentage of the area A2 occupying the ROI 94 | 38% | 38% | 38% | 38% |
| The percentage of the area A3 occupying the ROI 94 | 6% | 6% | 6% | 6% |
| The percentage of the area A4 occupying the ROI 94 | 6% | 6% | 6% | 6% |
| The percentage of the area A5 occupying the ROI 94 | 38% | 38% | 38% | 38% |
| The percentage of the area A6 occupying the ROI 94 | 6% | 6% | 6% | 6% |
| T1 mapping for ROI 94 | 1010.64 | 1006.94 | 1022 | 1015.4 |

Fig. 2D

| | |
|---|---|
| T1 mapping for Voxel 14a | 1010 |
| T1 mapping for Voxel 14b | 1000 |
| T1 mapping for Voxel 14c | 1005 |
| T1 mapping for Voxel 14d | 1020 |
| T1 mapping for Voxel 14e | 1019 |
| T1 mapping for Voxel 14f | 1022 |
| The percentage of the area B1 occupying the moving window 2 | 6% |
| The percentage of the area B2 occupying the moving window 2 | 38% |
| The percentage of the area B3 occupying the moving window 2 | 6% |
| The percentage of the area B4 occupying the moving window 2 | 6% |
| The percentage of the area B5 occupying the moving window 2 | 38% |
| The percentage of the area B6 occupying the moving window 2 | 6% |
| Measure of T1 mapping for a stop of the moving window 2 | 1010.64 |

Fig. 7B

|  |  |  |
|---|---|---|
| V1 (0.8751) | V2 (0.9529) | V3 (0.2797) |
| V4 (0.7755) | V5 (0.6580) | V6 (0.4847) |
| V7 (0.0263) | V8 (0.3073) | V9 (0.7806) |

Fig. 11C

|  |  |  |
|---|---|---|
| V1 (0.8488) | V2 (0.7304) | V3 (0.5863) |
| V4 (0.6352) | V5 (0.6022) | V6 (0.5691) |
| V7 (0.4152) | V8 (0.4740) | V9 (0.5585) |

Fig. 11B

|  |  |  |
|---|---|---|
| V1 (0.8166) | V2 (0.7047) | V3 (0.5928) |
| V4 (0.6286) | V5 (0.6022) | V6 (0.5757) |
| V7 (0.4407) | V8 (0.4996) | V9 (0.5586) |

Fig. 11A

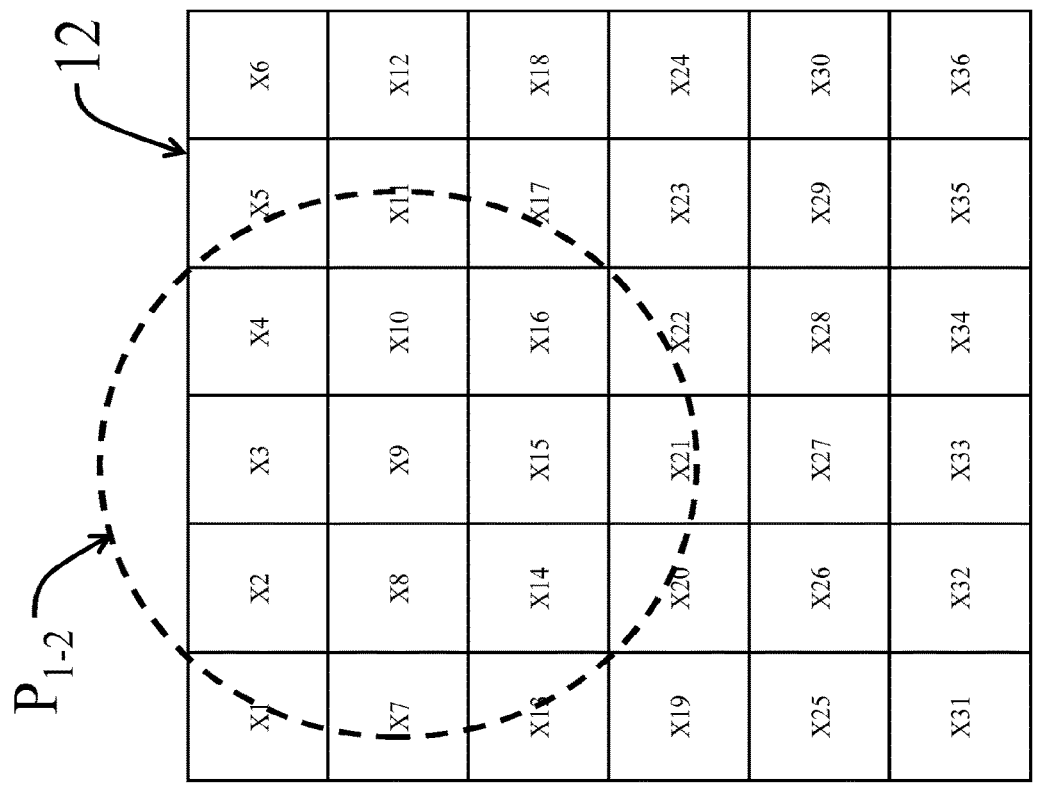
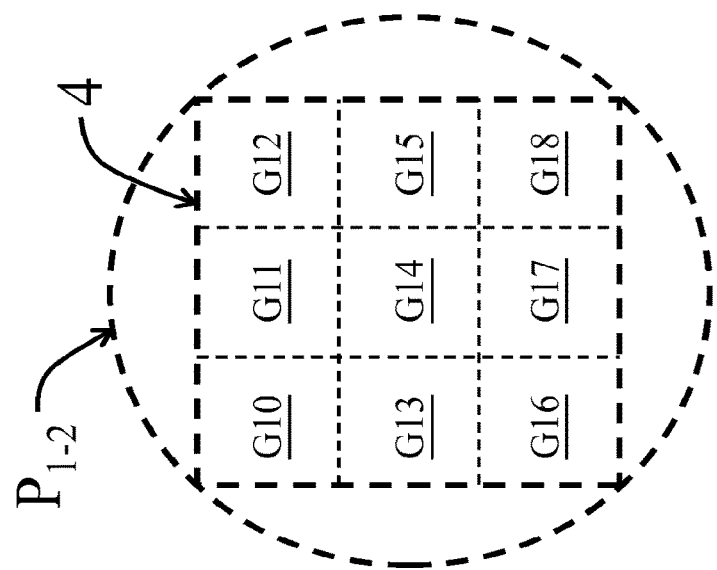
Fig. 13D
Fig. 13C

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T1 | non-contrast | Spin-Lattice Relaxation Time = standard MRI "weighting" for T1, representing time constant for longitudinal relaxation | Decreased in tumors compared to normal tissue, but nonspecific | Various methods, spin echo methods provide excellent SNR and resolution | Standard MRI method with various methods including Spin Echo, Gradient Recall Echo, etc. | | T1 tumor < T1 normal |
| | T1-standard | | | | | Direct measures of signal at a given echo time (TE), signal strength is a function of shape of signal recovery (logarithmic) and TE | |
| | T1 mapping | | | Various techniques exist, Deoni is a more known method | Varies | Provides a direct measure of the T1 value of the tissue = a parameter which determines the shape of the T1 signal versus TE curve | |
| T1 post | | Signal on T1 images after intravenous contrast injection is increased | Allows great visualization of vessels containing contrast and tissues with contrast leakage | Various methods, spin echo methods provide excellent SNR and resolution | Standard MRI method with various methods including Spin Echo, gradient echo, etc. | | T1 post tumor > T1 post normal |
| | T1-post | | | | | Measure of signal post contrast injection at a given TE | |
| [C] | T1-post [C] | Concentration of contrast is directly determined as a function of signal | Allows direct measures of MRI contrast concentration, used in DCE-MRI | Most often gradient recall echo (GRE) | Standard T1 methods | Mathematical modeling is used to determine [C] from known variables, including signal value | T1 post [C] > T1 post [C] normal |
| FLAIR | | "takes out" fluid signal | Mostly used in brain tumors and helps better delineate region of Tumor | Inversion recovery technique that eliminates signal from free fluid such as CSF | | | |

Fig. 20A

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T2 | | Spin-Spin Relaxation Time = standard MRI "weighting" for T2, representing time constant for transverse Relaxation | Increased in tumors compared to normal tissue, but nonspecific | Various methods, spin echo methods provide excellent SNR and resolution | Standard MRI method with various methods including Spin Echo, STIR, etc. | | T2 tumor > T2 normal |
| | T2-standard | | | | | Direct measures of signal at a given echo time TE, signal strength is a function of shape of signal recovery (exponential) and TE | |
| | T2 mapping | | | | | Provides a direct measure of the T2 value of the tissue = a parameter which determines the shape of the T2 signal versus TE curve | |
| Ktrans | | Forward exchange constant = index of vessel leakiness | Tumor vessels are more leaky than normal vessels | Dynamic Contrast-Enhanced MRI (DCE-MRI) | Contrast is injected into patient and serial T1 MRI images are obtained as contrast enters the tissue | Pharmacokinetic models are used that model motion of contrast molecules between vessel and the extracellular space | Ktrans tumor > Ktrans normal |
| | Ktrans "Tofts Model" (TM) | | | | | Different DCE-MRI software packages using TM include OHSU, VU, UP, ISM, BWH-GE, BWH-3D Slicer | |
| | Ktrans "Extended Tofts Model" (ETM) | | | | | Different DCE-MRI software packages using ETM include VU, UM, UW, BWH-GE | |
| | Ktrans "Shutterspeed Model" (SSM) | | | | | Different DCE-MRI software packages using SSM include OHSU, VU | |
| delta Ktrans (Δ Ktrans) | Delta Ktrans "Shutterspeed Model" (SSM) | Takes difference of Ktrans measured using SSM and TM | Research shows that this measure can be highly specific for cancers | DCE-MRI | Contrast is injected into patient and serial MRI images are obtained as contrast enters the tissue | Different DCE-MRI software packages using SSM include OHSU, VU | Δ Ktrans tumor > Δ Ktrans normal |

Fig. 20B

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Ve | | Volume of Exchange = volume of the extracellular extravascular space | Contrast leak from vessels into the Ve and the size of this space can vary | DCE-MRI | Contrast is injected into patient and serial MRI images are obtained as contrast enters the tissue | Pharmacokinetic models are used that model motion of contrast molecules between vessel and the extracellular space | Varies |
| | Ve "Tofts Model" (TM) | | | | | Different DCE-MRI software packages using TM include OHSU, VU, UP, ISM, BWH-GE, BWH-3D Slicer | |
| | Ve "Extended Tofts Model" (ETM) | | | | | Different DCE-MRI software packages using ETM include VU, UM, UW, BWH-GE | |
| | Ve "Shutterspeed Model" (SSM) | | | | | Different DCE-MRI software packages using SSM include OHSU, VU | |
| Vb | | Volume of Blood in exchange with tissue | Vascularity varies with different tumors and can vary after treatment | DCE-MRI | Contrast is injected into patient and serial MRI images are obtained as contrast enters the tissue | Pharmacokinetic models are used that model motion of contrast molecules between vessel and the extracellular space | Varies |
| | Vb "Extended Tofts Model" (ETM) | Parameter only derived from the "Extended Tofts Model" (ETM) | | | | Different DCE-MRI software packages using ETM include VU, UM, UW, BWH-GE | |
| Dt | Dt IVIM | Measure of "true" diffusion without effects of "pseudodiffusion" and signal from moving blood | Cancers have higher water restriction than normal tissues | IVIM from Diffusion-Weighted Imaging (DWI) MRI | Gradients at various "b values" of weighting are applied and the signal in tissue is measured at each b value | Simple IVIM mathematical model is used to determine Dt from signal decay at various b values, b=0 and other low b values are used for calculation. | Dt tumor < Dt normal |

Fig. 20C

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Dp | Dp IVIM | Measure of pseudodiffusion | | IVIM from DWI MRI | Gradients at various "b values" of weighting are applied and the signal in tissue is measured at each b value | Simple IVIM mathematical model is used to determine fp from signal decay at various b values, b=0 and other low b values are used for calculation. | Varies |
| fp | fp IVIM | Fractional plasma volume | Vascularity varies with different tumors and can vary after treatment | IVIM from DWI MRI | Gradients at various "b values" of weighting are applied and the signal in tissue is measured at each b value | Simple IVIM mathematical model is used to determine fp from signal decay at various b values, b=0 and other low b values are used for calculation. | Varies |
| tau | tau "Shutterspeed Model" (SSM) | Tau is an extra parameter added to the SSM to model time for protons to complex with MRI contrast | Research shows that this measure can be highly specific for cancers, likely related to Sodium levels | DCE-MRI | Contrast is injected into patient and serial MRI images are obtained as contrast enters the tissue | Different DCE-MRI software packages using SSM include OHSU, VU | tau tumor > tau normal |
| Hyperpolarized MRI | Various types of Hy MRI parameters | Hyperpolarized C13 substrates injected and imaged | Can image many metabolites, as well as quantify pH | | | | |
| ADC | | Measure of Restriction of Random Water Motion | Cancers have higher water restriction than normal tissues | DWI MRI | Gradients at various "b values" of weighting are applied and the signal in tissue is measured at each b value | | |
| | ADC standard | | | | | b value of "zero" is first measured = no gradient. Signal at various other b values are then also measured. ADC is the slope of the log of the signal decay. Signal does not decay as quickly in tumors. | ADC tumor < ADC normal |
| | ADC high b-values | | | | | ADC is measured only for high b values excluding b=0, typically high b values range up to 1000 | |

Fig. 20D

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| ADCo | ADCo Oscillating gradient spin echo (OGSE) | Better able to probe intracellular signal | Cancers have higher water restriction than normal tissues | Oscillating gradients with DWI MRI | OGSE at various "b values" of weighting, but the gradients are oscillated | ADC is measured in a similar manner to standard ADC | ADC tumor < ADC normal |
| kep | | Reverse exchange constant = index of vessel leakiness | Tumor vessels are more leaky than normal vessels | DCE-MRI | Contrast is injected into patient and serial MRI images are obtained as contrast enters the tissue | Pharmacokinetic models are used that model motion of contrast molecules between vessel and the extracellular space | kep tumor > kep normal |
| | kep "Tofts Model" (TM) | | | | | Different DCE-MRI software packages using TM include OHSU, VU, UP, ISM, BWHGE, BWH-3D Slicer | |
| | kep "Extended Tofts Model" (ETM) | | | | | Different DCE-MRI software packages using ETM include VU, UM, UW, BWH-GE | |
| | kep "Shutterspeed Model" (SSM) | | | | | Different DCE-MRI software packages using SSM include OHSU, VU | |
| AUC | | Area under the curve of signal from contrast entering tumor over time | Provides a "semi-quantitative" measure of tumor vessel leakage | DCE-MRI | Contrast is injected into patient and serial MRI images are obtained as contrast enters the tissue | Graphs are created of signal from contrast entering tumor over time for each voxel and AUC is calculated | AUC tumor > AUC normal |
| TTP | | Time to peak = measure of point of maximal contrast on tumor curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and TTP is calculated | TTP tumor > TTP normal |
| MPE | | Maximal peak enhancement = maximal concentration in tumor during tumor time curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and MPE is calculated | MPE tumor > MPE normal |

Fig. 20E

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Df | Df biexponential | Fast difusion component | Index of "fast" diffusion at low b values | DWI MRI | Gradients at various "b values" of weighting are applied and the signal in tissue is measured at each b value | A biexponential fit model is applied to the graph of signal decay | Varies |
|  | Ds biexponential | Slow difusion component | Index of "slow" diffusion at high b values |  |  |  | Ds tumor > Ds normal |
| D |  | Diffusion Parameter "fit" from modeling of the signal decay | Cancers have higher water restriction than normal tissues | DWI MRI | Gradients at various "b values" of weighting are applied and the signal in tissue is measured at each b value |  |  |
|  | D stretched biexponential |  |  |  |  | A "stretched" biexponential fit model is applied to the graph of signal decay | D tumor > D normal |
|  | D kurtosis |  |  |  |  | A kurtosis fit model is applied to the graph of signal decay | D tumor > D normal |
| CBF |  | Measures os signal from moving blood | Tumors often have increased blood flow | Different MRI acquisitions are used for CBF measures |  |  |  |
|  | CBF-ASL |  |  | Various ASL pulse sequences exist | Arterial Spin Labeling (ASL) "tags" moving blood and measures signal in a volume of interest | Signal is directly measured |  |
|  | CBF-DSC | Only used for brain tumors, does not work in body imaging |  | Various DSC, but usually a Echo Planar sequence is used | T2* effects measure signal drop after a bolus injection of contrast, degree of drop corelates with amount of signal from blood | Models of signal changes are used to extract parameters, most interesting of which are CBF and CBV | CBF tumor > CBF normal |

Fig. 20F

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| R* | | Index of oxygenation, BOLD imaging | Hypoxic regions of cancers are most resistant to various treatments | Intrinsic Susceptibility Imaging (ISI) using various pulse sequences sensitive to T2* Effects | T2* effects measure signal in regions of relative decreased oxygenation | | R* tumor < R* normal |
| RSI-CM | | Measure of Restriction of INTRACELLULAR Random Water Motion | Better differentiates tumor from normal and edema | Resonance Spectral Imaging (RSI) from DWI MRI | Gradients at various "b values" up to 4000 are applied and the signal in tissue is measured at each b value | A linear mixture model is used to model signal across b values, does not assume Gaussian like DTI (below) | RSI-CM tumor > RSI-CM normal |
| Various DTI Tensor Parameters | tensor measure(s) | Various tensor parameters provide info on direction of water diffusion | Some good recent applications for tumors, but mainly used for tractography | Diffusion Tensor Imaging (DTI) from DWI MRI | Gradients are applied in many directions using a few b values | Models are applied to determine direction of water motion based an assumption of a gaussian distribution | Varies |
| Na | | Measures sodium (Na) content in tissues by exciting Na instead of H (protons) | Elevated sodium is very specific for cancer | Special coils etc for Sodium Imaging, Na iaging will improve with increasing field strength and new 7 Tesla MRI machines | Na is excited instead of H, and signal is detected | Signal is measured at each voxel and correlates to Na levels | Na tumor > Na normal |
| Spectroscopy MRI | | Imaging of various peaks following excitation, for example can quantify increased lactate in tumors | | | | | |
| CEST | Various types of CEST parameters | Allows indirect detection of metabolites with exchangeable protons using special contrast agents | | T1 post contrast method | | | |

Fig. 20G

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| MRI contrast agents | | Various contrast agents available or being developed to complex with Gadolinium (the standard MRI contrast agent) | These developing techniques offer the potential for enormous variety in specific characterization of cancer receptors, metabolites, stem cell tracking etc. | Usually standard T1 sequences | Contrast agent injected and MRI images obtained | | |
| | Gadoxetate (Eovist) | Specific for uptake by liver hepatic cells | Great for sensitive identification of liver mets | Currently FDA approved and clinically used | | | E tumor < E normal |
| | Receptor Imaging | Various probes to target receptors overexposed in cancers | Examples include hormone receptors in breast cancer, EGFR important for mets, etc. | | | | |
| | USPIO | Very sensitive iron oxide agents, signal loss with uptake in normal lymph nodes | Great for identifying lymph nodes metastasis in vivo | | T2* effects | | |
| | F19 MRI | Used to label and track stem cells | | | | | |
| | nanoparticles/ thernostics | Huge area of research aimed at creating nanoparticles to enter cancer cells and deliver treatment | Usually complexed with MRI contrast agent for visualization | | | | |

Fig. 20H

| "Parent" Parameter | Subset Parameter | Brief Description | Why useful? | Brief Description of Data Processing |
|---|---|---|---|---|
| SUVmax from PET | | Standard PET/CT measures uptake of F18, a measure of glycolysis | In general, nuclear medicine techniques offer more signal from a "smaller" event – the disadvantage is poor resolution | CT or MRI and PET are registered and SUVmax is determined after calibration for CT attenuation etc. |
| | SUVmax F18 FDG | | Some tumor types and advanced tumors have increased uptake, but only for select cancers | |
| | SUVmax F18-Choline | | Has shown increased specificity for prostate cancer metastasis | |
| | SUVmax F18-FLT | | More sensitive for some cancers | |
| PET tracers | | Various PET tracers are under investigation for targeted specific receptors etc. | | |

Fig. 20I

| "Parent" Parameter | Subset Parameter | Brief Description | Why useful? | Brief Description of Analysis Technique | How do parameter measures compare to normal tissue? |
|---|---|---|---|---|---|
| Heterogeneity Features | | Measures of heterogeneity have shown strong correlation with tumor genetics = radiogenomics | Models can be applied to CT or MRI or PET | | Heterogeneity tumor > heterogeneity normal |
| | Hot Spot Measures | Regions of interest (ROIs) are placed only in mapping areas showing largest or smallest values | Better correlation to tumor grading, staging, etc. | | |
| | Histogram methods | Provides info on histograms, for example value for peak height, standard deviation, skew, kurtosis, etc. | Some studies show this analysis correlates better to tumor characteristics than hot spot analysis | | |
| | Xf | Measures of fraction of a certain parameter, for example, fraction of enhancing voxels | Better correlation to tumor grading, staging, etc. | | |
| | textural analysis | Haralick method most often used | | | |
| | fractal techniques | Imposing regular grids of a range of scales on a binary object in question and then counting the number of grid elements (boxes) that are occupied by the object at each scale | | | |
| | Minkowski functionals | Analyse binarized images over a range of thresholds and also quantify space-filling properties of tumors | | | |
| | Clustering Techniques | Multi-spectral analyses use pattern recognition techniques that simultaneously analyze images to identify voxel clusters in a multi-dimensional feature space. A classifier then groups individual voxels together based on their similarities and differences. | Starts to approach of techniques, limitation with these techniques is for demonstrating changes after treatment due to changing sizes of subregions. Other research (i.e., FDM) indicates that ROI before and after treatment should be held constant. | Group multiparameter data with clustering searches for voxels demonstrating certain patterns | |

Fig. 20J

| "Parent" Parameter | Brief Description |
|---|---|
| Raman Imaging | Animal imaging only, chemical images based on Raman Spectrum, resolution to 25nm |
| Micro_PET | Animal imaging only, with multiple probes with PET |
| Bioluminescence Optical Imaging | Animal imaging only, fluescent tags to markers in vivo |
| Ultrasound | US is generally only used for clinical identification. Some research with ultrasound "molecular imaging" tracers which could be married with treatment options such as High Intensity Focused Ultrasound. US is also used to identify biopsy location and to fuse images with other modalities such as MRI. US has a limited role for quantification of parameter measures. |

Fig. 20K

| Parameter | Brief Description |
|---|---|
| Gleason score | The Gleason grading system is used to help evaluate the prognosis of men with prostate cancer. Lower grades are associated with small, closely packed glands. Cells spread out and lose glandular architecture as grade increases. The pathologist then sums the pattern-number of the primary and secondary Gleason grades to obtain the final Gleason score. |
| Primary Gleason grade | assigned to the dominant pattern of the tumor (has to be greater than 50% of the total pattern seen), i.e., the primary pattern |
| Secondary Gleason grade | assigned to the next-most frequent pattern (has to be less than 50%, but at least 5%, of the pattern of the total cancer observed), i.e., the secondary pattern |

Fig. 20L

| Parameter | Brief Description |
|---|---|
| Prostate Specific Antigen (PSA) | 1. PSA is also known as gamma-seminoprotein or kallikrein-3 (KLK3)<br>2. PSA is a glycoprotein enzyme encoded in humans by the KLK3 gene<br>3. PSA is present in small quantities in the blood of men with healthy prostates, but is often elevated in the presence of prostate cancer or other prostate disorders |
| PSA Velocity | Men with prostate cancer whose PSA level increased by more than 2.0 ng per milliliter during the year before the diagnosis of prostate cancer have a higher risk of death from prostate cancer despite undergoing radical prostatectomy. |
| % Free PSA | Most PSA in the blood is bound to serum proteins. A small amount is not protein bound and is called 'free PSA'. In men with prostate cancer the ratio of free (unbound) PSA to total PSA is decreased. |
| Histological Subtype | Tissue sub typing based on histology. Histology (compound of the Greek words: ἱστός histos "tissue", and -λογία -logia "science") is the study of the microscopic anatomy of cells and tissues of plants and animals. It is commonly performed by examining cells and tissues under a light microscope or electron microscope, which have been sectioned, stained and mounted on a microscope slide. Histological studies may be conducted using tissue culture, where live human or animal cells are isolated and maintained in an artificial environment for various research projects. The ability to visualize or differentially identify microscopic structures is frequently enhanced through the use of histological stains. Histology is an essential tool of biology and medicine. Histopathology, the microscopic study of diseased tissue, is an important tool in anatomical pathology, since accurate diagnosis of cancer and other diseases usually requires histopathological examination of samples. |
| Tumor size | Tumor size measures are taken in a number of ways, this could be based on later pathology from surgical specimen, or could be based on imaging. In imaging for clinical trials and in some clinical care, the RECIST system is used which only one diameter measures. Tumor segmentation method are also used to determine the borders and determine areas and volumes. Measures could vary based on the type of imaging used. So, a database could be populated by a number of different size measures. |
| PRADS | An imaging classification system based on various imaging characteristics on mpMRI to determine probability of cancer |
| Prostatitis | Inflammation of the prostate gland |
| Pimonidazole immunoscore | Exogenous hypoxia marker pimonidazole is a 2-nitroimidazole compound, which forms covalent bonds with cellular macromolecules at oxygen levels below 1.3% and visualises poorly oxygenated regions in histological sections from tumours. |
| Pimonidazole genescore | Construction of a pimonidazole gene signature. To find essential genes reflected by pimonidazole staining, the five most significant gene sets covering the three phenotypes proliferation, repair and hypoxia response are selected, and the 32 genes with a positive correlation to pimonidazole immuno- score are extracted. A pimonidazole gene score for each tumour is calculated by averaging the median-centred, log-transformed expression levels of the genes, to achieve a measure of the signature that could be compared in other cohorts. The gene score is higher for pimonidazole-positive tumours and in patients with high clinical stage and lymph node metastasis. |

Fig. 20M

| Parameter | Brief Description |
|---|---|
| TNM Staging System For Prostate Cancer | Tumor, Node, Metastasis Staging. Exact staging system is determined for each cancer and is determined by tumor size, areas of invasion, locations of nodal metastasis, and distant metastases.<br><br>1. Primary Tumor (T):<br>*Clinical*<br>TX: Primary tumor cannot be assessed<br>T0: No evidence of primary tumor<br>T1: Clinically inapparent tumor neither palpable nor visible by imaging<br>    T1a: Tumor incidental histologic finding in 5% or less of tissue resected<br>    T1b: Tumor incidental histologic finding in more than 5% of tissue resected<br>    T1c: Tumor identified by needle biopsy (e.g., because of elevated PSA)<br>T2: Tumor confined within prostate<br>    T2a: Tumor involves one-half of one lobe or less<br>    T2b: Tumor involves more than one-half of one lobe but not both lobes<br>    T2c: Tumor involves both lobes<br>T3: Tumor extends through the prostatic capsule<br>    T3a: Extracapsular extension (unilateral or bilateral)<br>    T3b: Tumor invades the seminal vesicle(s)<br>T4: Tumor is fixed or invades adjacent structures other than seminal vesicles: bladder, levator muscles, and/or pelvic wall.<br><br>*Pathologic(pT)*<br>pT2: Organ confined<br>    pT2a: Unilateral, involving one-half of one side or less<br>    pT2b: Unilateral, involving more than one-half of one side but not both sides<br>    pT2c: Bilateral disease<br>pT3: Extraprostatic extension<br>    pT3a: Extraprostatic extension or microscopic invasion of the bladder neck<br>    pT3b: Seminal vesicle invasion<br>pT4: Invasion of bladder, rectum |

Fig. 20N

| Parameter | Brief Description |
| --- | --- |
| TNM Staging System For Prostate Cancer | 2. Regional Lymph Nodes (N):<br>*Clinical*<br>NX: Regional lymph nodes were not assessed<br>N0: No regional lymph node metastasis<br>N1: Metastasis in regional lymph node(s)<br><br>*Pathologic*<br>PNX: Regional nodes not sampled<br>pN0: No positive regional nodes<br>pN1: Metastases in regional nodes(s)<br><br>3. Distant Metastasis (M):<br>M0: No distant metastasis<br>M1: Distant metastasis<br>    M1a: Non-regional lymph node(s)<br>    M1b: Bone(s)<br>    M1c: Other site(s) with or without bone disease |
| Atypia | Atypia is a pathologic term for a structural abnormality in a cell |
| Benign Prostatic Hypertrophy (BPH) | Age-associated prostate gland enlargement |
| Prostatic Intraepithelial Neoplasia (PIN) | Prostatic intraepithelial neoplasia (PIN) is an abnormality of prostatic glands and believed to precede the development of prostate adenocarcinoma |
| Atrophy | (of body tissue or an organ) waste away, typically due to the degeneration of cells |

Fig. 200

| Parameter | Brief Description |
|---|---|
| Immunohistochemical subtype | Subtype classified by immunohistochemistry, which refers to the process of detecting antigens (e.g., proteins) in cells of a tissue section by exploiting the principle of antibodies binding specifically to antigens in biological tissues. |
| Luminal A | Immunohistochemical subtype of breast cancer with ER+ and/or PR+ expression with HER2- |
| Luminal B | Immunohistochemical subtype of breast cancer with ER+ and/or PR+ expression with HER2+ |
| Triple Negative/Basal-like | Immunohistochemical subtype of breast cancer with ER, PR, Her2 all negative |
| HER2 subtype | Immunohistochemical subtype of breast cancer with ER- and PR- expression with HER2+ |
| BIRADS | BIRADS classification system. It is based on various imaging features, and there is both a mammography BIRADS and a breast MRI BIRADS. |
| Oncotype Dx Score | Score obtained from a kit that determines biomarker risk of tumor recurrence and response to chemo based of expression profiles of mRNA |
| Next generation sequencing (NGS) | The bases of a small fragment of DNA are sequentially identified from signals emitted as each fragment is re-synthesized from a DNA template strand. NGS extends this process across millions of reactions in a massively parallel fashion, rather than being limited to a single or a few DNA fragments. This advance enables rapid sequencing of large stretches of DNA base pairs spanning entire genomes, with instruments capable of producing hundreds of gigabases of data in a single sequencing run. Specific gene markers and NGS may be used to rapidly scan all the DNA data from tissue samples to identify up regulation of certain genes. For example, NGS is used to identify tissue samples with long RNA HOTAIR, which is associated with higher risk for metastasis. |
| mRNA biomarkers | Up-regulated mRNA within cells that signal up regulation of cellular DNA and have a proven correlation to some biological consequence to be called a biomarker. For example, Oncotype Dx is a Biomarker test which studies proved is associated with risk for recurrence and response to chemo. |
| DNA mutations | Certain DNA mutations act as cancer biomarkers. For example, BRCA mutations are associated with increased risk for breast cancer. |
| TNM Staging System For Breast Cancer | 1. Primary Tumor (T): The T classification of the primary tumor is the same regardless of whether it is based on clinical or pathologic criteria, or both. Size should be measured to the nearest millimeter. If the tumor size is slightly less than or greater than a cutoff for a given T classification, it is recommended that the size be rounded to the millimeter reading that is closest to the cutoff. For example, a reported size of 1.1 mm is reported as 1 mm, or a size of 2.01 cm is reported as 2.0 cm. Designation should be made with the subscript "c" or "p" modifier to indicate whether the T classification was determined by clinical (physical examination or radiologic) or pathologic measurements, respectively. In general, pathologic determination should take precedence over clinical determination of T size.<br><br>TX: Primary tumor cannot be assessed<br>T0: No evidence of primary tumor |

Fig. 20P

| Parameter | Brief Description |
|---|---|
| TNM Staging System For Breast Cancer | Tis: Carcinoma in situ<br>Tis (DCIS): Ductal carcinoma in situ<br>Tis (LCIS): Lobular carcinoma in situ<br>Tis (Paget's): Paget's disease of the nipple NOT associated with invasive carcinoma and/or carcinoma in situ (DCIS and/or LCIS) in the underlying breast parenchyma. Carcinomas in the breast parenchyma associated with Paget's disease are categorized based on the size and characteristics of the parenchymal disease, although the presence of Paget's disease should still be noted<br>T1: Tumor ≤20 mm or less in greatest dimension<br>    T1mi: Tumor ≤1 mm in greatest dimension<br>    T1a: Tumor >1 mm but ≤5 mm in greatest dimension<br>    T1b: Tumor >5 mm but ≤10 mm in greatest dimension<br>    T1c: Tumor >10 mm but ≤20 mm in greatest dimension<br>T2: Tumor >20 mm but ≤50 mm in greatest dimension<br>T3: Tumor >50 mm in greatest dimension<br>T4: Tumor of any size with direct extension to the chest wall and/or to the skin (ulceration or skin nodules).<br>Note: Invasion of the dermis alone does not qualify as T4<br>    T4a: Extension to the chest wall, not including only pectoralis muscle adherence/invasion<br>    T4b: Ulceration and/or ipsilateral satellite nodules and/or edema (including peau d'orange) of the skin, which do not meet the criteria for inflammatory carcinoma<br>    T4c: Both T4a and T4b<br>    T4d: Inflammatory carcinoma<br><br>2. Regional Lymph Nodes (N):<br>*Clinical*<br>NX: Regional lymph nodes cannot be assessed (e.g., previously removed)<br>N0: No regional lymph node metastasis<br>N1: Metastases to movable ipsilateral level I, II axillary lymph node(s)<br>N2: Metastases in ipsilateral level I, II axillary lymph nodes that are clinically fixed or matted; or in clinically detected ipsilateral internal mammary nodes in the absence of clinically evident axillary lymph node metastases<br>    N2a: Metastases in ipsilateral level I, II axillary lymph nodes fixed to one another (matted) or to other structures<br>    N2b: Metastases only in clinically detected ipsilateral internal mammary nodes and in the absence of clinically evident level I, II axillary lymph node metastases<br>N3: Metastases in ipsilateral infraclavicular (level III axillary) lymph node(s) with or without level I, II axillary lymph node involvement; or in clinically detected ipsilateral internal mammary lymph node(s) with clinically evident level I, II axillary lymph node metastases; or metastases in ipsilateral supraclavicular lymph node(s) with or without axillary or internal mammary lymph node involvement<br>    N3a: Metastasis in ipsilateral infraclavicular lymph node(s)<br>    N3b: Metastasis in ipsilateral internal mammary lymph node(s) and axillary lymph node(s)<br>    N3c: Metastasis in ipsilateral supraclavicular lymph node(s) |

Fig. 20Q

| Parameter | Brief Description |
|---|---|
| TNM Staging System For Breast Cancer | *Pathologic (pN)*<br>pNX: Regional lymph nodes cannot be assessed (e.g., previously removed, or not removed for pathologic study)<br>pN0: No regional lymph node metastasis histologically<br>Note: Isolated tumor cell clusters (ITC) are defined as small clusters of cells not greater than 0.2 mm, or single tumor cells, or a cluster of fewer than 200 cells in a single histologic cross-section. ITCs may be detected by routine histology or by immunohistochemical (IHC) methods. Nodes containing only ITCs are excluded from the total positive node count for purposes of N classification but should be included in the total number of nodes evaluated.<br>  pN0(i-): No regional lymph node metastasis histologically, negative IHC<br>  pN0(I+): Malignant cells in regional lymph node(s) no greater than 0.2 mm (detected by H&E or IHC including ITC)<br>  pN0(mol-): No regional lymph node metastases histologically, negative molecular findings (RT-PCR)<br>  pN0(mol+): Positive molecular findings (RT-PCR), but no regional lymph node metastases detected by histology or IHC<br>pN1: Micrometastases; or metastases in 1–3 axillary lymph nodes; and/or in internal mammary nodes with metastases detected by sentinel lymph node biopsy but not clinically detected<br>  pN1mi: Micrometastases (greater than 0.2 mm and/or more than 200 cells, but none greater than 2.0 mm)<br>  pN1a: Metastases in 1–3 axillary lymph nodes, at least one metastasis greater than 2.0 mm<br>  pN1b: Metastases in internal mammary nodes with micrometastases or macrometastases detected by sentinel lymph node biopsy but not clinically detected<br>  pN1c: Metastases in 1–3 axillary lymph nodes and in internal mammary lymph nodes with micrometastases or macrometastases detected by sentinel lymph node biopsy but not clinically detected<br>pN2: Metastases in 4–9 axillary lymph nodes; or in clinically detected internal mammary lymph nodes in the absence of axillary lymph node metastases<br>  pN2a: Metastases in 4–9 axillary lymph nodes (at least one tumor deposit greater than 2.0 mm)<br>  pN2b: Metastases in clinically detected internal mammary lymph nodes in the absence of axillary lymph node metastases<br>pN3: Metastases in ten or more axillary lymph nodes; or in infraclavicular (level III axillary) lymph nodes; or in clinically detected ipsilateral internal mammary lymph nodes in the presence of one or more positive level I, II axillary lymph nodes; or in more than three axillary lymph nodes and in internal mammary lymph nodes with micrometastases or macrometastases detected by sentinel lymph node biopsy but not clinically detected; or in ipsilateral supraclavicular lymph nodes<br>  pN3a: Metastases in ten or more axillary lymph nodes (at least one tumor deposit greater than 2.0 mm); or metastases to the infraclavicular (level III axillary lymph) nodes<br>  pN3b: Metastases in clinically detected ipsilateral internal mammary lymph nodes in the presence of one or more positive axillary lymph nodes; or in more than three axillary lymph nodes and in internal mammary lymph nodes with micrometastases or macrometastases detected by sentinel lymph node biopsy but not clinically detected<br>  pN3c: Metastasis in ipsilateral supraclavicular lymph nodes<br><br>3. Distant Metastasis (M):<br>M0: No clinical or radiographic evidence of distant metastases<br>cM0(I+): No clinical or radiographic evidence of distant metastases, but deposits of molecularly or microscopically detected tumor cells in circulating blood, bone marrow, or other nonregional nodal tissue that are no larger than 0.2 mm in a patient without symptoms or signs of metastases<br>M1: Distant detectable metastases as determined by classic clinical and radiographic means and/or histologically proven larger than 0.2 mm |

Fig. 20R

METHOD AND SYSTEM FOR ASSESSING IMAGES USING BIOMARKERS

This application is a continuation of U.S. application Ser. No. 14/821,703, now U.S. Pat. No. 9,922,433, filed Aug. 8, 2015, which claims priority to U.S. Appl. No. 62/167,940, filed on May 29, 2015, the contents of which are incorporated herein by reference in their entireties.

BACKGROUND OF THE DISCLOSURE

Field of the Disclosure

The disclosure relates to a method of forming a probability map, and more particularly, to a method of forming a probability map based on molecular and structural imaging data, such as magnetic resonance imaging (MRI) parameters, computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, or based on other structural imaging data, such as from CT and/or ultrasound images.

BRIEF DESCRIPTION OF THE RELATED ART

Big Data represents the information assets characterized by such a high volume, velocity and variety to require specific technology and analytical methods for its transformation into value. Big Data is used to describe a wide range of concepts: from the technological ability to store, aggregate, and process data, to the cultural shift that is pervasively invading business and society, both drowning in information overload. Precision medicine is a medical model that proposes the customization of healthcare—with medical decisions, practices, and/or products being tailored to the individual patient. In this model, diagnostic testing is often employed for selecting appropriate and optimal therapies based on the context of a patient's genetic content or other molecular or cellular analysis.

SUMMARY OF THE DISCLOSURE

The invention proposes an objective to provide a method of forming a probability map based on molecular and/or structural imaging data, such as MRI parameters, CT parameters, PET parameters, SPECT parameters, micro-PET parameters, micro-SPECT parameters, Raman parameters, and/or BLO parameters, and/or other structural imaging data, such as from CT and/or ultrasound images, for a first subject (e.g., an individual patient). The method may build a dataset or database of big data containing molecular and/or structural imaging data (and/or other structural imaging data) for multiple second subjects and biopsy tissue-based data associated with the molecular and/or structural imaging data for the second subjects. A classifier or biomarker library may be constructed or established from the dataset or database of big data. The invention proposes a computing method including an algorithm for generating a voxelwise probability map of a specific tissue or tumor characteristic for the first subject from the first subject's registered imaging dataset including the molecular and/or structural imaging data for the first subject. The computing method includes the step of matching the registered ones of the molecular and/or structural imaging data for the first subject to a dataset from the established or constructed classifier or biomarker library obtained from population-based information for the molecular and/or structural imaging (and/or other structural imaging) data for the second subjects and other information (such as clinical and demographic data or the biopsy tissue-based data) associated with the molecular and/or structural imaging data for the second subjects. The method provides direct biopsy tissue-based evidence (i.e., a large amount of the biopsy tissue-based data in the dataset or database of big data) for a medical or biological test or diagnosis of tissues or organs of the first subject and shows heterogeneity within a single tumor focus with high sensitivity and specificity.

The invention also proposes an objective to provide a method of forming a probability change map based on imaging data of a first subject before and after a medical treatment. The imaging data for the first subject may include (1) molecular and/or structural imaging data, such as MRI parameters, CT parameters, PET parameters, SPECT parameters, micro-PET parameters, micro-SPECT parameters, Raman parameters, and/or BLO parameters, and/or (2) other structural imaging data, such as from CT and/or ultrasound images. The method may build a dataset or database of big data containing molecular and/or structural imaging (and/or other structural imaging) data for multiple second subjects and biopsy tissue-based data associated with the molecular and/or structural imaging data for the second subjects. A classifier or biomarker library may be constructed or established from the dataset or database of big data. The invention proposes a computing method including an algorithm for generating a probability change map of a specific tissue or tumor characteristic for the first subject from the first subject's molecular and/or structural imaging (and/or other structural imaging) data before and after the medical treatment. The computing method includes matching the registered ones of the molecular and/or structural imaging (and/or other structural imaging) data of the first subject before and after the medical treatment in the first subject's registered (multi-parametric) image dataset to the established or constructed classifier or biomarker library. The method matches the molecular and/or structural imaging (and/or other structural imaging) data for the first subject to the established or constructed classifier or biomarker library derived from direct biopsy tissue-based evidence (i.e., a large amount of the biopsy tissue-based data in the dataset or database of big data) to obtain the change of probabilities for the response and/or progression of the medical treatment and show heterogeneity of the response and/or progression within a single tumor focus with high sensitivity and specificity. The invention provides a method for effectively and timely evaluating the effectiveness of the medical treatment, such as neoadjuvant chemotherapy for breast cancer, or radiation treatment for prostate cancer.

The invention also proposes an objective to provide a method for collecting data for an image-tissue-clinical database for cancers.

The invention also proposes an objective to apply a big data technology to build a probability map from multi-parameter molecular and/or structural imaging data, including MRI parameters, PET parameters, SPECT parameters, micro-PET parameters, micro-SPECT parameters, Raman parameters, and/or BLO parameters, and/or from other imaging data, including data from CT and/or ultrasound images. The invention provides a non-invasive method (such as molecular and/or structural imaging methods, for example, MRI, Raman imaging, CT imaging) to diagnose a specific tissue characteristic, such as breast cancer cells or prostate cancer cells, with better resolution (resolution size is 50% smaller, or 25% smaller than the current resolution capability), and with a higher confidence level. With data accumulated in the dataset or database of big data, the confidence level (for example, percentage of accurate diagnosis of a specific cancer cell) can be greater than 90%, or 95%, and eventually, greater than 99%.

The invention also proposes an objective to apply a big data technology to build a probability change map from imaging data before and after a treatment. The imaging data may include (1) molecular and structural imaging data, including MRI parameters, CT parameters, PET parameters, SPECT parameters, micro-PET parameters, micro-SPECT parameters, Raman parameters, and/or BLO parameters, and/or (2) other structural imaging data, including data from CT and/or ultrasound images. The invention provides a method for effectively and timely evaluating the effectiveness of a treatment, such as neoadjuvant chemotherapy for breast cancer or radiation treatment for prostate cancer.

In order to achieve the above objectives, the invention may provide a method of forming a probability map composed of multiple computation voxels with the same size or volume. The method may include the following steps. First, a big data database (or called a database of big data) including multiple data sets is created. Each of the data sets in the big data database may include a first set of information data, which may be obtained by a non-invasive method or a less-invasive method (as compared to a method used to obtain the following second set of information data), may be obtained more easily (than the method used to obtain the following second set of information data), or may provide information, obtained by a non-invasive method, for a specific tissue, to be biopsied or to be obtained by an invasive method, of an organ (e.g., prostate or breast) of a subject with a spatial volume covering, e.g., less than 10% or even less than 1% of the spatial volume of the organ of the subject. The organ of the subject, for example, may be the prostate or breast of a human patient. The first set of data information may include measures of molecular and/or structural imaging parameters, such as measures of MRI parameters and/or CT parameters, and/or other structural imaging parameters, such as from CT and/or ultrasound images, for a volume and location of the specific tissue to be biopsied (e.g., prostate or breast) from the organ of the subject. The "other structural imaging parameters" may not be mentioned hereinafter. Each of the molecular and/or structural imaging parameters for the specific tissue may have a measure calculated based on an average of measures, for said each of the molecular and/or structural imaging parameters, obtained from corresponding registered regions, portions, locations or volumes of interest of multiple molecular and/or structural images, such as MRI slices, PET slices, or SPECT images, registered to or aligned with respective regions, portions, locations or volumes of interest of the specific tissue to be biopsied. The combination of the registered regions, portions, locations or volumes of interest of the molecular and/or structural images may have a total volume covering and substantially equaling the total volume of the specific tissue to be biopsied. Each of the data sets in the big data database may further include the second set of information data, which may be obtained by an invasive method or a more-invasive method (as compared to the method used to obtain the above first set of information data), may be obtained with more difficulty (as compared to the method used to obtain the above first set of information data), or may provide information for the specific tissue, having been biopsied or obtained by an invasive method, of the organ of the subject. The second set of information data may provide information data with decisive, conclusive results for a better judgment or decision making. For example, the second set of information data may include a biopsy result, data or information (i.e., pathologist diagnosis, for example cancer or no cancer) for the biopsied specific tissue. Each of the data sets in the big data database may also include: (1) dimensions related to molecular and/or structural imaging for the parameters, such as the thickness T of an MRI slice and the size of an MRI voxel of the MRI slice, including the width of the MRI voxel and the thickness or height of the MRI voxel (which may be the same as the thickness T of the MRI slice), (2) clinical data (e.g., age and sex of the patient and/or Gleason score of a prostate cancer) associated with the biopsied specific tissue and/or the subject, and (3) risk factors for cancer associated with the subject (such as smoking history, sun exposure, premalignant lesions, and/or gene). For example, if the biopsied specific tissue is obtained by a needle, the biopsied specific tissue is cylinder-shaped with a diameter or radius Rn (that is, an inner diameter or radius of the needle) and a height tT normalized to the thickness T of the MRI slice. The invention proposes a method to transform the volume of the cylinder-shaped biopsied specific tissue (or Volume of Interest (VOI), which is $\pi \times Rn^2 \times tT$) into other shapes for easy or meaningful computing purposes, for medical instrumentation purposes, or for clearer final data presentation purposes. For example, the long cylinder of the biopsy specific tissue (with radius Rn and height tT) may be transformed into a planar cylinder (with radius Rw, which is the radius Rn multiplied by the square root of the number of the MRI slices having the specific tissue to be biopsied extend therethrough) to match the MRI slice thickness T. The information of the radius Rw of the planner cylinder, which has a volume the same or about the same as the volume of the biopsied specific tissue, i.e., VOI, and has a height of the MRI slice thickness T, is used to define the size (e.g., the radius) of a moving window in calculating a probability map for a patient (e.g., human). The invention proposes that, for each of the data sets, the volume of the biopsy specific tissue, i.e., VOI, may be substantially equal to the volume of the moving window to be used in calculating probability maps. In other words, the volume of the biopsy specific tissue, i.e., VOI, defines the size of the moving window to be used in calculating probability maps. The concept of obtaining a feature size (e.g., the radius) of the moving window to be used in calculating a probability map for an MRI slice is disclosed as above mentioned. Statistically, the moving window may be determined with the radius Rw (i.e., feature size), perpendicular to a thickness of the moving window, based on a statistical distribution or average of the radii Rw (calculated from VOIs) associated with a subset data from the big data database. Next, a classifier for an event such as biopsy-diagnosed tissue characteristic for specific cancerous cells or occurrence of prostate cancer or breast cancer is created based on the subset data associated with the event from the big data database. The subset data may be obtained from all data associated with the given event. A classifier or biomarker library can be constructed or obtained using statistical methods, correlation methods, big data methods, and/or learning and training methods.

After the big data database and the classifier are created or constructed, an image of a patient, such as MRI slice image (i.e., a molecular image) or other suitable image, is obtained by a device or system such as MRI system. Furthermore, based on the feature size, e.g., the radius Rw, of the moving window obtained from the subset data in the big data database, the size of a computation voxel, which becomes the basic unit of the probability map, is defined. If the moving window is circular, the biggest square inscribed in the moving window is then defined. Next, the biggest square is divided into $n^2$ small squares each having a width Wsq, where n is an integer, such as 2, 3, 4, 5, 6, or more than 6. The divided squares define the size and shape of the computation voxels in the probability map for the image of the patient. The moving window may move across the patient's image at a regular step or interval of a fixed distance, e.g., substantially equal to the width Wsq of the computation voxels. A stop of the moving window overlaps the neighboring stop of the moving window. Alternatively, the biggest square may be divided into n rectangles each having a width Wrec and a length Lrec, where n is an integer, such as 2, 3, 4, 5, 6, 7, 8, or more than 8. The divided rectangles define the size and shape of the computation voxels in the probability map for the image of the patient. The moving window may move across the patient's image at a regular step or interval of a fixed distance, e.g., substantially equal to the width of the computation voxels (i.e., the width Wrec), in the x direction and at a regular step or interval of a fixed distance, e.g., substantially equal to the length of computation voxels (i.e., the length Lrec), in the y direction. A stop of the moving window overlaps the neighboring stop of the moving window. In an alternative embodiment, each of the stops of the moving window may have a width, length or diameter less than the side length (e.g., the width or length) of voxels, such as defined by a resolution of a MRI system, in the image of the patient.

After the size and shape of the computation voxel is obtained or defined, the stepping of the moving window and the overlapping between two neighboring stops of the moving window can then be determined. Measures of specific imaging parameters for each stop of the moving window are obtained from the patient's molecular and/or structural imaging information or image. The specific imaging parameters may include molecular and/or structural imaging parameters, such as MRI parameters, PET parameters, SPECT parameters, micro-PET parameters, micro-SPECT parameters, Raman parameters, and/or BLO parameters, and/or other imaging parameters, such as CT parameters and/or ultrasound parameters. Each of the specific imaging parameters for each stop of the moving window may have a measure calculated based on an average of measures, for said each of the specific imaging parameters, for voxels of the patient's image inside said each stop of the moving window. Some voxels of the patient's image may be only partially inside said each stop of the moving window. The average, for example, may be obtained from the measures, in said each stop of the moving window, each weighed by its area proportion of an area of the voxel for said each measure to an area of said each stop of the moving window. A registered (multi-parametric) image dataset may be created for the patient to include multiple imaging parameters, such as molecular parameters and/or other imaging parameters, obtained from various equipment, machines, or devices, at a defined time-point (e.g., specific date) or in a time range (e.g., within five days after treatment). Each of the image parameters in the patient's registered (multi-parametric) image dataset requires alignment or registration. The registration can be done by, for examples, using unique anatomical marks, structures, tissues, geometry, shapes or using mathematical algorithms and computer pattern recognition.

Next, the specific imaging parameters for each stop of the moving window may be reduced using, e.g., subset selection, aggregation, and dimensionality reduction into a parameter set for said each stop of the moving window. In other words, the parameter set includes measures for independent imaging parameters. The imaging parameters selected in the parameter set may have multiple types, such as two types, more than two types, more than three types, or more than four types, (statistically) independent from each other or one another, or may have a single type. For example, the imaging parameters selected in the parameter set may include (a) MRI parameters and PET parameters, (b) MRI parameters and SPET parameters, (c) MRI parameters and CT parameters, (d) MRI parameters and ultrasound imaging parameters, (e) Raman imaging parameters and CT parameters, (f) Raman imaging parameters and ultrasound imaging parameters, (g) MRI parameters, PET parameters, and ultrasound imaging parameters, or (h) MRI parameters, PET parameters, and CT parameters.

Next, the parameter set for each stop of the moving window is matched to the classifier to obtain a probability PW of the event for said each stop of the moving window. This invention discloses an algorithm to compute a probability of the event for each of the computation voxels from the probabilities PWs of the event for the stops of the moving window covering said each of the computation voxels, as described in the following steps ST1-ST11. In the step ST1, a first probability PV1 for each of the computation voxels is calculated or assumed based on an average of the probabilities PWs of the event for the stops of the moving window overlapping said each of the computation voxels. In the step ST2, a first probability guess PG1 for each stop of the moving window is calculated by averaging the first probabilities PV1s (obtained in the step ST1) of all the computation voxels inside said each stop of the moving widow. In the step ST3, the first probability guess PG1 for each stop of the moving window is compared with the probability PW of the event for said each stop of the moving window by subtracting the probability PW of the event from the first probability guess PG1 for said each stop of the moving window so that a first difference DW1 (DW1=PG1−PW) between the first probability guess PG1 and the probability PW of the event for said each stop of the moving window is obtained. In the step ST4, a first comparison is performed to determine whether the absolute value of the first difference DW1 for each stop of the moving window is less than or equal to a preset threshold error. If any one of the absolute values of all the first differences DW1s is greater than the preset threshold error, the step ST5 continues. If the absolute values of all the first differences DW1s are less than or equal to the preset threshold error, the step ST11 continues. In the step ST5, a first error correction factor (ECF1) for each of the computation voxels is calculated by summing error correction contributions from the stops of the moving window overlapping said each of the computation voxels. For example, if there are four stops of the moving window overlapping one of the computation voxels, the error correction contribution from each of the four stops to said one of the computation voxels is calculated by obtaining an area ratio of an overlapped area between said one of the computation voxels and said each of the four stops to an area of the biggest square inscribed in said each of the four stops, and then multiplying the first difference DW1 for said each of the four stops by the area ratio. In the step ST6, a second probability PV2 for each of the computation voxels is calculated by subtracting the first error correction factor ECF1 for said each of the computation voxels from the first probability PV1 for said each of the computation voxels (PV2=PV1−ECF1). In the step ST7, a second probability guess PG2 for each stop of the moving window is calculated by averaging the second probabilities PV2s (obtained in the step ST6) of all the computation voxels inside said each stop of the moving widow. In the step ST8, the second probability guess PG2 for each stop of the moving window is compared with the probability PW of the event for said each stop of the moving window by subtracting the probability PW of the event from the second probability guess PG2 for said each stop of the moving window so that a second difference DW2 (DW2=PG2−PW) between the second probability guess PG2 and the probability PW of the event for said each stop of the moving window is obtained. In the step S9, a second comparison is performed to determine whether the absolute value of the second difference DW2 for each stop of the moving window is less than or equal the preset threshold error. If any one of the absolute values of all the second differences DW2s is greater than the preset threshold error, the step ST10 continues. If the absolute values of all the second differences DW2s are less than or equal to the preset threshold error, the step ST11 continues. In the step ST10, the steps ST5-ST9 are repeated or iterated, using the newly obtained the $n^{th}$ difference DWn between the $n^{th}$ probability guess PGn and the probability PW of the event for each stop of the moving window for calculation in the $(n+1)^{th}$ iteration, until the absolute value of the $(n+1)^{th}$ difference DW(n+1) for said each stop of the moving window is equal to or less than the preset threshold error (Note: PV1, PG1 and DW1 for the first iteration, ECF1, PV2, PG2 and DW2 for the second iteration, and ECF(n−1), PVn, PGn and DWn for the $n^{th}$ iteration). In the step ST11, the first probabilities PV1s in the first iteration, i.e., the steps ST1-ST4, the second probabilities PV2s in the second iteration, i.e., the steps ST5-ST9, or the $(n+1)^{th}$ probabilities PV(n+1)s in the $(n+1)^{th}$ iteration, i.e., the step ST10, are used to form the probability map. The probabilities of the event for the computation voxels are obtained using the above method, procedure or algorithm, based on overlapped stops of the moving window, to form the probability map of the event for the image of the patient (e.g., patient's MRI slice) having imaging information (e.g., molecular and/or structural imaging information). The above process using the moving window in the x-y direction would create a two-dimensional (2D) probability map. In order to obtain a three-dimensional (3D) probability map, the above processes for all MRI slices of the patient would be performed in the z direction in addition to the x-y direction.

After the probability map is obtained, the patient may undergo a biopsy to obtain a tissue sample from an organ of the patient (i.e., that is shown on the image of the patient) at a suspected region of the probability map. The tissue sample is then sent to be examined by pathology. Based on the pathology diagnosis of the tissue sample, it can be determined whether the probabilities for the suspected region of the probability map are precise or not. In the invention, the probability map may provide information for a portion or all of the organ of the patient with a spatial volume greater than 80% or even 90% of the spatial volume of the organ, than the spatial volume of the tissue sample (which may be less than 10% or even 1% of the spatial volume of the organ), and/or than the spatial volume of the specific tissue provided for the first and second sets of information data in the big data database.

In order to further achieve the above objectives, the invention may provide a method of forming a probability-change map of the aforementioned event for a treatment. The method is described in the following steps: (1) obtaining probabilities of the event for respective stops of the moving window on pre-treatment and post-treatment images (e.g., MRI slice) of a patient in accordance with the methods and procedures as described above, wherein the probability of the event for each stop of the moving window on the pre-treatment image of the patient can be obtained based on measures for molecular and/or structural imaging parameters (and/or other imaging parameters) taken before the treatment; similarly, the probability of the event for each stop of the moving window on the post-treatment image of the patient can be obtained based on measures for the molecular and/or structural imaging parameters (and/or other imaging parameters) taken after the treatment; all the measures for the molecular and/or structural imaging parameters (or other imaging parameters) taken before the treatment are obtained from the registered (multi-parametric) image dataset for the pre-treatment image; all the measures for the molecular and/or structural imaging parameters (or other imaging parameters) taken after the treatment are obtained from the registered (multi-parametric) image dataset for the post-treatment image; (2) calculating a probability change PMC between the probabilities of the event before and after the treatment for each stop of the moving window; and (3) calculating a probability change PVC of each of computation voxels associated with the treatment based on the probability changes PMCs for the stops of the moving window by following the methods and procedures described above for calculating the probability of each of computation voxels from the probabilities of the stops of the moving window, that is, the probabilities are replaced with the probability changes PMCs for the stops of the moving window to perform the above methods to calculate the probability changes PVCs of the computation voxels. The obtained probability changes PVCs for the computation voxels then compose a probability-change map of the event for the treatment. Performing the above processes for all images (e.g., MRI slices) in the z direction, a 3D probability-change map of the event for the treatment can be obtained.

In general, the invention proposes an objective to provide a method, system (including, e.g., hardware, devices, computers, processors, software, and/or tools), device, tool, software or hardware for forming or generating a decision data map, e.g., a probability map, based on first data of a first type (e.g., first measures of MRI parameters) from a first subject such as a human or an animal. The method, system, device, tool, software or hardware may include building a database of big data (or call a big data database) including second data of the first type (e.g., second measures of the MRI parameters) from a population of second subjects and third data of a second type (e.g., biopsy results, data or information) from the population of second subjects. The third data of the second type may provide information data with decisive, conclusive results for a better judgment or decision making (e.g., a patient whether to have a specific cancer or not). The second and third data of the first and second types from each of the second subjects in the population, for example, may be obtained from a common portion of said each of the second subjects in the population. A classifier related to a decision-making characteristic (e.g., occurrence of prostate cancer or breast cancer) is established or constructed from the database of big data. The method, system, device, tool, software or hardware may provide a computing method including an algorithm for generating the decision data map with finer voxels associated with the decision-making characteristic for the first subject by matching the first data of the first type to the established or constructed classifier. The method, system, device, tool, software or hardware provides a decisive-and-conclusiveresult-based evidence for a better judgment or decision making based on the first data of the first type (without any data of the second type from the first subject). The second data of the first type, for example, may be obtained by a non-invasive method or a less-invasive method (as compared to a method used to obtain the third data of the second type) or may be obtained more easily (as compared to the method used to obtain the third data of the second type). The second data of the first type may provide information, obtained by, e.g., a non-invasive method, for a specific tissue, to be biopsied or to be obtained by an invasive method, of an organ of each second subject with a spatial volume covering, e.g., less than 10% or even less than 1% of the spatial volume of the organ of said each second subject. The second data of the first type may include measures or data of molecular imaging (and/or other imaging) parameters, such as measures of MRI parameters and/or CT data. The third data of the second type, for example, may be obtained by an invasive method or a more-invasive method (as compared to the method used to obtain the second data of the first type) or may be harder to obtain (as compared to the method used to obtain the second data of the first type). The third data of the second type may provide information for the specific tissue, having been biopsied or obtained by an invasive method, of the organ of each second subject. The third data of the second type may include biopsy results, data or information (for example a patient whether to have a cancer or not) for the biopsied specific tissues of the second subjects in the population. The decision making may be related to, for example, a decision on whether the first subject has cancerous cells or not. This invention provides a method to make better decision, judgment or conclusion for the first subject (a patient, for example) based on the first data of the first type, without any data of the second type from the first subject. This invention provides a method to use MRI imaging data to directly diagnose whether an organ or tissue (such as breast or prostate) of the first subject has cancerous cells or not without performing a biopsy test for the first subject. In general, this invention provides a method to make decisive conclusion, with 90% or over 90% of accuracy (or confidence level), or with 95% or over 95% of accuracy (or confidence level), or eventually, with 99% or over 99% of accuracy (or confidence level). Furthermore, the invention provides a probability map with its spatial resolution of computation voxels that is 75%, 50% or 25%, in one dimension (1D), smaller than that of machine-defined voxels of an image created by the current available method. The machine-defined voxels of the image, for example, may be voxels of an MRI image.

These, as well as other components, steps, features, benefits, and advantages of the present disclosure, will now become clear from a review of the following detailed description of illustrative embodiments, the accompanying drawings, and the claims.

BRIEF DESCRIPTION OF THE DRAWINGS

The drawings disclose illustrative embodiments of the present disclosure. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same reference number or reference indicator appears in different drawings, it may refer to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIGS. 1B-1G show a subset data table in accordance with an embodiment of the present invention;

FIGS. 1H-1M show a subset data table in accordance with an embodiment of the present invention;

FIG. 2D shows a data table in accordance with an embodiment of the present invention;

FIG. 7B shows a data table in accordance with an embodiment of the present invention;

FIGS. 11A, 11B, and 11C show initial probabilities for computation voxels, updated probabilities for the computation voxels, and optimal probabilities for the computation voxels, respectively, in accordance with an embodiment of the present invention;

FIGS. 13A, 13C, 13E, 13G, 14A, 14C, 14E, 14G, 15A, 15C, 15E, 15G, 16A, 16C, 16E, and 16G show sixteen stops of a circular moving window, each of which includes nine non-overlapped small squares, in accordance with an embodiment of the present invention;

FIGS. 13B, 13D, 13F, 13H, 14B, 14D, 14F, 14H, 15B, 15D, 15F, 15H, 16B, 16D, 16F, and 16H show a circular window moving across a computation region defined with thirty-six computation voxels in accordance with an embodiment of the present invention;

FIGS. 20A-20R show a description of various parameters ("parameter charts" and "biomarker" charts could be used to explain many items that could be included in a big data database, this would include the ontologies, mRNA, next generation sequencing, etc., and exact data in "subset" databases could then be more specific and more easily generated data);

Figure 1A:
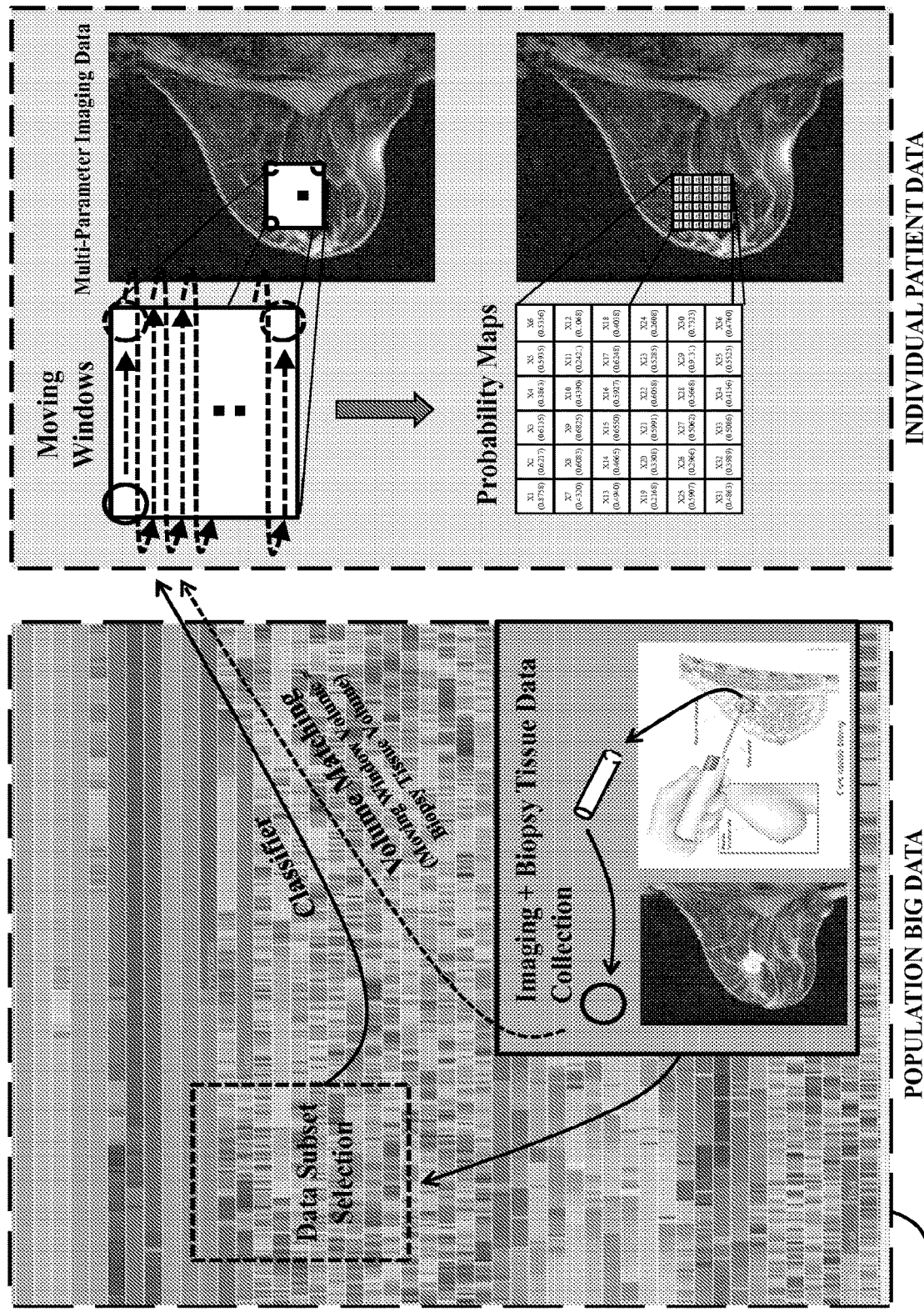
FIG. 1A is a schematic drawing showing a "Big Data" probability map creation in accordance with an embodiment of the present invention.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF THE INVENTION

Illustrative embodiments are now described. Other embodiments may be used in addition or instead. Details that may be apparent or unnecessary may be omitted to save space or for a more effective presentation. Conversely, some embodiments may be practiced without all of the details that are disclosed.

Computing methods described in the present invention may be performed on any type of image, such as molecular and structural image (e.g., MRI image, CT image, PET image, SPECT image, micro-PET, micro-SPECT, Raman image, or bioluminescence optical (BLO) image), structural image (e.g., CT image or ultrasound image), fluoroscopy image, structure/tissue image, optical image, infrared image, X-ray image, or any combination of these types of images, based on a registered (multi-parametric) image dataset for the image. The registered (multi-parametric) image dataset may include multiple imaging data or parameters obtained from one or more modalities, such as MRI, PET, SPECT, CT, fluoroscopy, ultrasound imaging, BLO imaging, micro-PET, micro-SPECT, Raman imaging, structure/tissue imaging, optical imaging, infrared imaging, and/or X-ray imaging. For a patient, the registered (multi-parametric) image dataset may be created by aligning or registering in space all parameters obtained from different times or from various machines. Methods in first, second and third embodiments of the invention may be performed on a MRI image based on the registered (multi-parametric) image dataset, including, e.g., MRI parameters and/or PET parameters, for the MRI image.

Referring to FIG. 1A, a big data database 70 is created to include multiple data sets, each of which may include: (1) a first set of information data, which may be obtained by a non-invasive method or a less-invasive method (as compared to a method used to obtain the following second set of information data), wherein the first set of data information may include measures for multiple imaging parameters, including, e.g., molecular and structural imaging parameters (such as MRI parameters, CT parameters, PET parameters, SPECT parameters, micro-PET parameters, micro-SPECT parameters, Raman parameters, and/or BLO parameters) and/or other structural imaging data (such as from CT and/or ultrasound images), for a volume and location of a tissue to be biopsied (e.g., prostate or breast) from a subject such as human or animal, (2) combinations each of specific some of the imaging parameters, (3) dimensions related to imaging parameters (e.g., molecular and structural imaging parameters), such as the thickness T of an MRI slice and the size of an MRI voxel of the MRI slice, including the width or side length of the MRI voxel and the thickness or height of the MRI voxel (which may be substantially equal to the thickness T of the MRI slice), (4) a second set of information data obtained by an invasive method or a more-invasive method (as compared to the method used to obtain the first set of information data), wherein the second set of the information data may include tissue-based information from a biopsy performed on the subject, (5) clinical data (e.g., age and sex of the subject and/or Gleason score of a prostate cancer) associated with the biopsied tissue and/or the subject, and (6) risk factors for cancer associated with the subject.

Some or all of the subjects for creating the big data database 70 may have been subjected to a treatment such as neoadjuvant chemotherapy or (preoperative) radiation therapy. Alternatively, some or all of the subjects for creating the big data database 70 are not subjected to a treatment such as neoadjuvant chemotherapy or (preoperative) radiation therapy. The imaging parameters in each of the data sets of the big data database 70 may be obtained from different modalities, including two or more of the following: MRI, PET, SPECT, CT, fluoroscopy, ultrasound imaging, BLO imaging, micro-PET, micro-SPECT, and Raman imaging. Accordingly, the imaging parameters in each of the data sets of the big data database 70 may include four or more types of MRI parameters depicted in FIGS. 20A-20H, one or more types of PET parameters depicted in FIG. 20I, one or more types of heterogeneity features depicted in FIG. 20J, and other parameters depicted in FIG. 20K. Alternatively, the first set of information data may only include a type of imaging parameter (such as T1 mapping). In each of the data sets of the big data database 70, each of the imaging parameters (such as T1 mapping) for the tissue to be biopsied may have a measure calculated based on an average of measures, for said each of the imaging parameters, for multiple regions, portions, locations or volumes of interest of multiple registered images (such as MRI slices) registered to or aligned with respective regions, portions, locations or volumes of the tissue to be biopsied, wherein all of the regions, portions, locations or volumes of interest of the registered images may have a total volume covering and substantially equaling the volume of the tissue to be biopsied. The number of the registered images for the tissue to be biopsied may be greater than or equal to 2, 5 or 10.

In the case of the biopsied tissue obtained by a needle, the biopsied tissue may be long cylinder-shaped with a radius Rn, which is substantially equal to an inner radius of the needle, and a height tT normalized to the thickness T of the MRI slice. In the invention, the volume of the long cylinder-shaped biopsied tissue may be transformed into another shape, which may have a volume the same or about the same as the volume of the long cylinder-shaped biopsied tissue (or Volume of Interest, VOI, which may be $\pi \times Rn^2 \times tT$), for easy or meaningful computing purposes, for medical instrumentation purposes, or for clearer final data presentation purposes. For example, the long cylinder of the biopsied tissue with the radius Rn and height tT may be transformed into a planar cylinder to match the MRI slice thickness T. The planar cylinder, for example, may have a height equal to the MRI slice thickness T, a radius Rw equal to the radius Rn multiplied by the square root of the number of the registered images, and a volume the same or about the same as the volume of the biopsied tissue, i.e., VOI. The radius Rw of the planner cylinder is used to define the size (e.g., the radius Rm) of a moving window MW in calculating a probability map for a patient (e.g., human). In the invention, the volume of the biopsied tissue, i.e., VOI, for each of the data sets, for example, may be substantially equal to the volume of the moving window MW to be used in calculating probability maps. In other words, the volume of the biopsied tissue, i.e., VOI, defines the size of the moving window MW to be used in calculating probability maps. Statistically, the moving window MW may be determined with the radius Rm, perpendicular to a thickness of the moving window MW, based on the statistical distribution or average of the radii Rw (calculated from multiple VOIs) associated with a subset data (e.g., the following subset data DB-1 or DB-2) from the big data database 70.

The tissue-based information in each of the data sets of the big data database 70 may include (1) a biopsy result, data, information (i.e., pathologist diagnosis, for example cancer or no cancer) for the biopsied tissue, (2) mRNA data or expression patterns, (3) DNA data or mutation patterns (including that obtained from next generation sequencing), (4) ontologies, (5) biopsy related feature size or volume (including the radius Rn of the biopsied tissue, the volume of the biopsied tissue (i.e., VOI), and/or the height tT of the biopsied tissue), and (6) other histological and biomarker findings such as necrosis, apoptosis, percentage of cancer, increased hypoxia, vascular reorganization, and receptor expression levels such as estrogen, progesterone, HER2, and EPGR receptors. For example, regarding the tissue-based information of the big data database 70, each of the data sets may include specific long chain mRNA biomarkers from next generation sequencing that are predictive of metastasis-free survival, such as HOTAIR, RP11-278 L15.2-001, LINC00511-009, AC004231.2-001. The clinical data in each of the data sets of the big data database 70 may include the timing of treatment, demographic data (e.g., age, sex, race, weight, family type, and residence of the subject), and TNM staging depicted in, e.g., FIGS. 20N and 20O or FIGS. 20P, 20Q and 20R. Each of the data sets of the big data database 70 may further include information regarding neoadjuvant chemotherapy and/or information regarding (preoperative) radiation therapy. Imaging protocol details, such as MRI magnet strength, pulse sequence parameters, PET dosing, time at PET imaging, may also be included in the big data database 70. The information regarding (preoperative) radiation therapy may include the type of radiation, the strength of radiation, the total dose of radiation, the number of fractions (depending on the type of cancer being treated), the duration of the fraction from start to finish, the dose of the fraction, the duration of the preoperative radiation therapy from start to finish, and the type of machine used for the preoperative radiation therapy. The information regarding neoadjuvant chemotherapy may include the given drug(s), the number of cycles (i.e., the duration of the neoadjuvant chemotherapy from start to finish), the duration of the cycle from start to finish, and the frequency of the cycle.

Data of interest are selected from the big data database 70 into a subset, used to build a classifier CF. The subset from the big data database 70 may be selected for a specific application, such as prostate cancer, breast cancer, breast cancer after neoadjuvant chemotherapy, or prostate cancer after radiation. In the case of the subset selected for prostate cancer, the subset may include data in a tissue-based or biopsy-based subset data DB-1. In the case of the subset selected for breast cancer, the subset may include data in a tissue-based or biopsy-based subset data DB-2. Using suitable methods, such as statistical methods, correlation methods, big data methods, and/or learning and training methods, the classifier CF may be constructed or created based on a first group associated with a first data type or feature (e.g., prostate cancer or breast cancer) in the subset, a second group associated with a second data type or feature (e.g., non-prostate cancer or non-breast cancer) in the subset, and some or all of the variables in the subset associated with the first and second groups. Accordingly, the classifier CF for an event, such as the first data type or feature, may be created based on the subset associated with the event from the big data database 70. The event may be a biopsy-diagnosed tissue characteristic, such as having specific cancerous cells, or occurrence of prostate cancer or breast cancer.

After the database 70 and the classifier CF are created or constructed, a probability map, composed of multiple computation voxels with the same size, is generated or constructed for, e.g., evaluating or determining the health status of a patient (e.g., human subject), the physical condition of an organ or other structure inside the patient's body, or the patient's progress and therapeutic effectiveness by the steps described below. First, an image of the patient is obtained by a device or system, such as MRI system. The image of the patient, for example, may be a molecular image (e.g., MRI image, PET image, SPECT image, micro-PET image, micro-SPECT image, Raman image, or BLO image) or other suitable image (e.g., CT image or ultrasound image). In addition, based on the radius Rm of the moving window MW obtained from the subset, e.g., the subset data DB-1 or DB-2, in the big data database 70, the size of the computation voxel, which becomes the basic unit of the probability map, is defined.

If the moving window MW is circular, the biggest square inscribed in the moving window MW is then defined. Next, the biggest square inscribed in the moving window MW is divided into $n^2$ small squares, i.e., cubes, each having a width Wsq, where n is an integer, such as 2, 3, 4, 5, 6, or more than 6. The divided squares define the size and shape of the computation voxels in the probability map for the image of the patient. For example, each of the computation voxels of the probability map may be defined as a square, i.e., cube, having the width Wsq and a volume the same or about the same as that of each of the divided squares. The moving window MW may move across the image of the patient at a regular step or interval of a fixed distance, e.g., substantially equal to the width Wsq (i.e., the width of the computation voxels), in the x and y directions. A stop of the moving window MW overlaps the neighboring stop of the moving window MW.

Alternatively, the biggest square inscribed in the moving window MW may be divided into n rectangles each having a width Wrec and a length Lrec, where n is an integer, such as 2, 3, 4, 5, 6, 7, 8, or more than 8. The divided rectangles define the size and shape of the computation voxels in the probability map for the image of the patient. Each of the computation voxels of the probability map, for example, may be a rectangle having the width Wrec, the length Lrec, and a volume the same or about the same as that of each of the divided rectangles. The moving window MW may move across the patient's molecular image at a regular step or interval of a fixed distance, e.g., substantially equal to the width Wrec (i.e., the width of the computation voxels), in the x direction and at a regular step or interval of a fixed distance, e.g., substantially equal to the length Lrec (i.e., the length of the computation voxels), in the y direction. A stop of the moving window MW overlaps the neighboring stop of the moving window MW. In an alternative embodiment, each of the stops of the moving window MW may have a width, length or diameter less than the side length (e.g., the width or length) of voxels in the image of the patient.

After the size and shape of the computation voxels are obtained or defined, the stepping of the moving window MW and the overlapping between two neighboring stops of the moving window MW can then be determined. Measures of specific imaging parameters for each stop of the moving window MW may be obtained from the patient's image and/or different parameter maps (e.g., MRI parameter map(s), PET parameter map(s) and/or CT parameter map(s)) registered to the patient's image. The specific imaging parameters may include two or more of the following: MRI parameters, PET parameters, SPECT parameters, micro-PET parameters, micro-SPECT parameters, Raman parameters, BLO parameters, CT parameters, and ultrasound imaging parameters. Each of the specific imaging parameters for each stop of the moving window MW, for example, may have a measure calculated based on an average of measures, for said each of the specific imaging parameters, for voxels of the patient's image inside said each stop of the moving window MW. In the case that some voxels of the patient's image only partially inside that stop of the moving window MW, the average can be weighed by the area proportion. The specific imaging parameters of different modalities may be obtained from registered image sets (or registered parameter maps), and rigid and nonrigid standard registration techniques may be used to get each section of anatomy into the same exact coordinate location on each of the registered (multi-parametric) image dataset.

A registered (multi-parametric) image dataset may be created for the patient to include multiple registered images (including two or more of the following: MRI slice images, PET images, SPECT images, micro-PET images, micro-SPECT images, Raman images, BLO images, CT images, and ultrasound images) and/or corresponding imaging parameters (including two or more of the following: MRI parameters, PET parameters, SPECT parameters, micro-PET parameters, micro-SPECT parameters, Raman parameters, BLO parameters, CT parameters, and/or ultrasound imaging parameters) obtained from various equipment, machines, or devices or from a defined time-point (e.g., specific date) or time range (e.g., within five days after treatment). Each of the imaging parameters in the patient's registered (multi-parametric) image dataset requires alignment or registration. The registration can be done by, for examples, using unique anatomical marks, structures, tissues, geometry, and/or shapes or using mathematical algorithms and computer pattern recognition. The measures of the specific imaging parameters for each stop of the moving window MW, for example, may be obtained from the registered (multi-parametric) image dataset for the patient.

Next, the specific imaging parameters for each stop of the moving window MW may be reduced using, e.g., subset selection, aggregation, and dimensionality reduction into a parameter set for said each stop of the moving window MW. In other words, the parameter set includes measures for independent imaging parameters. The imaging parameters used in the parameter set may have multiple types, such as two types, more than two types, more than three types, or more than four types, independent from each other or one another, or may have a single type. For example, the imaging parameters used in the parameter set may include (a) MRI parameters and PET parameters, (b) MRI parameters and SPET parameters, (c) MRI parameters and CT parameters, (d) MRI parameters and ultrasound imaging parameters, (e) Raman imaging parameters and CT parameters, (f) Raman imaging parameters and ultrasound imaging parameters, (g) MRI parameters, PET parameters, and ultrasound imaging parameters, or (h) MRI parameters, PET parameters, and CT parameters.

Next, the parameter set for each stop of the moving window MW is matched to the classifier CF to obtain a probability PW of the event for said each stop of the moving window MW. After the probabilities PWs of the event for the stops of the moving window MW are obtained, an algorithm is performed based on the probabilities PWs of the event for the stops of the moving window MW to compute probabilities of the event for the computation voxels, as mentioned in the following steps ST1-ST11. In the step ST1, a first probability PV1 for each of the computation voxels, for example, may be calculated or assumed based on an average of the probabilities PWs of the event for the stops of the moving window MW overlapping or covering said each of the computation voxels. In the step ST2, a first probability guess PG1 for each stop of the moving window MW is calculated by averaging the first probabilities PV1s (obtained in the step ST1) of all the computation voxels inside said each stop of the moving widow MW. In the step ST3, the first probability guess PG1 for each stop of the moving window MW is compared with the probability PW of the event for said each stop of the moving window MW by, e.g., subtracting the probability PW of the event from the first probability guess PG1 so that a first difference DW1 (DW1=PG1−PW) between the first probability guess PG1 and the probability PW of the event for said each stop of the moving window MW is obtained. In the step ST4, a first comparison is performed to determine whether an absolute value of the first difference DW1 for each stop of the moving window MW is less than or equal to a preset threshold error. If any one of the absolute values of all the first differences DW1s is greater than the preset threshold error, the step ST5 continues. If the absolute values of all the first differences DW1s are less than or equal to the preset threshold error, the step ST11 continues. In the step ST5, a first error correction factor (ECF1) for each of the computation voxels is calculated by, e.g., summing error correction contributions from the stops of the moving window MW overlapping or covering said each of the computation voxels. For example, if there are four stops of the moving window MW overlapping or covering one of the computation voxels, each of the error correction contributions to said one of the computation voxels is calculated by obtaining an area ratio of an overlapped area between said one of the computation voxels and a corresponding one of the four stops to an area of the biggest square inscribed in the corresponding one of the four stops, and then multiplying the first difference DW1 for the corresponding one of the four stops by the area ratio. In the step ST6, a second probability PV2 for each of the computation voxels is calculated by subtracting the first error correction factor ECF1 for said each of the computation voxels from the first probability PV1 for said each of the computation voxels (PV2=PV1−ECF1). In the step ST7, a second probability guess PG2 for each stop of the moving window MW is calculated by averaging the second probabilities PV2s (obtained in the step ST6) of all the computation voxels inside said each stop of the moving widow MW. In the step ST8, the second probability guess PG2 for each stop of the moving window MW is compared with the probability PW of the event for said each stop of the moving window MW by, e.g., subtracting the probability PW of the event from the second probability guess PG2 so that a second difference DW2 (DW2=PG2−PW) between the second probability guess PG2 and the probability PW of the event for said each stop of the moving window MW is obtained. In the step S9, a second comparison is performed to determine whether an absolute value of the second difference DW2 for each stop of the moving window MW is less than or equal the preset threshold error. If any one of the absolute values of all the second differences DW2s is greater than the preset threshold error, the step ST10 continues. If the absolute values of all the second differences DW2s are less than or equal to the preset threshold error, the step ST11 continues. In the step ST10, the steps ST5-ST9 are repeated or iterated, using the newly obtained the $n^{th}$ difference DWn between the $n^{th}$ probability guess PGn and the probability PW of the event for each stop of the moving window MW for calculation in the $(n+1)^{th}$ iteration, until an absolute value of the $(n+1)^{th}$ difference DW(n+1) for each stop of the moving window MW is equal to or less than the preset threshold error (Note: PV1, PG1 and DW1 for the first iteration, ECF1, PV2, PG2 and DW2 for the second iteration, and ECF(n−1), PVn, PGn and DWn for the $n^{th}$ iteration). In the step ST11, the first probabilities PV1s in the first iteration, i.e., the steps ST1-ST4, the second probabilities PV2s in the second iteration, i.e., the steps ST5-ST9, or the $(n+1)^{th}$ probabilities PV(n+1)s in the $(n+1)^{th}$ iteration, i.e., the step ST10, are used to form the probability map. The probabilities of the event for the computation voxels are obtained using the above method, procedure or algorithm, based on the overlapped stops of the moving window MW, to form the probability map of the event for the image (e.g., patient's MRI slice) for the patient having imaging information (e.g., molecular imaging information). The above process is performed to generate the moving window MW across the image in the x and y directions to create a two-dimensional (2D) probability map. In order to obtain a three-dimensional (3D) probability map, the above process may be applied to each of all images of the patient in the z direction perpendicular to the x and y directions.

Description of Subset Data DB-1:

Referring to FIGS. 1B-1G, the tissue-based or biopsy-based subset data DB-1 from the big data database 70 includes multiple data sets each listed in the corresponding one of its rows 2 through N, wherein the number of the data sets may be greater than 100, 1,000 or 10,000. Each of the data sets in the subset data DB-1 may include: (1) measures for MRI parameters associated with a prostate biopsy tissue (i.e., biopsied sample of the prostate) obtained from a subject (e.g., human), as shown in columns A-O; (2) measures for processed parameters associated with the prostate biopsy tissue, as shown in columns P and Q; (3) a result or pathologist diagnosis of the prostate biopsy tissue, such as prostate cancer, normal tissue, or benign condition, as shown in a column R; (4) sample characters associated with the prostate biopsy tissue, as shown in columns S-X; (5) MRI characters associated with MRI slices registered to respective regions, portions, locations or volumes of the prostate biopsy tissue, as shown in columns Y, Z and AA; (6) clinical or pathology parameters associated with the prostate biopsy tissue or the subject, as shown in columns AB-AN; and (7) personal information associated with the subject, as shown in columns AO-AR. Needles used to obtain the prostate biopsy tissues may have the same cross-sectional shape (e.g., round shape or square shape) and the same inner diameter or width, e.g., ranging from, equal to or greater than 0.1 millimeters up to, equal to or less than 5 millimeters, and more preferably ranging from, equal to or greater than 1 millimeter up to, equal to or less than 3 millimeters.

The MRI parameters in the columns A-O of the subset data DB-1 are T1 mapping, T2 raw signal, T2 mapping, delta Ktrans (Δ Ktrans), tau, Dt IVIM, fp IVIM, ADC (high b-values), nADC (high b-values), R*, Ktrans from Tofts Model (TM), Ktrans from Extended Tofts Model (ETM), Ktrans from Shutterspeed Model (SSM), Ve from TM, and Ve from SSM. For more information about the MRI parameters in the subset data DB-1, please refer to FIGS. 20A through 20H. The processed parameter in the column P of the subset data DB-1 is average Ve, obtained by averaging Ve from TM and Ve from SSM. The processed parameter in the column Q of the subset data DB-1 is average Ktrans, obtained by averaging Ktrans from TM, Ktrans from ETM, and Ktrans from SSM. All data can have normalized values, such as z scores.

Measures in the respective columns T, U and V of the subset data DB-1 are Gleason scores associated with the respective prostate biopsy tissues and primary and secondary Gleason grades associated with the Gleason scores; FIG. 20L briefly explains Gleason score, the primary Gleason grade, and the secondary Gleason grade. Measures in the column W of the subset data DB-1 may be the diameters of the prostate biopsy tissues, and the diameter of each of the prostate biopsy tissues may be substantially equal to an inner diameter of a cylinder needle, through which a circular or round hole passes for receiving said each of the prostate biopsy tissues. Alternatively, measures in the column W of the subset data DB-1 may be the widths of the prostate biopsy tissues, and the width of each of the prostate biopsy tissues may be substantially equal to an inner width of a needle, through which a square or rectangular hole passes for receiving said each of the prostate biopsy tissues. The clinical or pathology parameters in the columns AB-AN of the subset data DB-1 are prostate specific antigen (PSA), PSA velocity, % free PSA, Histology subtype, location within a given anatomical structure of gland, tumor size, PRADS, pathological diagnosis (e.g., Atypia, benign prostatic hypertrophy (BPH), prostatic intraepithelial neoplasia (PIN), or Atrophy), pimonidazole immunoscore (hypoxia marker), pimonidazole genescore (hypoxia marker), primary tumor (T), regional lymph nodes (N), and distant metastasis (M). For more information about the clinical or pathology parameters in the subset data DB-1, please refer to FIGS. 20M through 20O. Other data or information in the big data database 70 may be added to the subset data DB-1. For example, each of the data sets in the subset data DB-1 may further include risk factors for cancer associated with the subject, such as smoking history, sun exposure, premalignant lesions, gene information or data, etc. Each of the data sets in the subset data DB-1 may also include imaging protocol details, such as MRI magnet strength, and pulse sequence parameters, and/or information regarding (preoperative) radiation therapy, including the type of radiation, the strength of radiation, the total dose of radiation, the number of fractions (depending on the type of cancer being treated), the duration of the fraction from start to finish, the dose of the fraction, the duration of the preoperative radiation therapy from start to finish, and the type of machine used for the preoperative radiation therapy. A post-therapy data or information for prostate cancer may also be included in the subset data DB-1. For example, data regarding ablative minimally invasive techniques or radiation treatments (care for early prostate cancer or post surgery), imaging data or information following treatment, and biopsy results following treatment are included in the subset data DB-1.

Referring to FIGS. 1D and 1E, data in the column W of the subset data DB-1 are various diameters; data in the column X of the subset data DB-1 are various lengths; data in the column Y of the subset data DB-1 are the various numbers of MRI slices registered to respective regions, portions, locations or volumes of a prostate biopsy tissue; data in the column Z of the subset data DB-1 are various MRI area resolutions; data in the column AA of the subset data DB-1 are various MRI slice thicknesses. Alternatively, the diameters of all the prostate biopsy tissues in the column W of the subset data DB-1 may be the same; the lengths of all the prostate biopsy tissues in the column X of the subset data DB-1 may be the same; all the data in the column Y of the subset data DB-1 may be the same; all the data in the column Z of the subset data DB-1 may be the same; all the data in the column AA of the subset data DB-1 may be the same.

Description of Subset Data DB-2:

Referring to FIGS. 1H-1M, the tissue-based or biopsy-based subset data DB-2 from the big data database 70 includes multiple data sets each listed in the corresponding one of its rows 2 through N, wherein the number of the data sets may be greater than 100, 1,000 or 10,000. Each of the data sets in the subset data DB-2 may include: (1) measures for MRI parameters associated with a breast biopsy tissue (i.e., biopsied sample of the breast) obtained from a subject (e.g., human or animal model), as shown in columns A-O, R, and S; (2) measures for processed parameters associated with the breast biopsy tissue, as shown in columns P and Q; (3) features of breast tumors associated with the breast biopsy tissue, as shown in columns T-Z; (4) a result or pathologist diagnosis of the breast biopsy tissue, such as breast cancer, normal tissue, or benign condition, as shown in a column AA; (5) sample characters associated with the breast biopsy tissue, as shown in columns AB-AD; (6) MRI characters associated with MRI slices registered to respective regions, portions, locations or volumes of the breast biopsy tissue, as shown in columns AE-AG; (7) a PET parameter (e.g., maximum standardized uptake value (SUVmax) depicted in FIG. 20I) associated with the breast biopsy tissue or the subject, as shown in a column AH; (8) clinical or pathology parameters associated with the breast biopsy tissue or the subject, as shown in columns AI-AT; and (9) personal information associated with the subject, as shown in columns AU-AX. Needles used to obtain the breast biopsy tissues may have the same cross-sectional shape (e.g., round shape or square shape) and the same inner diameter or width, e.g., ranging from, equal to or greater than 0.1 millimeters up to, equal to or less than 5 millimeters, and more preferably ranging from, equal to or greater than 1 millimeter up to, equal to or less than 3 millimeters. Alternatively, an intra-operative incisional biopsy tissue sampling may be performed by a surgery to obtain the breast biopsy. Intraoperative magnetic resonance imaging (iMRI) may be used for obtaining a specific localization of the breast biopsy tissue to be biopsied during the surgery.

The MRI parameters in the columns A-O, R, and S of the subset data DB-2 are T1 mapping, T2 raw signal, T2 mapping, delta Ktrans (Δ Ktrans), tau, Dt IVIM, fp IVIM, ADC (high b-values), R*, Ktrans from Tofts Model (TM), Ktrans from Extended Tofts Model (ETM), Ktrans from Shutterspeed Model (SSM), Ve from TM, Ve from SSM, kep from Tofts Model (TM), kep from Shutterspeed Model (SSM), and mean diffusivity (MD) from diffusion tensor imaging (DTI). For more information about the MRI parameters in the subset data DB-2, please refer to FIGS. 20A through 20H. The processed parameter in the column P of the subset data DB-2 is average Ve, obtained by averaging Ve from TM and Ve from SSM. The processed parameter in the column Q of the subset data DB-2 is average Ktrans, obtained by averaging Ktrans from TM, Ktrans from ETM, and Ktrans from SSM. The features of breast tumors may be extracted from breast tumors with dynamic contrast-enhanced (DCE) MR image.

Measures in the column AC of the subset data DB-2 may be the diameters of the breast biopsy tissues, and the diameter of each of the breast biopsy tissues may be substantially equal to an inner diameter of a cylinder needle, through which a circular or round hole passes for receiving said each of the breast biopsy tissues. Alternatively, the measures in the column AC of the subset data DB-2 may be the widths of the breast biopsy tissues, and the width of each of the breast biopsy tissues may be substantially equal to an inner width of a needle, through which a square or rectangular hole passes for receiving said each of the breast biopsy tissues. The clinical or pathology parameters in the columns AI-AT of the subset data DB-2 are estrogen hormone receptor positive (ER+), progesterone hormone receptor positive (PR+), HER2/neu hormone receptor positive (HER2/neu+), immunohistochemistry subtype, path, BIRADS, Oncotype DX score, primary tumor (T), regional lymph nodes (N), distant metastasis (M), tumor size, and location. For more information about the clinical or pathology parameters in the subset data DB-2, please refer to FIGS. 20P through 20R. Other data or information in the big data database 70 may be added to the subset data DB-2. For example, each of the data sets in the subset data DB-2 may further include specific long chain mRNA biomarkers from next generation sequencing that are predictive of metastasis-free survival, such as HOTAIR, RP11-278 L15.2-001, LINC00511-009, and AC004231.2-001. Each of the data sets in the subset data DB-2 may also include risk factors for cancer associated with the subject, such as smoking history, sun exposure, premalignant lesions, gene information or data, etc. Each of the data sets in the subset data DB-2 may also include imaging protocol details, such as MRI magnet strength, pulse sequence parameters, PET dosing, time at PET imaging, etc.

Referring to FIG. 1K, data in the column AC of the subset data DB-2 are various diameters; data in the column AD of the subset data DB-2 are various lengths; data in the column AE of the subset data DB-2 are the various numbers of MRI slices registered to respective regions, portions, locations or volumes of a breast biopsy tissue; data in the column AF of the subset data DB-2 are various MRI area resolutions; data in the column AG of the subset data DB-2 are various MRI slice thicknesses. Alternatively, the diameters of all the breast biopsy tissues in the column AC of the subset data DB-2 may be the same; the lengths of all the breast biopsy tissues in the column AD of the subset data DB-2 may be the same; all the data in the column AE of the subset data DB-2 may be the same; all the data in the column AF of the data DB-2 may be the same; all the data in the column AG of the subset data DB-2 may be the same.

A similar subset data like the subset data DB-1 or DB-2 may be established from the big data database 70 for generating probability maps for brain cancer, liver cancer, lung cancer, rectal cancer, sarcomas, cervical cancer, or cancer metastasis to any organ such as liver, bone, and brain. In this case, the subset data may include multiple data sets, each of which may include: (1) measures for MRI parameters (e.g., those in the columns A-O, R, and S of the subset data DB-2) associated with a biopsy tissue (e.g., biopsied brain sample, biopsied liver sample, biopsied lung sample, biopsied rectal sample, biopsied sarcomas sample, or biopsied cervix sample) obtained from a subject (e.g., human); (2) processed parameters (e.g., those in the columns P and Q of the subset data DB-2) associated with the biopsy tissue; (3) a result or pathologist diagnosis of the biopsy tissue, such as cancer, normal tissue, or benign condition; (4) sample characters (e.g., those in the columns S-X of the subset data DB-1) associated with the biopsy tissue; (5) MRI characters (e.g., those in the columns Y, Z and AA of the subset data DB-1) associated with MRI slices registered to respective regions, portions, locations or volumes of the biopsy tissue; (6) a PET parameter (e.g., SUVmax depicted in FIG. 20I) associated with the biopsy tissue or the subject; (7) CT parameters (e.g., HU and Hetwave) associated with the biopsy tissue or the subject; (8) clinical or pathology parameters (e.g., those in the columns AB-AN of the subset data DB-1 or the columns AI-AT of the subset data DB-2) associated with the biopsy tissue or the subject; and (9) personal information (e.g., those in the columns AO-AR of the subset data DB-1) associated with the subject.

Figure 2B:
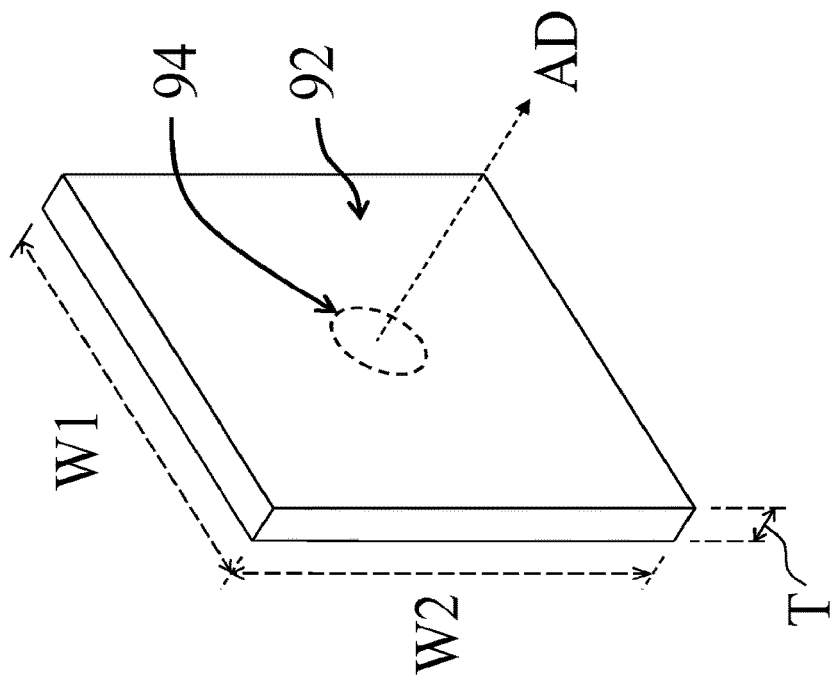
FIG. 2B is a schematic drawing of a MRI slice in accordance with an embodiment of the present invention.
Figure 2A:
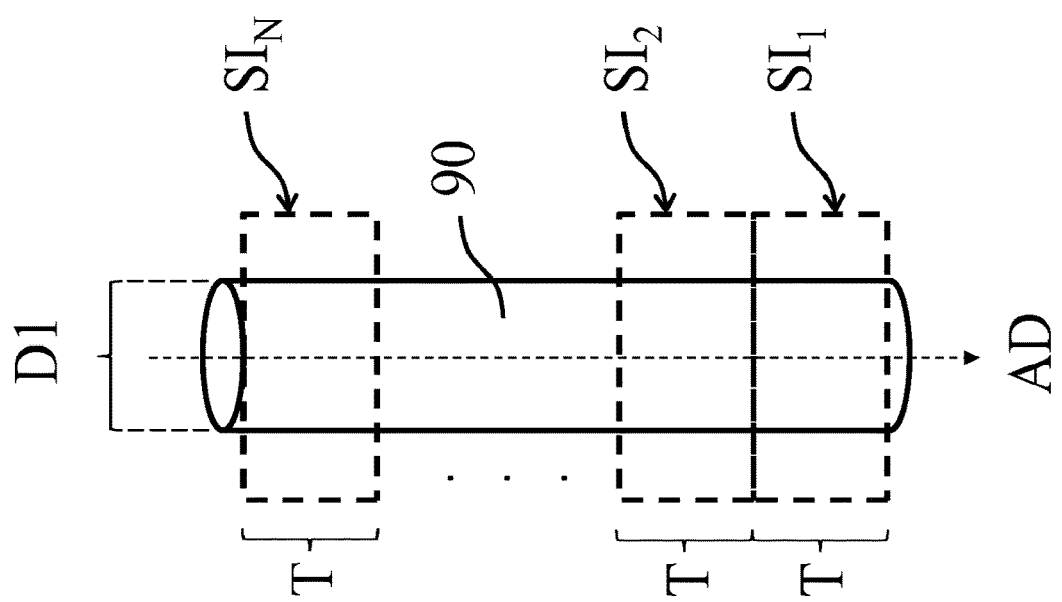
FIG. 2A is a schematic drawing showing a biopsy tissue and multiple MRI slices registered to the biopsy tissue in accordance with an embodiment of the present invention.

Description of Biopsy Tissue, MRI Slices Registered to the Biopsy Tissue, and MRI Parameters for the Biopsy Tissue:

Referring to FIG. 2A, a biopsy tissue or sample 90, such as any one of the biopsied tissues provided for the pathologist diagnosis depicted in the big data database 70, any one of the prostate biopsy tissues provided for the pathologist diagnosis depicted in the subset data DB-1, or any one of the breast biopsy tissues provided for the pathologist diagnosis depicted in the subset data DB-2, may be obtained from a subject (e.g., human) by core needle biopsy, such as MRI-guided needle biopsy. Alternatively, an intra-operative incisional biopsy tissue sampling may be performed by a surgery to obtain the biopsy tissue 90 from the subject. One or more fiducial markers that could be seen on subsequent imaging may be placed during the surgery to match tissues or identify positions of various portions of an organ with respect to the one or more fiducial markers. The fiducial marker is an object placed in the field of view of an imaging system which appears in the image produced, for use as a point of reference or a measure.

The core needle biopsy is a procedure used to determine whether an abnormality or a suspicious area of an organ (e.g., prostate or breast) is a cancer, a normal tissue, or a benign condition or to determine any other tissue characteristic such as mRNA expression, receptor status, and molecular tissue characteristics. With regard to MRI-guided needle biopsy, magnetic resonance (MR) imaging may be used to guide a cylinder needle to the abnormality or the suspicious area so that a piece of tissue, such as the biopsy tissue 90, is removed from the abnormality or the suspicious area by the cylinder needle, and the removed tissue is then sent to be examined by pathology.

During or before the core needle biopsy (e.g., MRI-guided needle biopsy), parallel MRI slices $SI_1$ through $SI_N$ registered to multiple respective regions, portions, locations or volumes of the tissue 90 may be obtained. The number of the registered MRI slices $SI_1$-$SI_N$ may range from, equal to or greater than 2 up to, equal to or less than 10. The registered MRI slices $SI_1$-$SI_N$ may have the same slice thickness T, e.g., ranging from, equal to or greater than 1 millimeter up to, equal to or less than 10 millimeters, and more preferably ranging from, equal to or greater than 3 millimeters up to, equal to or less than 5 millimeters.

Figure 2C:
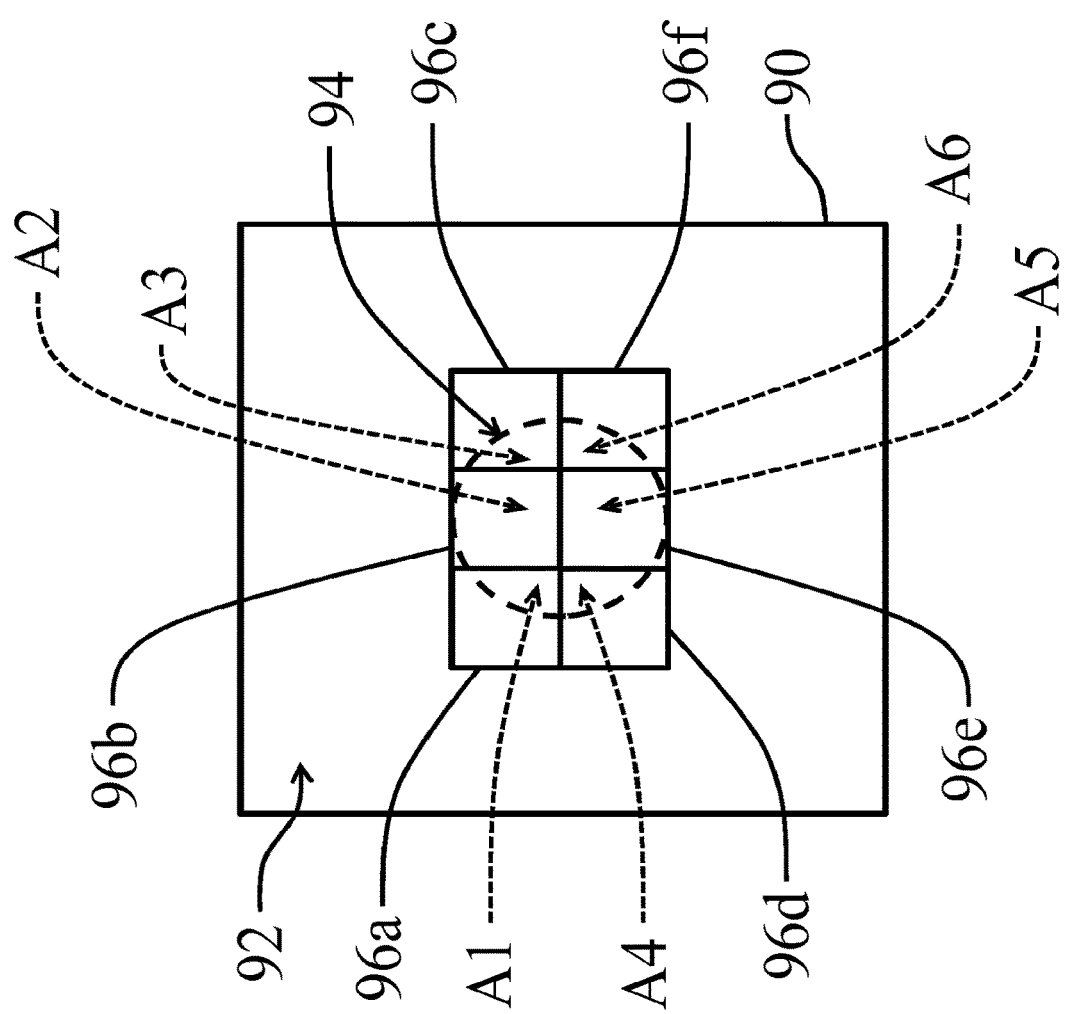
FIG. 2C is a schematic drawing showing multiple voxels of a MRI slice covered by a region of interest (ROI) on the MRI slice in accordance with an embodiment of the present invention.
Figure 2E:
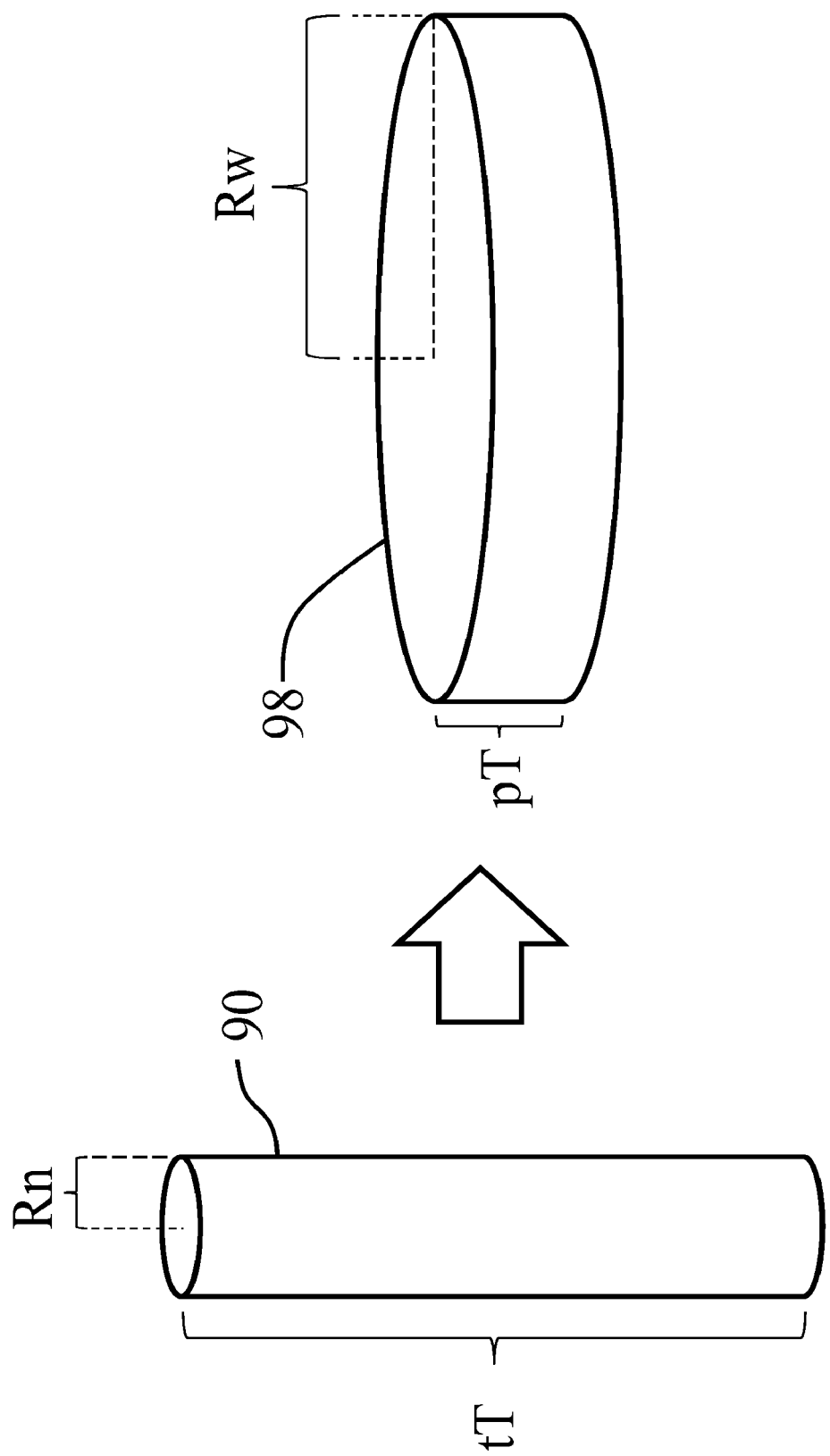
FIG. 2E shows a planar cylinder transformed from a long cylinder of a biopsied tissue in accordance with an embodiment of the present invention.

Referring to FIGS. 2A and 2E, the biopsy tissue 90 obtained from the subject by the cylinder needle may be long cylinder-shaped with a height tT normalized to the slice thickness T and with a circular cross section perpendicular to its axial direction AD, and the circular cross section of the biopsy tissue 90 may have a diameter D1, perpendicular to its height tT extending along the axial direction AD, ranging from, equal to or greater than 0.5 millimeters up to, equal to or less than 4 millimeters. The diameter D1 of the biopsy tissue 90 may be substantially equal to an inner diameter of the cylinder needle, through which a circular or round hole passes for receiving the biopsy tissue 90. The axial direction AD of the tissue 90 to be biopsied may be parallel with the slice thickness direction of each of the MRI slices $SI_1$-$SI_N$. As shown in FIG. 2B, each of the MRI slices $SI_1$-$SI_N$ may have an imaging plane 92 perpendicular to the axial direction AD of the tissue 90 to be biopsied, wherein an area of the imaging plane 92 is a side length W1 multiplied by another side length W2. The MRI slices $SI_1$-$SI_N$ may have the same area resolution, which is a field of view (FOV) of one of the MRI slices $SI_1$-$SI_N$ (i.e., the area of its imaging plane 92) divided by the number of all voxels in the imaging plane 92 of said one of the MRI slices $SI_1$-$SI_N$.

Regions, i.e., portions, locations or volumes, of interest (ROIs) 94 of the respective MRI slices $SI_1$-$SI_N$ are registered to and aligned with the respective regions, portions, locations or volumes of the biopsy tissue 90 to determine or calculate measures of MRI parameters for the regions, portions, locations or volumes of the biopsy tissue 90. The ROIs 94 of the MRI slices $SI_1$-$SI_N$ may have the same diameter, substantially equal to the diameter D1 of the biopsy tissue 90, i.e., the inner diameter of the needle for taking the biopsy tissue 90, and may have a total volume covering and substantially equaling the volume of the biopsy tissue 90. As shown in FIG. 2C, the ROI 94 of each of the MRI slices $SI_1$-$SI_N$ may cover or overlap multiple voxels, e.g., 96a through 96f. A MRI parameter (e.g., T1 mapping) for the ROI 94 of each of the MRI slices $SI_1$-$SI_N$ may be measured by summing values of the MRI parameter for the voxels 96a-96f in said each of the MRI slices $SI_1$-$SI_N$ weighed or multiplied by the respective percentages of areas A1, A2, A3, A4, A5 and A6, overlapping with the respective voxels 96a-96f in the ROI 94 of said each of the MRI slices $SI_1$-$SI_N$, occupying the ROI 94 of said each of the MRI slices $SI_1$-$SI_N$. Accordingly, the MRI parameter for the whole biopsy tissue 90 may be measured by dividing the sum of measures for the MRI parameter for the ROIs 94 of the MRI slices $SI_1$-$SI_N$ by the number of the MRI slices $SI_1$-$SI_N$. By this way, other MRI parameters (e.g., those in the columns B-O of the subset data DB-1 or those in the columns B-O, R and S of the subset data DB-2) for the whole biopsy tissue 90 are measured. The measures for the various MRI parameters (e.g., T1 mapping, T2 raw signal, T2 mapping, etc.) for the ROI 94 of each of the MRI slices $SI_1$-$SI_N$ may be derived from different parameter maps registered to the corresponding region, portion, location or volume of the biopsy tissue 90. In an alternative example, the measures for some of the MRI parameters for the ROT 94 of each of the MRI slices $SI_1$-$SI_N$ may be derived from different parameter maps registered to the corresponding region, portion, location or volume of the biopsy tissue 90, and the measures for the others may be derived from the same parameter map registered to the corresponding region, portion, location or volume of the biopsy tissue 90. The aforementioned method for measuring the MRI parameters for the whole biopsy tissue 90 can be applied to each of the MRI parameters in the big data database 70 and the subset data DB-1 and DB-2.

Taking an example of T1 mapping, in the case of (1) four MRI slices $SI_1$-$SI_4$ having four respective regions, portions, locations or volumes registered to respective quarters of the biopsy tissue 90 and (2) the ROI 94 of each of the MRI slices $SI_1$-$SI_4$ covering or overlapping the six voxels 96a-96f, values of T1 mapping for the voxels 96a-96f in each of the MRI slices $SI_1$-$SI_4$ and the percentages of the areas A1-A6 occupying the ROT 94 of each of the MRI slices $SI_1$-$SI_4$ are assumed as shown in FIG. 2D. A measure of T1 mapping for the ROI 94 of the MRI slice $SI_1$, i.e., 1010.64, may be obtained or calculated by summing (1) the value, i.e., 1010, for the voxel 96a multiplied by the percentage, i.e., 6%, of the area A1, overlapping with the voxel 96a in the ROI 94 of the MRI slice $SI_1$, occupying the ROI 94 of the MRI slice $SI_1$, (2) the value, i.e., 1000, for the voxel 96b multiplied by the percentage, i.e., 38%, of the area A2, overlapping with the voxel 96b in the ROI 94 of the MRI slice $SI_1$, occupying the ROT 94 of the MRI slice $SI_1$, (3) the value, i.e., 1005, for the voxel 96c multiplied by the percentage, i.e., 6%, of the area A3, overlapping with the voxel 96c in the ROI 94 of the MRI slice $SI_1$, occupying the ROI 94 of the MRI slice $SI_1$, (4) the value, i.e., 1020, for the voxel 96d multiplied by the percentage, i.e., 6%, of the area A4, overlapping with the voxel 96d in the ROI 94 of the MRI slice $SI_1$, occupying the ROI 94 of the MRI slice $SI_1$, (5) the value, i.e., 1019, for the voxel 96e multiplied by the percentage, i.e., 38%, of the area A5, overlapping with the voxel 96e in the ROT 94 of the MRI slice $SI_1$, occupying the ROI 94 of the MRI slice $SI_1$, and (6) the value, i.e., 1022, for the voxel 96f multiplied by the percentage, i.e., 6%, of the area A6, overlapping with the voxel 96f in the ROI 94 of the MRI slice $SI_1$, occupying the ROI 94 of the MRI slice $SI_1$. By this way, T1 mapping for the ROIs 94 of the MRI slices $SI_2$, $SI_3$, and $SI_4$, i.e., 1006.94, 1022, and 1015.4, are obtained or measured. Accordingly, T1 mapping for the whole biopsy tissue 90, i.e., 1013.745, is obtained or measured by dividing the sum, i.e., 4054.98, of T1 mapping for the ROIs 94 of the MRI slices $SI_1$-$SI_4$ by the number of the MRI slices $SI_1$-$SI_4$, i.e., 4.

The volume of the long cylinder-shaped biopsied tissue 90 may be transformed into another shape, which may have a volume the same or about the same as the volume of the long cylinder-shaped biopsied tissue 90 (or Volume of Interest (VOI), which may be $\pi \times Rn^2 \times tT$, where Rn is the radius of the biopsied tissue 90, and tT is the height of the biopsied tissue 90), for easy or meaningful computing purposes, for medical instrumentation purposes, or for clearer final data presentation purposes. For example, referring to FIG. 2E, the long cylinder of the biopsied tissue 90 with the radius Rn and height tT may be transformed into a planar cylinder 98 to match the slice thickness T. The planar cylinder 98, having a volume, e.g., the same or about the same as the VOI of the biopsied tissue 90, may be defined by the following formula: $\pi \times Rn^2 \times M \times St = \pi \times Rw^2 \times pT$, where Rn is the radius of the biopsy tissue 90 (which is substantially equal to the inner radius of the needle for taking the biopsy tissue 90), M is the number of the MRI slices $SI_1$-$SI_N$, St is the slice thickness T of the MRI slices $SI_1$-$SI_N$, Rw is the radius of the planar cylinder 98, and pT is the height or thickness of the planar cylinder 98 perpendicular to the radius Rw of the planar cylinder 98. The height tT of the biopsy tissue 90 may be substantially equal to the slice thickness T multiplied by the number of the MRI slices $SI_1$-$SI_N$. In the invention, the height pT of the planar cylinder 98 is substantially equal to the slice thickness T, for example. Accordingly, the planar cylinder 98 may have the height pT equal to the slice thickness T and the radius Rw equal to the radius Rn multiplied by the square root of the number of the registered MRI slices $SI_1$-$SI_N$. The radius Rw of the planner cylinder 98 may be used to define the radius Rm of a moving window MW in calculating probability maps, e.g., illustrated in first through sixth embodiments, for a patient (e.g., human). Each of the biopsy tissue 90, the planar cylinder 98 and the moving window MW may have a volume at least 2, 3, 5, 10 or 15 times greater than that of each voxel of the MRI slices $SI_1$-$SI_N$ and than that of each voxel of an MRI image 10 from a subject (e.g., patient) depicted in a step S1 of FIG. 4. In addition, because the planar cylinder 98 is transformed from the biopsy tissue 90, the measures of the MRI parameters for the whole biopsy tissue 90 may be considered as those for the planar cylinder 98.

Further, each of biopsy tissues provided for pathologist diagnoses in a subset data, e.g., DB-1 or DB-2, of the big data database 70 may have a corresponding planar cylinder 98 with its radius Rw, and data (such as pathologist diagnosis and measures of imaging parameters) for said each of the biopsy tissues in the subset data, e.g., DB-1 or DB-2, of the big data database 70 may be considered as those for the corresponding planar cylinder 98. Statistically, the moving window MW may be determined with the radius Rm, perpendicular to a thickness of the moving window MW, based on the statistical distribution or average of the radii Rw of the planar cylinders 98 transformed from the volumes of the biopsy tissues provided for the pathologist diagnoses in the subset data, e.g., DB-1 or DB-2, of the big data database 70. In the invention, each of the biopsy tissues provided for the pathologist diagnoses in the subset data, e.g., DB-1 or DB-2, of the big data database 70, for example, may have a volume, i.e., VOI, substantially equal to the volume of the moving window MW to be used in calculating one or more probability maps. In other words, the volume of the biopsy tissue, i.e., VOI, defines the size (e.g., the radius Rm) of the moving window MW to be used in calculating one or more probability maps.

Each of the prostate biopsy tissues provided for the pathologist diagnoses in the subset data DB-1 may be referred to the illustration of the biopsy tissue 90. In the column W of the subset data DB-1, the diameter of each of the prostate biopsy tissues may be referred to the illustration of the diameter D1 of the biopsy tissue 90. The MRI slices registered to the respective regions, portions, locations or volumes of each of the prostate biopsy tissues provided for the pathologist diagnoses in the subset data DB-1 may be referred to the illustration of the MRI slices $SI_1$-$SI_N$ registered to the respective regions, portions, locations or volumes of the biopsy tissue 90. The measures of the MRI parameters for each of the prostate biopsy tissues, i.e., for each of the corresponding planar cylinders 98, in the respective columns A-O of the subset data DB-1 may be calculated as the measures of the MRI parameters for the whole biopsy tissue 90, i.e., for the planar cylinder 98 transformed from the volume of the biopsy tissue 90, are calculated. In the column Z of the subset data DB-1, the MRI slices registered to the respective regions, portions, locations or volumes of each of the prostate biopsy tissues may have the same area resolution, which may be referred to the illustration of the area resolution of the MRI slices $SI_1$-$SI_N$ registered to the respective regions, portions, locations or volumes of the biopsy tissue 90. In the column AA of the subset data DB-1, the MRI slices registered to the respective regions, portions, locations or volumes of each of the prostate biopsy tissues may have the same slice thickness, which may be referred to the illustration of the slice thickness T of the MRI slices $SI_1$-$SI_N$.

In the column S of the subset data DB-1, the percentage of cancer for the whole volume of the prostate biopsy tissue in each of all or some of the data sets may be replaced by the percentage of cancer for a partial volume of the prostate biopsy tissue; a MRI slice is imaged for and registered to the partial volume of the prostate biopsy tissue. In this case, the MRI parameters, in the columns A-O of the subset data DB-1, that are in said each of all or some of the data sets are measured for a ROT of the MRI slice registered to the partial volume of the prostate biopsy tissue. The ROI of the MRI slice covers or overlaps multiple voxels in the MRI slice, and each of the MRI parameters for the ROI of the MRI slice may be measured by summing values of said each of the MRI parameters for the voxels weighed or multiplied by respective percentages of areas, overlapping with the respective voxels in the ROI of the MRI slice, occupying the ROT of the MRI slice. Measures for the MRI parameters for the ROI of the MRI slice may be derived from different parameter maps registered to the partial volume of the prostate biopsy tissue. In an alternative example, the measures for some of the MRI parameters for the ROI of the MRI slice may be derived from different parameter maps registered to the partial volume of the prostate biopsy tissue, and the measures for the others may be derived from the same parameter map registered to the partial volume of the prostate biopsy tissue.

Each of the breast biopsy tissues provided for the pathologist diagnoses in the subset data DB-2 may be referred to the illustration of the biopsy tissue 90. In the column AC of the subset data DB-2, the diameter of each of the breast biopsy tissues may be referred to the illustration of the diameter D1 of the biopsy tissue 90. The MRI slices registered to the respective regions, portions, locations or volumes of each of the breast biopsy tissues provided for the pathologist diagnoses in the subset data DB-2 may be referred to the illustration of the MRI slices $SI_1$-$SI_N$ registered to the respective regions, portions, locations or volumes of the biopsy tissue 90. The measures of the MRI parameters for each of the breast biopsy tissues, i.e., for each of the corresponding planar cylinders 98, in the respective columns A-O, R, and S of the subset data DB-2 may be calculated as the measures of the MRI parameters for the whole biopsy tissue 90, i.e., for the planar cylinder 98 transformed from the volume of the biopsy tissue 90, are calculated. In the column AF of the subset data DB-2, the MRI slices registered to the respective regions, portions, locations or volumes of each of the breast biopsy tissues may have the same area resolution, which may be referred to the illustration of the area resolution of the MRI slices $SI_1$-$SI_N$ registered to the respective regions, portions, locations or volumes of the biopsy tissue 90. In the column AG of the subset data DB-2, the MRI slices registered to the respective regions, portions, locations or volumes of each of the breast biopsy tissues may have the same slice thickness, which may be referred to the illustration of the slice thickness T of the MRI slices $SI_1$-$SI_N$.

In the column AB of the subset data DB-2, the percentage of cancer for the whole volume of the breast biopsy tissue in each of all or some of the data sets may be replaced by the percentage of cancer for a partial volume of the breast biopsy tissue; a MRI slice is imaged for and registered to the partial volume of the breast biopsy tissue. In this case, the MRI parameters, in the columns A-O, R, and S of the subset data DB-2, that are in said each of all or some of the data sets are measured for a ROI of the MRI slice registered to the partial volume of the breast biopsy tissue. The ROI of the MRI slice covers or overlaps multiple voxels in the MRI slice, and each of the MRI parameters for the ROI of the MRI slice may be measured by summing values of said each of the MRI parameters for the voxels weighed or multiplied by respective percentages of areas, overlapping with the respective voxels in the ROT of the MRI slice, occupying the ROI of the MRI slice. Measures for the MRI parameters for the ROI of the MRI slice may be derived from different parameter maps registered to the partial volume of the breast biopsy tissue. In an alternative example, the measures for some of the MRI parameters for the ROI of the MRI slice may be derived from different parameter maps registered to the partial volume of the breast biopsy tissue, and the measures for the others may be derived from the same parameter map registered to the partial volume of the breast biopsy tissue.

In an alternative example, the biopsied tissue 90 may be obtained by a needle with a square through hole therein. In this case, the biopsied tissue 90 may have a longitudinal shape with a square-shaped cross-section having a width Wb (which is substantially equal to an inner width of the needle, i.e., the width of the square through hole of the needle) and a height Ht (which is substantially equal to, e.g., the slice thickness T multiplied by the number of the MRI slices $SI_1$-$SI_N$). The volume of the biopsied tissue 90 may be transformed into a flat square FS with a width Wf and a thickness or height fT. The flat square FS, having a volume the same or about the same as the volume of the biopsied tissue 90 (or Volume of Interest (VOI), which may be the height Ht multiplied by the square of the width Wb), may be defined by the following formula: $Wb^2 \times M \times St = Wf^2 \times fT$, where Wb is the width of the biopsy tissue 90, M is the number of the MRI slices $SI_1$-$SI_N$, St is the slice thickness T of the MRI slices $SI_1$-$SI_N$, Wf is the width of the flat square FS, and IT is the height or thickness of the flat square FS perpendicular to the width Wf of the flat square FS. In the invention, the height or thickness fT of the flat square FS is substantially equal to the slice thickness T, for example. Accordingly, the flat square FS may have the height or thickness fT equal to the slice thickness T and the width Wf equal to the width Wb multiplied by the square root of the number of the registered MRI slices $SI_1$-$SI_N$. In the case of the moving window MW with a square shape, the width Wf of the flat square FS may be used to define the width of the moving window MW in calculating probability maps. Each of the biopsy tissue 90, the flat square FS and the square moving window MW may have a volume at least 2, 3, 5, 10 or 15 times greater than that of each voxel of the MRI slices $SI_1$-$SI_N$ and than that of each voxel of an MRI image, e.g., 10 from a subject (e.g., patient) depicted in a step S1 of FIG. 4. Further, each of biopsy tissues provided for pathologist diagnoses in a subset data of the big data database 70 may have a corresponding flat square FS with its width Wf, and data (such as pathologist diagnosis and measures of imaging parameters) for said each of the biopsy tissues in the subset data of the big data database 70 may be considered as those for the corresponding flat square FS.

Figure 5:
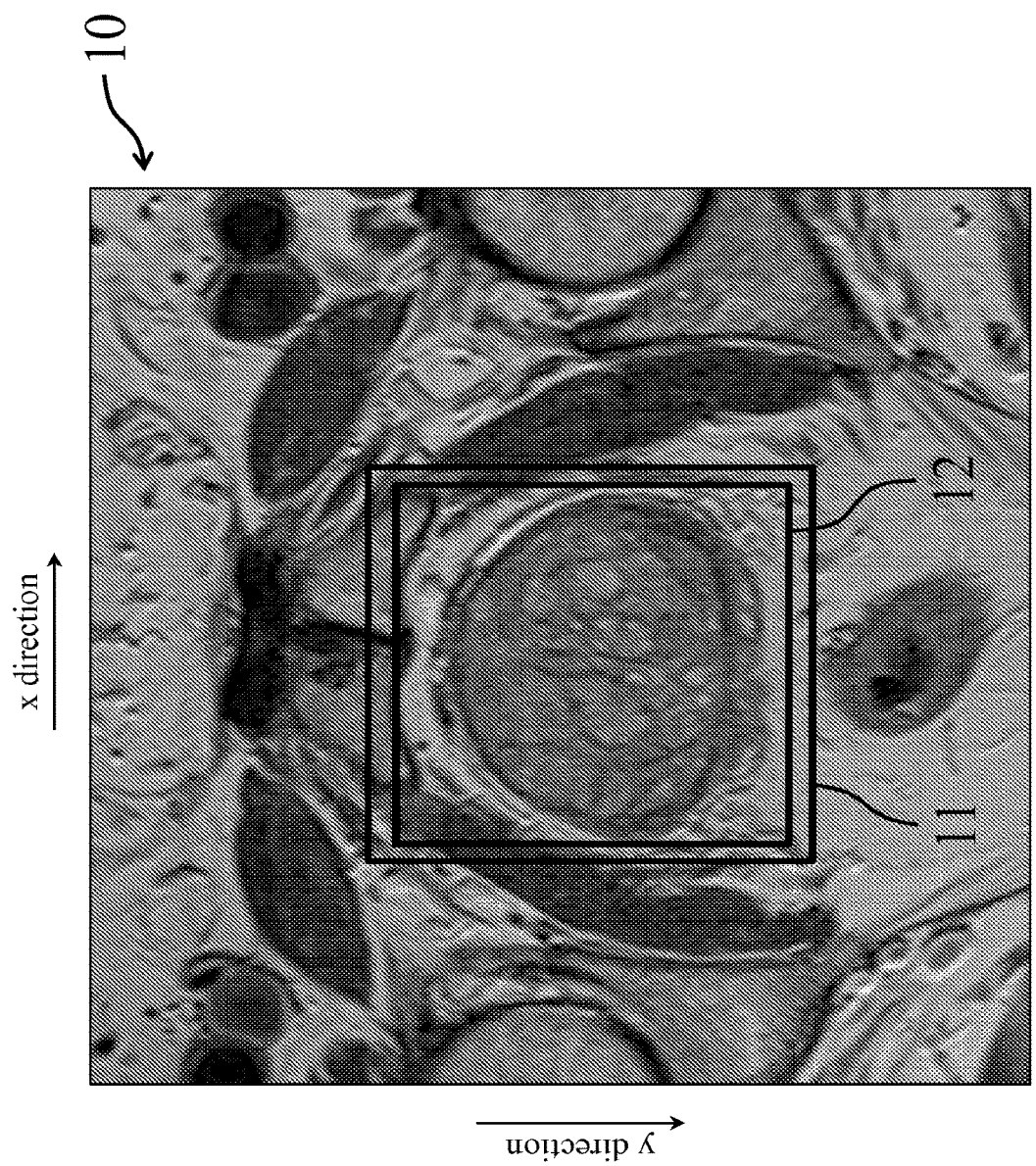
FIG. 5 shows a MRI slice showing a prostate, as well as a computation region on the MRI slice, in accordance with an embodiment of the present invention.
Figure 19:
FIG. 19 shows a MRI slice showing a breast, as well as a computation region on the MRI slice, in accordance with an embodiment of the present invention.

Description of Area Resolution and Voxels of a Single MRI Slice:

In the invention, an area resolution of a single MRI slice such as single slice MRI image 10 shown in FIG. 5 or 19 is a field of view (FOV) of the single MRI slice divided by the number of all voxels in the FOV of the single MRI slice. Each of the voxels of the single MRI slice may have a pixel (or pixel plane), perpendicular to the slice thickness direction of the single MRI slice, having a square area with the same four side lengths.

Description of Moving Window and Probability Map:

Any probability map in the invention may be composed of multiple computation voxels with the same size, which are basic units of the probability map. The size of the computation voxels used to compose the probability map may be defined based on the size of the moving window MW, which is determined or defined based on information data associated with the biopsy tissues provided for the pathologist diagnoses in the subset data, e.g., DB-1 or DB-2, of the big data database 70. The information data, for example, may include the radii Rw of planar cylinders 98 transformed from the volumes of the biopsy tissues. In addition, each of the computation voxels of the probability map may have a volume or size equal to, greater than or less than that of any voxel in a single MRI slice, such as MRI image 10 shown in FIG. 5 or 19, depicted in steps S1-S6 of FIG. 4.

The moving window MW may have various shapes, such as a circular shape, a square shape, a rectangular shape, a hexagonal shape, or an octagonal shape. In the invention, referring to FIG. 3A, the moving window MW is a circular moving window 2 with a radius Rm, for example. The radius Rm of the circular moving window 2 may be calculated, determined, or defined based on the statistical distribution or average of the radii Rw of planar cylinders 98 obtained from biopsy tissues associated with a subset data, e.g., DB-1 or DB-2, of the big data database 70. For example, in the first embodiment of the invention, the radius Rm of the circular moving window 2 may be calculated, determined or defined based on the statistical distribution or average of the radii Rw of the planar cylinders 98 obtained from the prostate biopsy tissues associated with the subset data DB-1; the approach to obtain the radius Rw of the planar cylinder 98 from the biopsy tissue 90 may be applied to obtain the radii Rw of the planar cylinders 98 from the prostate biopsy tissues associated with the subset data DB-1. In the third embodiment of the invention, the radius Rm of the circular moving window 2 may be calculated, determined or defined based on the statistical distribution or average of the radii Rw of the planar cylinders 98 obtained from the breast biopsy tissues associated with the subset data DB-2; the approach to obtain the radius Rw of the planar cylinder 98 from the biopsy tissue 90 may be applied to obtain the radii Rw of the planar cylinders 98 from the breast biopsy tissues associated with the subset data DB-2.

Figure 3C:
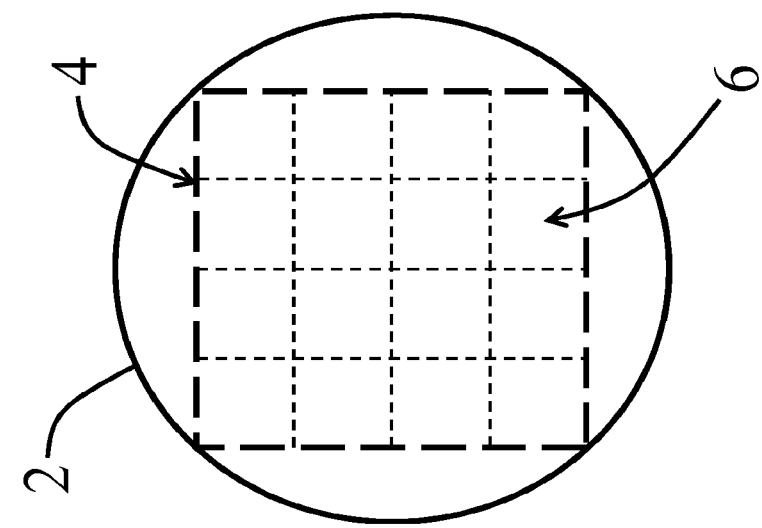
FIG. 3C is a schematic drawing showing a circular window and a four-by-four grid array within a square inscribed in the circular window in accordance with an embodiment of the present invention.
Figure 3B:
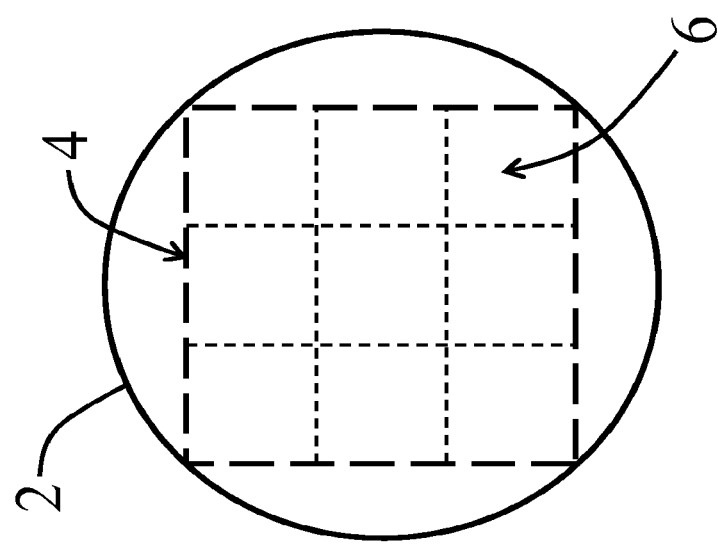
FIG. 3B is a schematic drawing showing a circular window and a three-by-three grid array within a square inscribed in the circular window in accordance with an embodiment of the present invention.
Figure 3A:
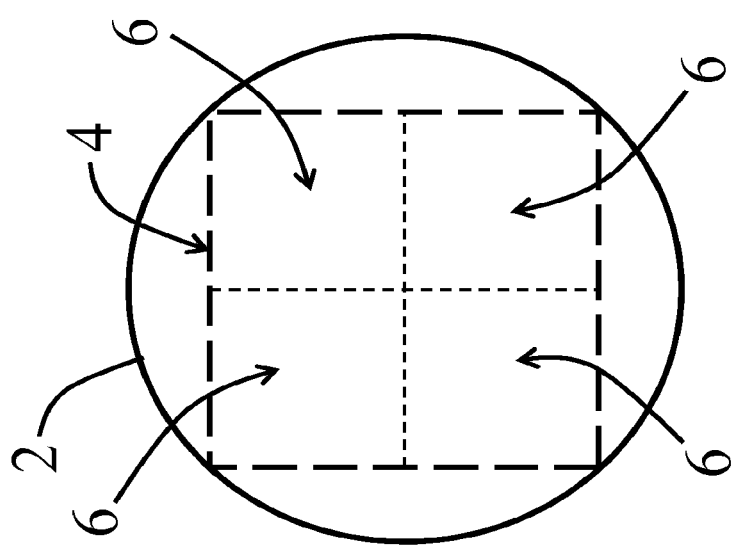
FIG. 3A is a schematic drawing showing a circular window and a two-by-two grid array within a square inscribed in the circular window in accordance with an embodiment of the present invention.

Referring to FIG. 3A, 3B or 3C, a square 4 having its four vertices lying on the circular moving window 2, i.e., the biggest square 4 inscribed in the circular moving window 2, is defined and divided into multiple small units or grids 6. The small grids 6 may be $n^2$ small squares each having a width Wsq, where n is an integer, such as 2, 3, 4, 5, 6, or more than 6. Based on the size (e.g., the width Wsq) and shape of the divided squares 6, the size and shape of the computation voxels used to compose the probability map may be defined. In other words, each of the computation voxels used to compose the probability map, for example, may be defined as a square with the width Wsq and a volume the same or about the same as that of each square 6 based on the radius Rm of the circular moving window 2 and the number of the squares 6 in the circular moving window 2, i.e., based on the width Wsq of the squares 6 in the circular moving window 2.

The circular moving window 2 in FIG. 3A is shown with a two-by-two square array in the square 4, each square 6 of which has the same area (i.e., a quarter of the square 4). In FIG. 3A, the four non-overlapped squares 6 have the same width Wsq, which is equal to the radius Rm of the circular moving window 2 divided by $\sqrt{2}$. In the case of the circular moving window 2 having the radius Rm of $\sqrt{2}$ millimeters, each square 6 may have an area of 1 millimeter by 1 millimeter, that is, each square 6 has the width Wsq of 1 millimeter.

In an alternative example, referring to FIG. 3B, the square 4 may have a three-by-three square array, each square 6 of which has the same area (i.e., a ninth of the square 4); the nine non-overlapped squares 6 have the same width Wsq, which is equal to the radius Rm of the circular moving window 2 divided by $\tfrac{2}{3}\sqrt{2}$. In an alternative example, referring to FIG. 3C, the square 4 may have a four-by-four square array, each square 6 of which has the same area (i.e., one sixteenth of the square 4); the sixteen non-overlapped squares 6 have the same width Wsq, which is equal to the radius Rm of the circular moving window 2 divided by $2\sqrt{2}$.

Figure 4:
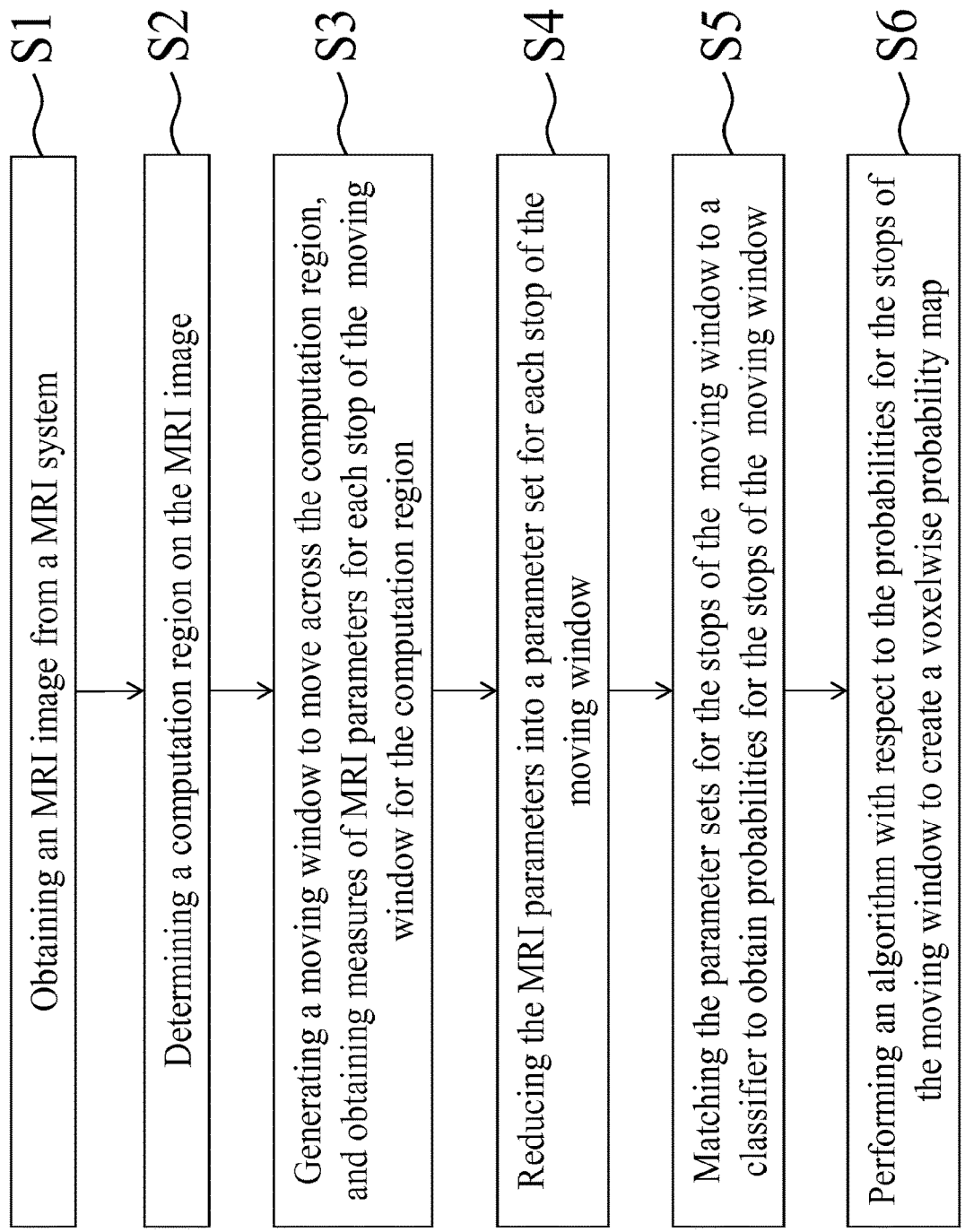
FIG. 4 is a flow chart illustrating a computing method of generating or forming a probability map in accordance with an embodiment of the present invention.

Accordingly, the moving window MW (e.g., the circular moving window 2) may be defined to include four or more non-overlapped grids 6 having the same square shape, the same size or area (e.g., 1 millimeter by 1 millimeter), and the same width Wsq, e.g., equal to, greater than or less than any side length of pixels of voxels in a single MRI slice, such as MRI image 10 shown in FIG. 5 or 19, depicted in the steps S1-S3 of FIG. 4. Each of the squares 6, for example, may have an area less than 25% of that of the moving window MW and equal to, greater than or less than that of the pixel of each voxel of the single MRI slice; each of the squares 6, for example, may have a volume equal to, greater than or less than that of each voxel of the single MRI slice. In the case of the moving window MW defined to include four or more non-overlapped squares 6 with the width Wsq, the moving window MW may move across the single MRI slice at a regular step or interval of a fixed distance of the width Wsq in the x and y directions so that the computation voxels of the probability map are defined. A stop of the moving window MW overlaps the neighboring stop of the moving window MW.

Alternatively, the grids 6 may be n rectangles each having a width Wrec and a length Lrec, where n is an integer, such as 2, 3, 4, 5, 6, 7, 8, or more than 8. Based on the size (e.g., the width Wrec and the length Lrec) and shape of the divided rectangles 6, the size and shape of the computation voxels used to compose the probability map may be defined. In other words, each of the computation voxels used to compose the probability map, for example, may be defined as a rectangle with the width Wrec, the length Lrec, and a volume the same or about the same as that of each rectangle 6 based on the radius Rm of the circular moving window 2 and the number of the rectangles 6 in the circular moving window 2, i.e., based on the width Wrec and length Lrec of the rectangles 6 in the circular moving window 2. Accordingly, the moving window MW (e.g., the circular moving window 2) may be defined to include four or more non-overlapped grids 6 having the same rectangle shape, the same size or area, the same width Wrec, e.g., equal to, greater than or less than any side length of pixels of voxels in a single MRI slice, such as MRI image 10 shown in FIG. 5 or 19, depicted in the steps S1-S3 of FIG. 4, and the same length Lrec, e.g., equal to, greater than or less than any side length of the pixels of the voxels in the single MRI slice. Each of the rectangles 6, for example, may have an area less than 25% of that of the moving window MW and equal to, greater than or less than that of the pixel of each voxel of the single MRI slice. Each of the rectangles 6, for example, may have a volume equal to, greater than or less than that of each voxel of the single MRI slice. In the case of the moving window MW defined to include four or more non-overlapped rectangles 6 with the width Wrec and the length Lrec, the moving window MW may move across the single MRI slice at a regular step or interval of a fixed distance of the width Wrec in the x direction and at a regular step or interval of a fixed distance of the length Lrec in the y direction so that the computation voxels of the probability map are defined. A stop of the moving window MW overlaps the neighboring stop of the moving window MW.

In the case of the moving window MW with a square shape, the square moving window MW may be determined with a width Wsm based on the statistical distribution or average of the widths Wf of flat squares FS obtained from biopsy tissues associated with a subset data of the big data database 70. The square moving window MW may be divided into the aforementioned small grids 6. In this case, each of the computation voxels of the probability map, for example, may be defined as a square with the width Wsq and a volume the same or about the same as that of each square 6 based on the width Wsm of the square moving window MW and the number of the squares 6 in the square moving window MW, i.e., based on the width Wsq of the squares 6 in the square moving window MW. Alternatively, each of the computation voxels of the probability map may be defined as a rectangle with the width Wrec, the length Lrec, and a volume the same or about the same as that of each rectangle 6 based on the width Wsm of the square moving window MW and the number of the rectangles 6 in the square moving window MW, i.e., based on the width Wrec and length Lrec of the rectangles 6 in the square moving window MW.

Description of Classifier CF:

The classifier CF for an event, such as biopsy-diagnosed tissue or tumor characteristic for, e.g., specific cancerous cells or occurrence of prostate cancer or breast cancer, may be created or established based on a subset (e.g., the subset data DB-1 or DB-2 or the aforementioned subset data established for generating the voxelwise probability map of brain cancer, liver cancer, lung cancer, rectal cancer, sarcomas, cervical cancer, or cancer metastasis to any organ such as liver, bone, and brain) obtained from the big data database 70. The subset may have all data associated with the given event from the big data database 70. The classifier CF may be a Bayesian classifier, which may be created by performing the following steps: constructing database, preprocessing parameters, ranking parameters, identifying a training dataset, and determining posterior probabilities for test data.

In the step of constructing database, a first group and a second group may be determined or selected from a tissue-based or biopsy-based subset data, such as the aforementioned subset data, e.g., DB-1 or DB-2, from the big data database 70, and various variables associated with each of the first and second groups are obtained from the tissue-based or biopsy-based subset data. The variables may be MRI parameters in the columns A-O of the subset data DB-1 or the columns A-O, R, and S of the subset data DB-2. Alternatively, the variables may be T1 mapping, T2 raw signal, T2 mapping, delta Ktrans, tau, Dt IVIM, fp IVIM, ADC (high b-values), R*, Ktrans from TM, Ktrans from ETM, Ktrans from SSM, Ve from TM, Ve from ETM, Ve from SSM, and standard PET.

The first group, for example, may be associated with a first data type or feature in a specific column of the subset data DB-1 or DB-2, and the second group may be associated with a second data type or feature in the specific column of the subset data DB-1 or DB-2, wherein the specific column of the subset data DB-1 or DB-2 may be one of the columns R-AR of the subset data DB-1 or one of the columns AA-AX of the subset data DB-2. In a first example, the first data type is associated with prostate cancer in the column R of the subset data DB-1, and the second data type is associated with non-prostate cancer (e.g., normal tissue and benign condition) in the column R of the subset data DB-1. In a second example, the first data type is associated with breast cancer in the column AA of the subset data DB-2, and the second data type is associated with non-breast cancer (e.g., normal tissue and benign condition) in the column AA of the subset data DB-2. In the case of the first group associated with a cancer type (e.g., prostate cancer or breast cancer) and the second group associated with a non-cancer type (e.g., non-prostate cancer or non-breast cancer), the cancer type may include data of interest for a single parameter, such as malignancy, mRNA expression, etc., and the non-cancer type may include normal tissue and benign conditions. The benign conditions may vary based on tissues. For example, the benign conditions for breast tissues may include fibroadenomas, cysts, etc.

In a third example, the first data type is associated with one of Gleason scores 0 through 10, such as Gleason score 5, in the column T of the subset data DB-1, and the second data type is associated with the others of Gleason scores 0 through 10, such as Gleason scores 0 through 4 and 6 through 10, in the column T of the subset data DB-1. In a fourth example, the first data type is associated with two or more of Gleason scores 0 through 10, such as Gleason scores greater than 7, in the column T of the subset data DB-1, and the second data type is associated with the others of Gleason scores 0 through 10, such as Gleason scores equal to and less than 7, in the column T of the subset data DB-1. In a fifth example, the first data type is associated with the percentage of cancer in a specific range from a first percent (e.g., 91 percent) to a second percent (e.g., 100 percent) in the column S of the subset data DB-1, and the second data type is associated with the percentage of cancer beyond the specific range in the column S of the subset data DB-1. In a sixth example, the first data type is associated with a small cell subtype in the column AE of the subset data DB-1, and the second data type is associated with a non-small cell subtype in the column AE of the subset data DB-1. Any event depicted in the invention may be the above-mentioned first data type or feature, occurrence of prostate cancer, occurrence of breast cancer, or a biopsy-diagnosed tissue or tumor characteristic for, e.g., specific cancerous cells.

After the step of constructing database is completed, the step of preprocessing parameters is performed to determine what the variables are conditionally independent. A technique for dimensionality reduction may allow reduction of some of the variables that are conditionally dependent to a single variable. Use of dimensionality reduction preprocessing of data may allow optimal use of all valuable information in datasets. The simplest method for dimensionality reduction may be simple aggregation and averaging of datasets. In one example, aggregation may be used for dynamic contrast-enhanced MRI (DCE-MRI) datasets. Ktrans and Ve measures from various different pharmacokinetic modeling techniques may be averaged to reduce errors and optimize sensitivity to tissue change.

For the variables, averaging and subtraction may be used to consolidate measures. Accordingly, five or more types of parameters may be selected or obtained from the variables. The five or more selected parameters are conditionally independent and may include T1 mapping, T2 mapping, delta Ktrans (obtained by subtracting "Ktrans from Tofts Model" from "Ktrans from Shutterspeed Model"), tau, Dt IVIM, fp IVIM, R*, average Ve, and average Ktrans in the respective columns A, C-G, J, P, and Q of the subset data DB-1 or DB-2. Alternatively, the five or more selected parameters may include T1 mapping, T2 mapping, delta Ktrans, tau, fp IVIM, R*, average Ve, average Ktrans, standard PET, and a parameter D obtained by averaging Dt IVIM and ADC (high b-values), wherein the parameter D is conditionally independent of every other selected parameter.

Figure 24:
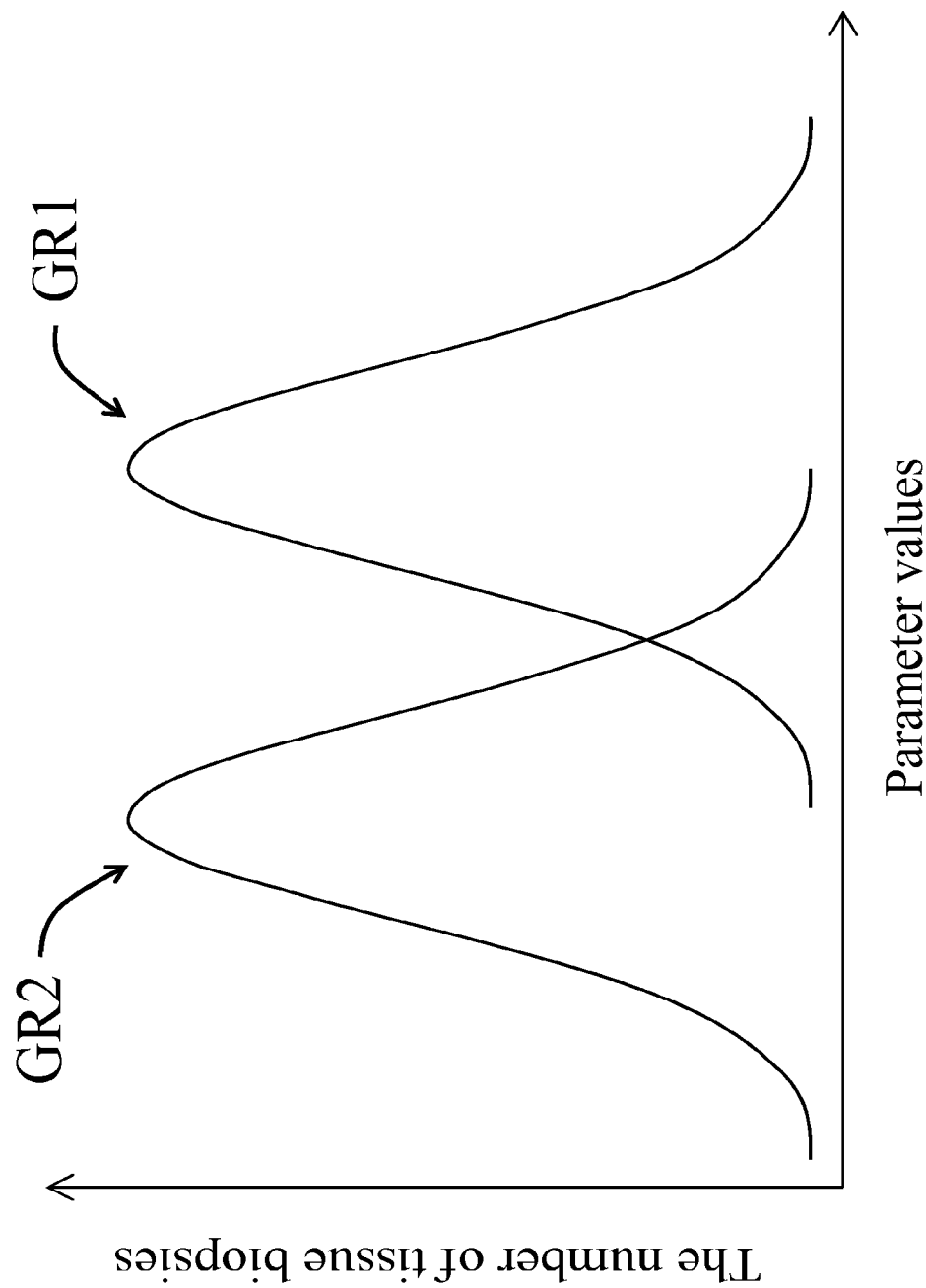
FIG. 24 is a diagram showing two Gaussian curves of two given different groups with respect to parameter measures.

After the step of preprocessing parameters is complete, the step of ranking parameters is performed to determine the optimal ones of the five or more selected parameters for use in classification, e.g., to find the optimal parameters that are most likely to give the highest posterior probabilities, so that a rank list of the five or more selected parameters is obtained. A filtering method, such as t-test, may be to look for an optimal distance between the first group (indicated by GR1) and the second group (indicated by GR2) for every one of the five or more selected parameters, as shown in FIG. 24. FIG. 24 shows two Gaussian curves of two given different groups (i.e., the first and second groups GR1 and GR2) with respect to parameter measures. In FIG. 24, X axis is values for a specific parameter, and Y axis is the number of tissue biopsies.

Four different criteria may be computed for ranking the five or more selected parameters. The first criterion is the p-value derived from a t-test of the hypothesis that the two features sets, corresponding to the first group and the second group, coming from distributions with equal means. The second criterion is the mutual information (MI) computed between the classes and each of the first and second groups. The last two criteria are derived from the minimum redundancymaximum relevance (mRMR) selection method.

In the step of identifying a training dataset, a training dataset of the first group and the second group is identified based on the rank list after the step of ranking parameters, and thereby the Bayesian classifier may be created based on the training dataset of the first group and the second group. In the step of determining posterior probabilities for test data, the posterior probabilities for the test data may be determined using the Bayesian classifier. Once the Bayesian classifier is created, the test data may be applied to predict posterior probabilities for high resolution probability maps.

In an alternative example, the classifier CF may be a neural network (e.g., probabilistic neural network, single-layer feed forward neural network, multi-layer perception neural network, or radial basis function neural network), a discriminant analysis, a decision tree (e.g., classification and regression tree, quick unbiased and efficient statistical tree, Chi-square automatic interaction detector, C5.0, or random forest decision tree), an adaptive boosting, a K-nearest neighbors algorithm, or a support vector machine. In this case, the classifier CF may be created based on information associated with the various MRI parameters for the ROIs 94 of the MRI slices $SI_1$-$SI_N$ registered to each of the biopsy tissues depicted in the subset data DB-1 or DB-2.

First Embodiment

After the big data database 70 and the classifier CF are created or constructed, a (voxelwise) probability map (i.e., a decision data map), composed of multiple computation voxels with the same size, for an event (i.e., a decision-making characteristic) may be generated or constructed for, e.g., evaluating or determining the health status of a subject such as healthy individual or patient, the physical condition of an organ or other structure inside the subject's body, or the subject's progress and therapeutic effectiveness by sequentially performing six steps S1 through S6 illustrated in FIG. 4. The steps S1-S6 may be performed based on the moving window MW with a suitable shape such as a circular shape, a square shape, a rectangular shape, a hexagonal shape, or an octagonal shape. The moving window MW is selected for a circular shape, i.e., the circular moving window 2, to perform the steps S1-S6 as mentioned in the following paragraphs. Referring to FIG. 4, in the step S1, a MRI image 10 (single slice) shown in FIG. 5 is obtained from the subject by a MRI device or system. The MRI image 10 (i.e., a molecular image) is composed of multiple voxels in its field of view (FOV) to show an anatomical region of the subject, such as prostate. In an alternative embodiment, the MRI image 10 may show another anatomical region of the subject, such as breast, brain, liver, lung, cervix, bone, sarcomas, metastatic lesion or site, capsule around the prostate, pelvic lymph nodes around the prostate, or lymph node.

In the step S2, a desired or anticipated region 11 is determined on the MRI image 10, and a computation region 12 for the probability map is set in the desired or anticipated region 11 of the MRI image 10 and defined with the computation voxels based on the size (e.g., the radius Rm) of the moving window 2 and the size and shape of the smallgrids 6 in the moving window 2 such as the width Wsq of the small squares 6 or the width Wrec and the length Lrec of the small rectangles 6. A side length of the computation region 12 in the x direction, for example, may be calculated by obtaining a first maximum positive integer of a side length of the desired or anticipated region 11 in the x direction divided by the width Wsq of the small squares 6 in the moving window 2, and multiplying the width Wsq by the first maximum positive integer; a side length of the computation region 12 in the y direction may be calculated by obtaining a second maximum positive integer of a side length of the desired or anticipated region 11 in the y direction divided by the width Wsq of the small squares 6 in the moving window 2, and multiplying the width Wsq by the second maximum positive integer. Alternatively, a side length of the computation region 12 in the x direction may be calculated by obtaining a first maximum positive integer of a side length of the desired or anticipated region 11 in the x direction divided by the width Wrec of the small rectangles 6 in the moving window 2, and multiplying the width Wrec by the first maximum positive integer; a side length of the computation region 12 in the y direction may be calculated by obtaining a second maximum positive integer of a side length of the desired or anticipated region 11 in the y direction divided by the length Lrec of the small rectangles 6 in the moving window 2, and multiplying the length Lrec by the second maximum positive integer. The computation region 12 may cover at least 10, 25, 50, 80, 90 or 95 percent of the FOV of the MRI image 10, which may include the anatomical region of the subject. The computation region 12, for example, may be shaped like a parallelogram such as square or rectangle.

The size and shape of the computation voxels used to compose the probability map, for example, may be defined based on the radius Rm of the moving window 2, wherein the radius Rm is calculated based on, e.g., the statistical distribution or average of the radii Rw of the planar cylinders 98 transformed from the volumes of the prostate biopsy tissues provided for the pathologist diagnoses depicted in the subset data DB-1, as illustrated in the section of "description of moving window and probability map". Each of the computation voxels, for example, may be defined as a square with the width Wsq in the case of the moving window 2 defined to include the small squares 6 each having the width Wsq. Alternatively, each of the computation voxels may be defined as a rectangle with the width Wrec and the length Lrec in the case of the moving window 2 defined to include the small rectangles 6 each having the width Wrec and the length Lrec.

Figure 6A:
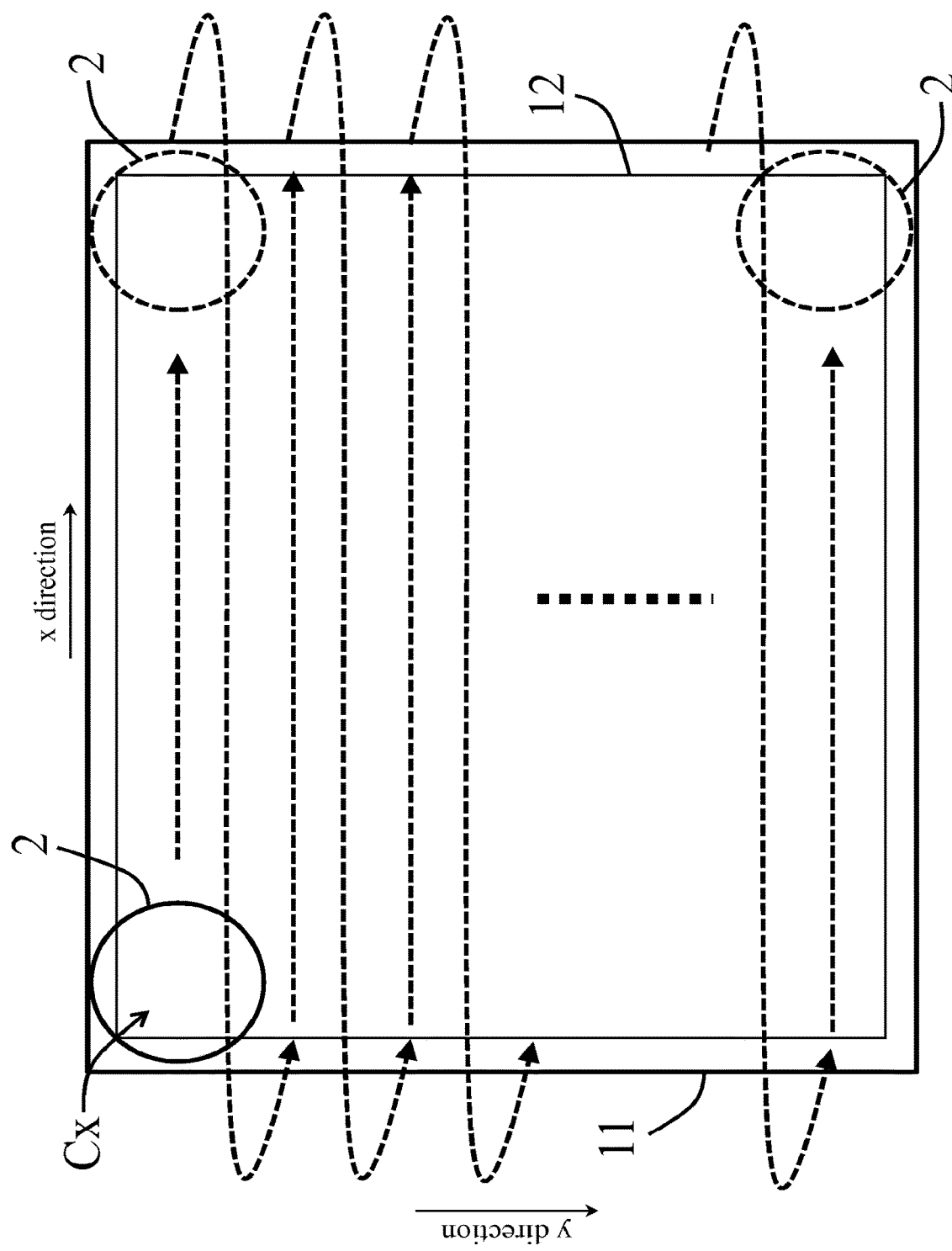
FIG. 6A is a schematic drawing showing a circular window moving across a computation region of a MRI slice in accordance with an embodiment of the present invention.
Figure 6B:
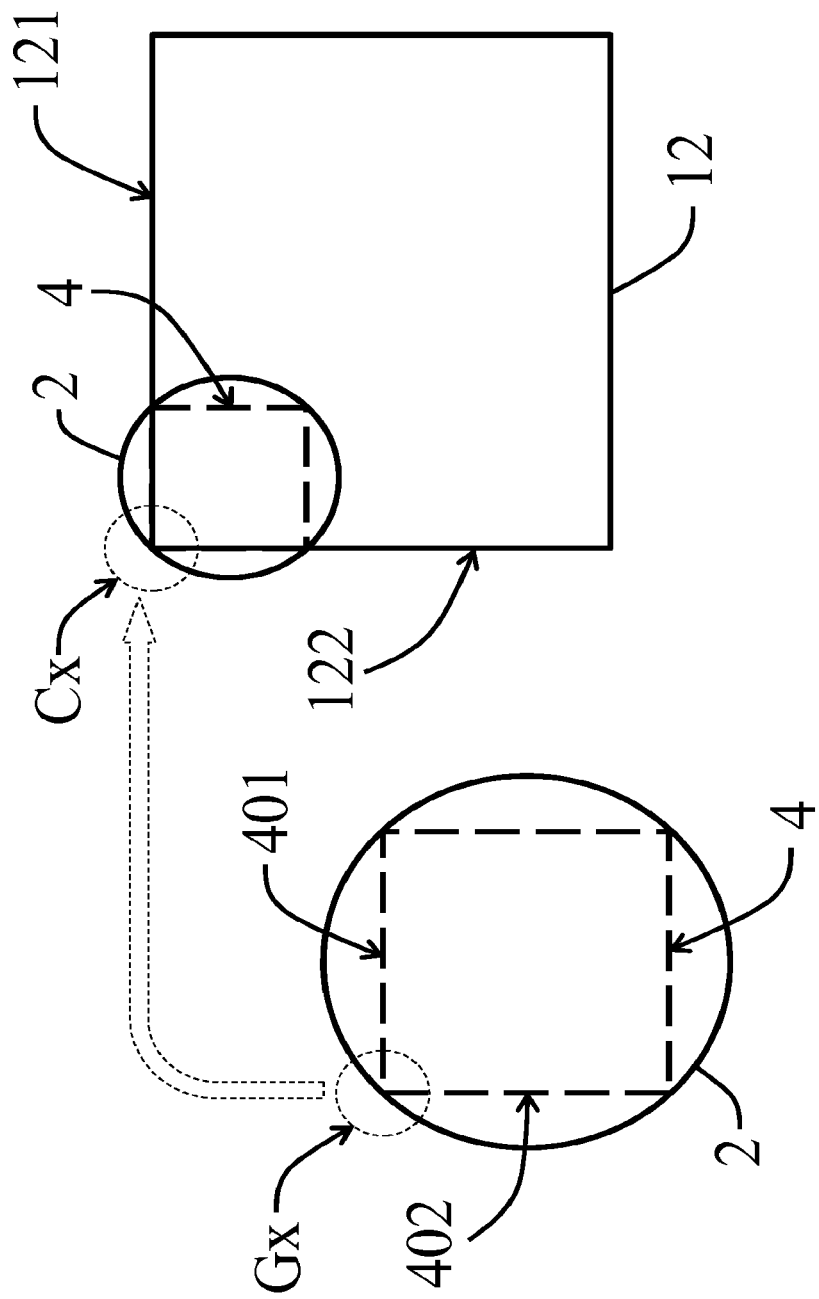
FIG. 6B shows a square inscribed in a circular window having a corner aligned with a corner of a computation region of a MRI slice in accordance with an embodiment of the present invention.

A step for abbreviated search functions (such as looking for one or more specific areas of the MRI image 10 where diffusion signals are above a certain signal value) may be performed between the steps S1 and S2, and the computation region 12 may cover the one or more specific areas of the MRI image 10. For clear illustration of the following steps, FIGS. 6A and 6B show the computation region 12 without the MRI image 10. Referring to FIG. 6A, in the step S3 of FIG. 4, after the computation region 12 and the size and shape of the computation voxels of the probability map are defined or determined, the stepping of the moving window 2 and the overlapping between two neighboring stops of the moving window 2 are determined. In the step S3, the moving window 2, illustrated in FIG. 3A, 3B or 3C for example, moves across the computation region 12 at a regular step or interval of a fixed distance in the x and y directions, and measures of specific MRI parameters (each, for example, may be the mean or a weighted mean) for each stop of the moving window 2 for the computation region 12 may be derived or obtained from the MRI image 10 or a registered imaging dataset including, e.g., the MRI image 10 and different MRI parameter maps registered to the MRI image 10. In an alternative example, the measures for some of the specific MRI parameters for each stop of the moving window 2 may be derived from different MRI parameter maps registered to the MRI image 10, and the measures for the others may be derived from the same parameter map registered to the MRI image 10. The fixed distance in the x direction may be substantially equal to the width Wsq in the case of the computation voxels defined as the squares with the width Wsq or may be substantially equal to the width Wrec in the case of the computation voxels defined as the rectangles with the width Wrec and the length Lrec. The fixed distance in the y direction may be substantially equal to the width Wsq in the case of the computation voxels defined as the squares with the width Wsq or may be substantially equal to the length Lrec in the case of the computation voxels defined as the rectangles with the width Wrec and the length Lrec.

For more elaboration, referring to FIGS. 6A and 6B, the moving window 2 may start at a corner Cx of the computation region 12. In the beginning of moving the moving window 2 across the computation region 12, the square 4 inscribed in the moving window 2 may have a corner Gx aligned with the corner Cx of the computation region 12. In other words, the square 4 inscribed in the moving window 2 has an upper side 401 aligned with an upper side 121 of the computation region 12 and a left side 402 aligned with a left side 122 of the computation region 12. Two neighboring stops of the moving window 2 that are shifted from each other by the fixed distance in the x or y direction partially overlap each other, and the ratio of the overlap of the two neighboring stops of the moving window 2 to the area of any one of the two neighboring stops of the moving window 2 may range from, equal to or greater than 50 percent up to, equal to or less than 99 percent.

The specific MRI parameters for each stop of the moving window 2 may include T1 mapping, T2 raw signal, T2 mapping, delta Ktrans, tau, Dt IVIM, fp IVIM, ADC (high b-values), nADC (high b-values), R*, Ktrans from TM, ETM and SSM, and Ve from TM and SSM, which may be referred to the types of the MRI parameters in the columns A-O of the subset data DB-1, respectively. Alternatively, the specific MRI parameters for each stop of the moving window 2 may include four or more of the following: T1 mapping, T2 raw signal, T2 mapping, Ktrans from TM, ETM, and SSM, Ve from TM and SSM, delta Ktrans, tau, ADC (high b-values), nADC (high b-values), Dt IVIM, fp IVIM, and R*. The specific MRI parameters of different modalities may be obtained from registered (multi-parametric) image sets (or the MRI parameter maps in the registered (multi-parametric) image dataset), and rigid and nonrigid standard registration techniques may be used to get each section of anatomy into the same exact coordinate location on each of the registered (multi-parametric) image sets (or on each of the MRI parameter maps).

Figure 7A:
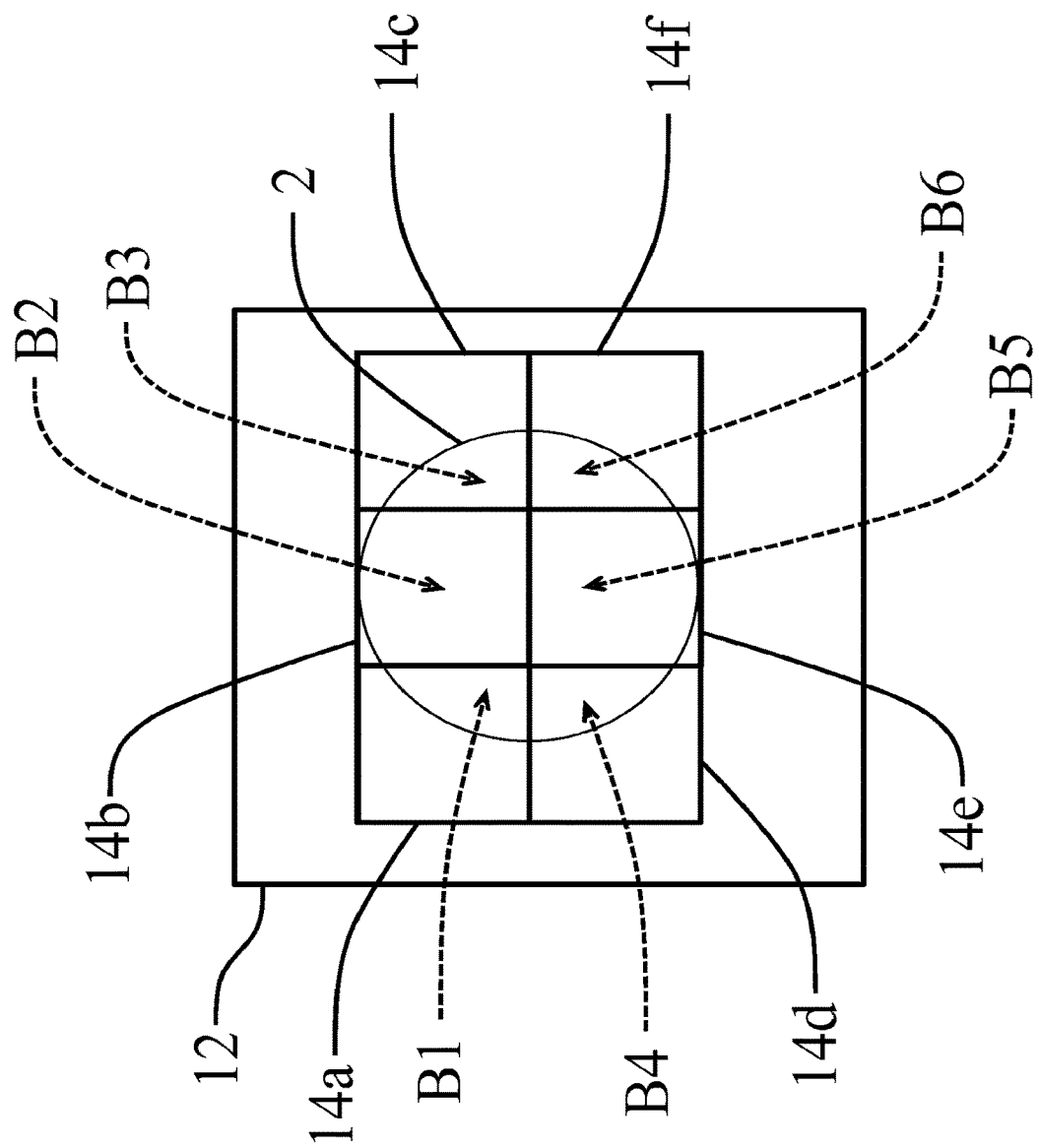
FIG. 7A is a schematic drawing showing multiple voxels of a MRI slice covered by a circular window in accordance with an embodiment of the present invention.

Referring to FIG. 7A, the moving window 2 at each stop may cover or overlap multiple voxels, e.g., 14a through 14f, in the computation region 12, of the MRI image 10. A MRI parameter such as T1 mapping for each stop of the moving window 2 may be calculated or measured by summing values of the MRI parameter for the voxels 14a-14f weighed or multiplied by the respective percentages of areas B1, B2, B3, B4, B5 and B6, overlapping with the respective voxels 14a-14f in the moving window 2, occupying the moving window 2. By this way, other MRI parameters (e.g., those in the columns B-O of the subset data DB-1) for each stop of the moving window 2 are measured. Taking an example of T1 mapping, in the case of the moving window 2 at a certain stop, values of T1 mapping for the voxels 14a-14f and the percentages of the areas B1-B6 occupying the moving window 2 are assumed as shown in FIG. 7B. A measure, i.e., 1010.64, of T1 mapping for the stop of the moving window 2 may be obtained or calculated by summing (1) the value, i.e., 1010, of T1 mapping for the voxel 14a multiplied by the percentage, i.e., 6%, of the area B1, overlapping with the voxel 14a in the moving window 2, occupying the moving window 2, (2) the value, i.e., 1000, of T1 mapping for the voxel 14b multiplied by the percentage, i.e., 38%, of the area B2, overlapping with the voxel 14b in the moving window 2, occupying the moving window 2, (3) the value, i.e., 1005, of T1 mapping for the voxel 14c multiplied by the percentage, i.e., 6%, of the area B3, overlapping with the voxel 14c in the moving window 2, occupying the moving window 2, (4) the value, i.e., 1020, of T1 mapping for the voxel 14d multiplied by the percentage, i.e., 6%, of the area B4, overlapping with the voxel 14d in the moving window 2, occupying the moving window 2, (5) the value, i.e., 1019, of T1 mapping for the voxel 14e multiplied by the percentage, i.e., 38%, of the area B5, overlapping with the voxel 14e in the moving window 2, occupying the moving window 2, and (6) the value, i.e., 1022, of T1 mapping for the voxel 14f multiplied by the percentage, i.e., 6%, of the area B6, overlapping with the voxel 14f in the moving window 2, occupying the moving window 2. Alternatively, the measure of each of the specific MRI parameters for each stop of the moving window 2 may be the Gaussian weighted average of measures, for said each of the specific MRI parameters, for the voxels, e.g., 14a-14f of the MRI image 10 overlapping with said each stop of the moving window 2.

The registered imaging dataset may be created for the subject to include, e.g., multiple registered MRI slice images (including, e.g., MRI image 10) and/or corresponding MRI parameters obtained from various equipment, machines, or devices or from a defined time-point (e.g., specific date) or time range (e.g., within five days after treatment). Each of the MRI parameters in the subject's registered imaging dataset requires alignment or registration. The registration can be done by, for examples, using unique anatomical marks, structures, tissues, geometry, and/or shapes or using mathematical algorithms and computer pattern recognition. The measures of the specific imaging parameters for each stop of the moving window 2, for example, may be obtained from the registered imaging dataset for the subject.

Referring to FIG. 4, in the step S4 (optional), the reduction of the MRI parameters may be performed using, e.g., subset selection, aggregation, and dimensionality reduction so that a parameter set for each stop of the moving window 2 is obtained. The parameter set for each stop of the moving window 2 may include the measures for some of the specific MRI parameters from the step S3 (e.g., T1 mapping, T2 mapping, delta Ktrans, tau, Dt IVIM, fp IVIM, and R*) and values of average Ktrans (obtained by averaging Ktrans from TM, Ktrans from ETM, and Ktrans from SSM) and average Ve (obtained by averaging Ve from TM and Ve from SSM). T2 raw signal, ADC (high b-values), and nADC (high b-values) are not selected into the parameter set because the three MRI parameters are not determined to be conditionally independent. T1 mapping, T2 mapping, delta Ktrans, tau, Dt IVIM, fp IVIM, and R* are selected into the parameter set because the seven MRI parameters are determined to be conditionally independent. Performing the step S4 may reduce parameter noise, create new parameters, and assure conditional independence needed for (Bayesian) classification described in the step S5.

In the step S5, the parameter set for each stop of the moving window 2 from the step S4 (or the measures of some or all of the specific MRI parameters for each stop of the moving window 2 from the step S3) may be matched to a biomarker library or the classifier CF for an event (e.g., the first data type or feature depicted in the section of "description of classifier CF", or biopsy-diagnosed tissue characteristic for, e.g., specific cancerous cells or occurrence of prostate or breast cancer) created based on data associated with the event from the subset data DB-1. Accordingly, a probability PW of the event for each stop of the moving window 2 is obtained. In other words, the probability PW of the event for each stop of the moving window 2 may be obtained based on the parameter set (from the step S4) or the measures of some or all of the specific MRI parameters (from the step S3) for said each stop of the moving window 2 to match a matching dataset from the established or constructed biomarker library or classifier CF. The biomarker library or classifier CF, for example, may contain population-based information of MRI imaging data and other information such as clinical and demographic data for the event. In the invention, the probability PW of the event for each stop of the moving window 2 is assumed to be that for the square 4 inscribed in said each stop of the moving window 2.

Figure 8:
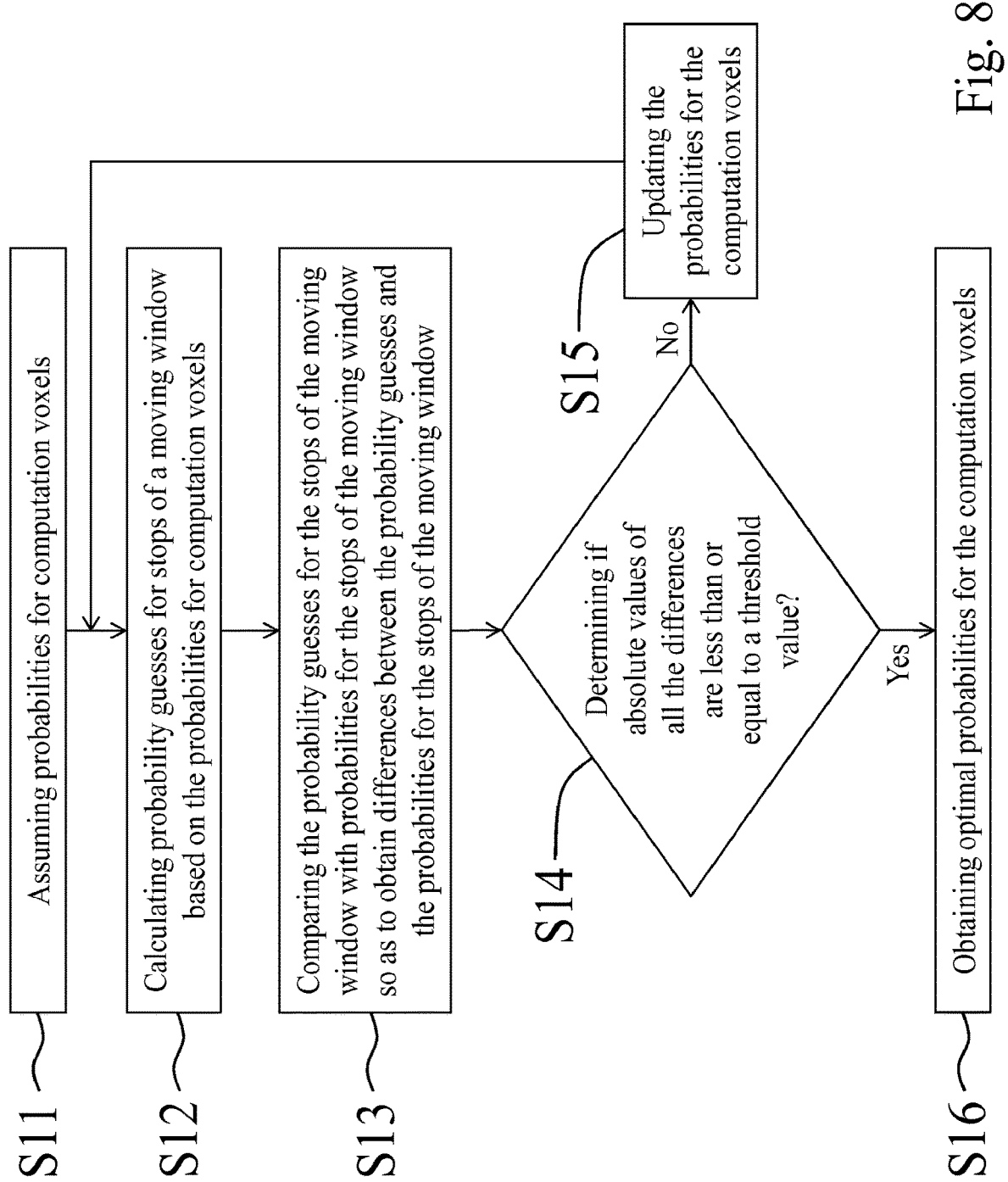
FIG. 8 is a flow chart depicting an algorithm for generating a probability map in accordance with an embodiment of the present invention.

In the step S6, an algorithm including steps S11 through S16 depicted in FIG. 8 is performed based on the probabilities PWs of the event for the stops of the moving window 2 to compute probabilities PVs of the event for the respective computation voxels, and the probabilities PVs of the event for the respective computation voxels form the probability map. The probability map may be obtained in a short time (such as 10 minutes or 1 hour) after the MRI slice 10 obtained. To illustrate the algorithm, the moving window 2 may be defined to include at least four squares 6, as shown in FIG. 3A, 3B or 3C. Each of the squares 6 within the moving window 2, for example, may have an area less than 25% of that of the moving window 2. Two neighboring stops of the moving window 2, for example, may have an overlapped region with an area ranging from 20% to 99% of that of any one of the two neighboring stops of the moving window 2, and some of the squares 6 inside each of the two neighboring stops of the moving window 2 may be within the overlapped region of the two neighboring stops of the moving window 2. Alternatively, two neighboring stops of the moving window 2 may have an overlapped region with an area ranging from 1% to 20% of that of any one of the two neighboring stops of the moving window 2. Referring to FIG. 8, in the step S11, the probability PV of the event for each of the computation voxels is assumed by, e.g., averaging the probabilities PWs of the event for some of the stops of the moving window 2, each having one of the squares 6 overlapping or covering said each of the computation voxels.

In the step S12, a probability guess PG for each stop of the moving window 2 is calculated by, e.g., averaging the probabilities PVs of the event for all the computation voxels inside said each stop of the moving widow 2. In the step S13, a difference DW between the probability guess PG and the probability PW of the event for each stop of the moving window 2 is calculated by, e.g., subtracting the probability PW of the event for said each stop of the moving window 2 from the probability guess PG for said each stop of the moving window 2.

In the step S14, an absolute value of the difference DW between the probability guess PG and the probability PW of the event for each stop of the moving window 2 is compared with a preset threshold error or value (e.g., 0.001 or 0.0001) to determine whether an error, i.e., the absolute value of the difference DW, between the probability guess PG and the probability PW of the event for each stop of the moving window 2 is less than or equal to the preset threshold error or value. If the absolute value of the difference DW for each stop of the moving window 2 is determined in the step S14 to be less than or equal to the preset threshold error or value, the step S16 continues. In the step S16, the probabilities PVs of the event for the computation voxels are determined to be optimal, which are called optimal probabilities hereinafter, and the optimal probabilities of the respective computation voxels form the probability map of the event for the MRI image 10 for the subject having imaging information (e.g., MRI imaging information). After the optimal probabilities for the respective computation voxels are obtained in the step S16, the algorithm is completed.

If any one of the absolute values of the differences DWs for all the stops of the moving window 2 is determined in the step S14 to be greater than the preset threshold error or value, the step S15 continues. In the step S15, the probability PV of the event for each of the computation voxels is updated or adjusted by, e.g., subtracting an error correction factor ECF for said each of the computation voxels from the probability PV of the event for said each of the computation voxels. The error correction factor ECF for each of the computation voxels is calculated by, e.g., summing error correction contributions from the stops of the moving window 2 each having one of its squares 6 covering or overlapping said each of the computation voxels; each of the error correction contributions to said each of the computation voxels, for example, may be calculated by multiplying the difference DW for a corresponding one of the stops of the moving window 2 by an area ratio of an overlapped area between said each of the computation voxels and the corresponding one of the stops of the moving window 2 to an area of the square 4 inscribed in the corresponding one of the stops of the moving window 2. Alternatively, the error correction factor ECF for each of the computation voxels is calculated by, e.g., dividing the sum of the differences DWs for overlapping ones of the stops of the moving window 2, each having one of its squares 6 covering or overlapping said each of the computation voxels, by the number of all the squares 6 within the moving window 2. After the probabilities PVs of the event for the computation voxels are updated, the steps S12-S15 are performed repeatedly based on the updated probabilities PVs of the event for the computation voxels in the step S15, until the absolute value of the difference DW between the probability guess PG and the probability PW of the event for each stop of the moving window 2 is determined in the step S14 to be less than or equal to the preset threshold error or value.

The steps S12-S14 depicted in FIG. 8 may be performed N times, where N is a positive integer, e.g., greater than 2, 5 or 10. In the first time, the steps S12-S14 are considered to perform the aforementioned steps ST2-ST4, respectively; in this case, the step S11 is considered to perform the aforementioned step ST1. In the second time, the steps S12-S14 are considered to perform the aforementioned steps ST7-ST9, respectively; in this case, the step S15 is considered to perform the aforementioned steps ST5 and ST6. In the third through N times, the steps S12-S14, as well as the step S15, are considered to perform the aforementioned step ST10. In addition, the step S16 is considered to perform the aforementioned step ST11.

Figure 9:
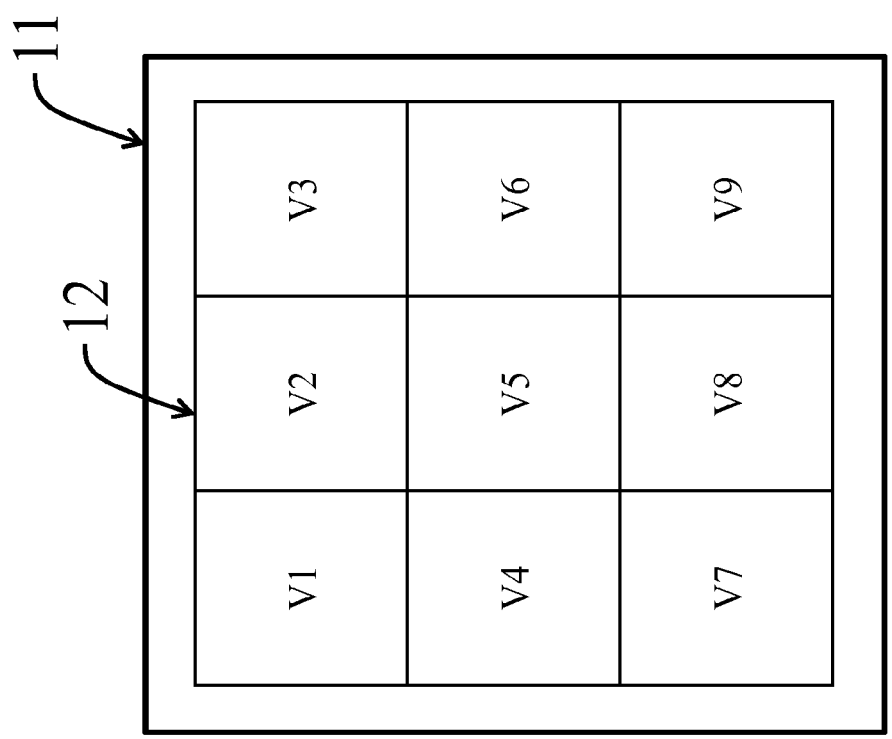
FIG. 9 shows a computation region defined with nine computation voxels for a probability map in accordance with an embodiment of the present invention.
Figure 10B:
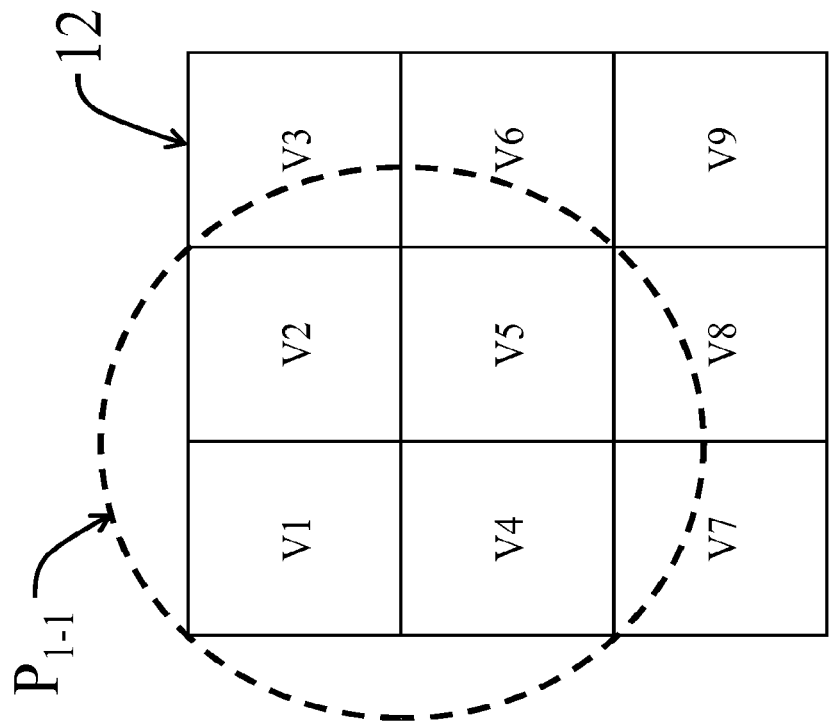
FIGS. 10B, 10D, 10F, and 10H show a circular window moving across a computation region defined with nine computation voxels in accordance with an embodiment of the present invention.
Figure 10A:
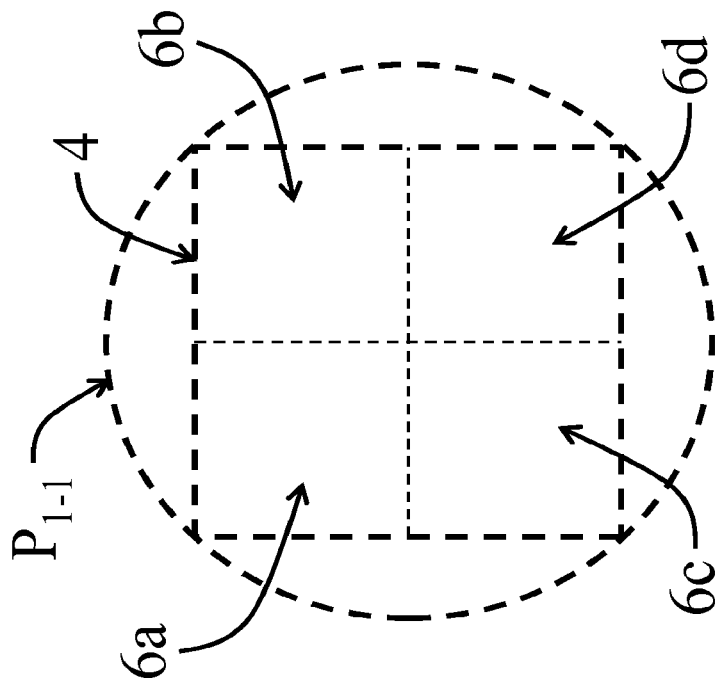
FIGS. 10A, 10C, 10E, and 10G show four stops of a circular moving window, each of which includes four non-overlapped small squares, in accordance with an embodiment of the present invention.
Figure 10D:
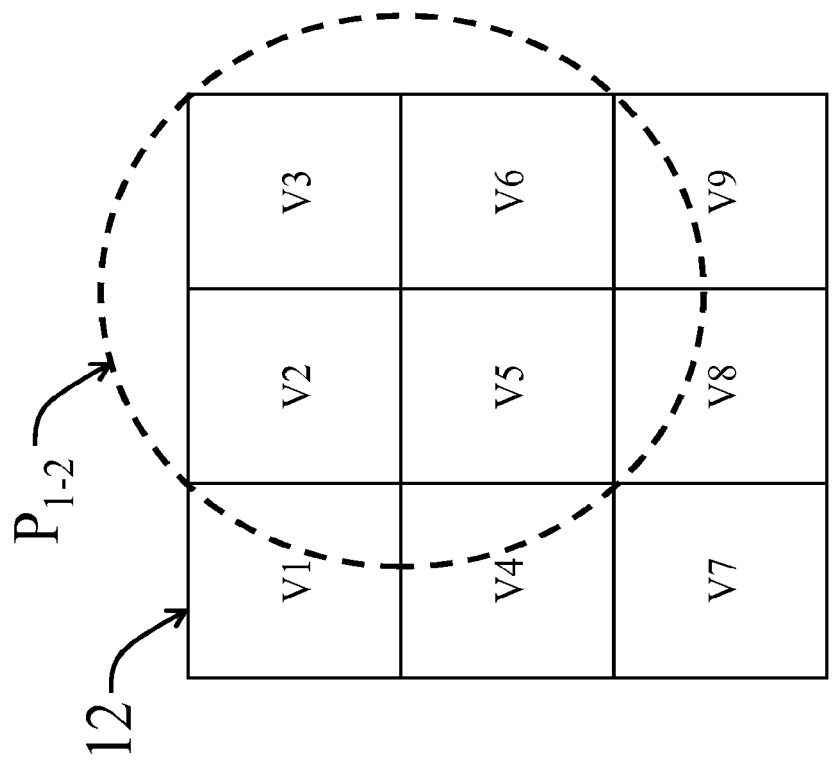
Figure 10C:
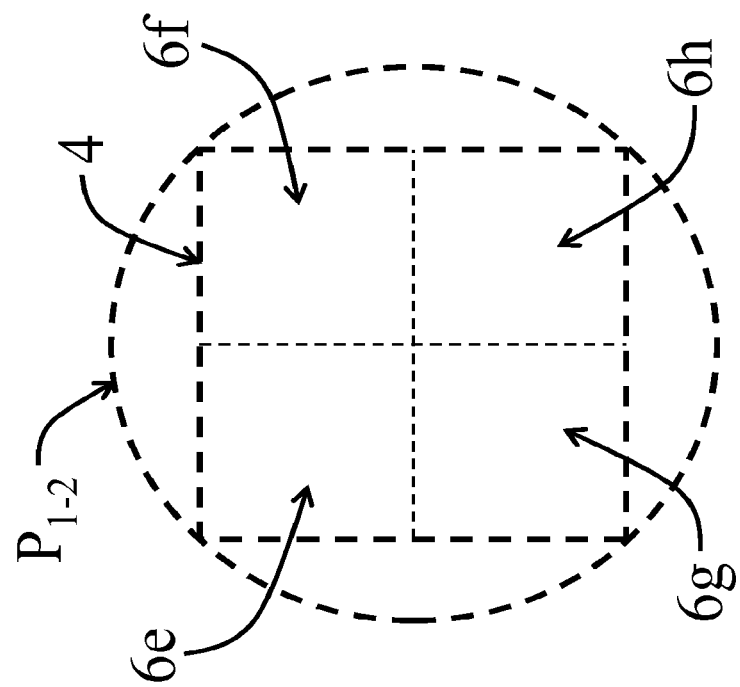
Figure 10F:
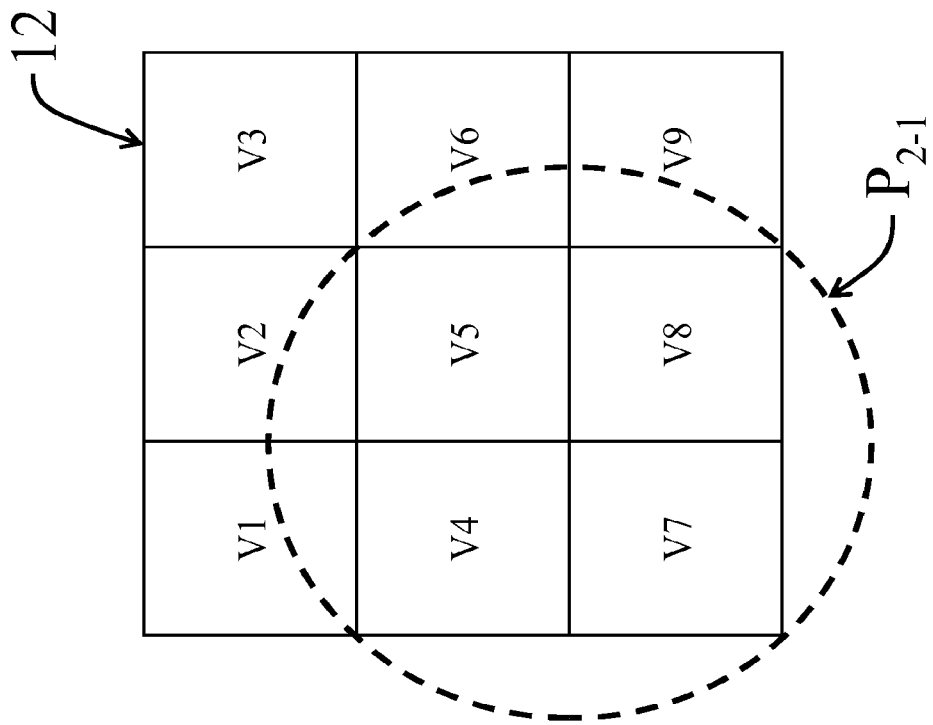
Figure 10E:
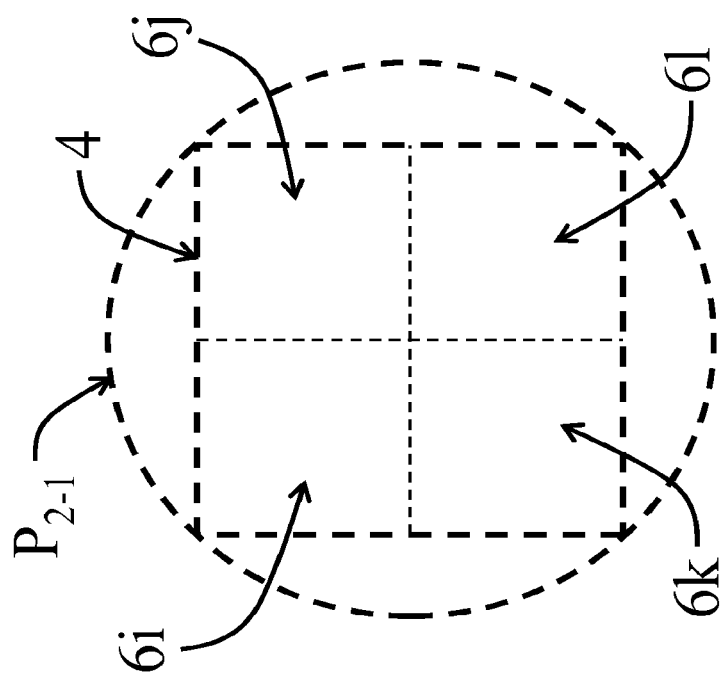
Figure 10H:
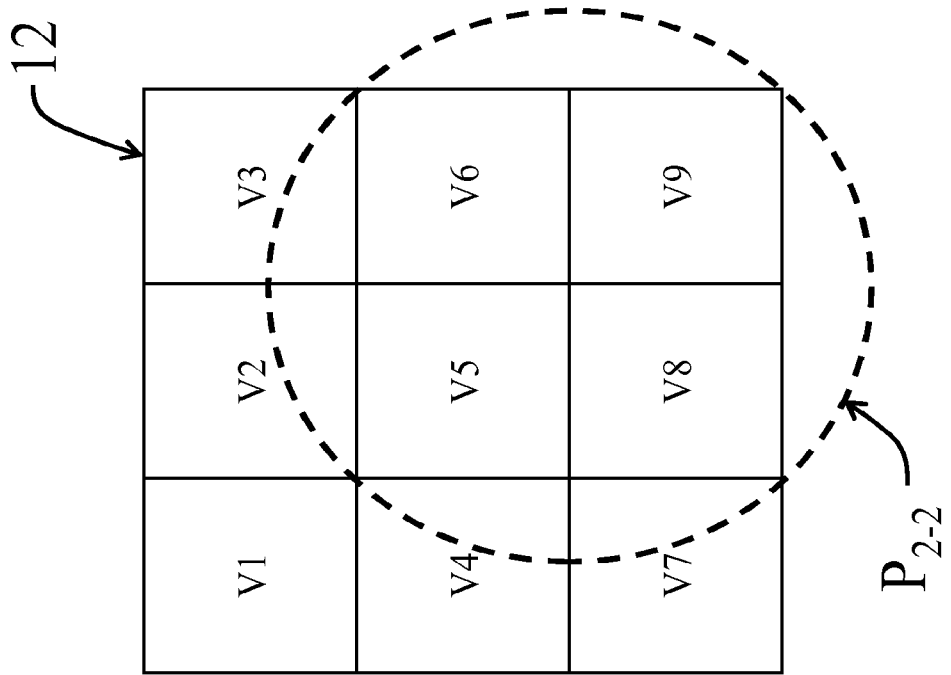
Figure 10G:
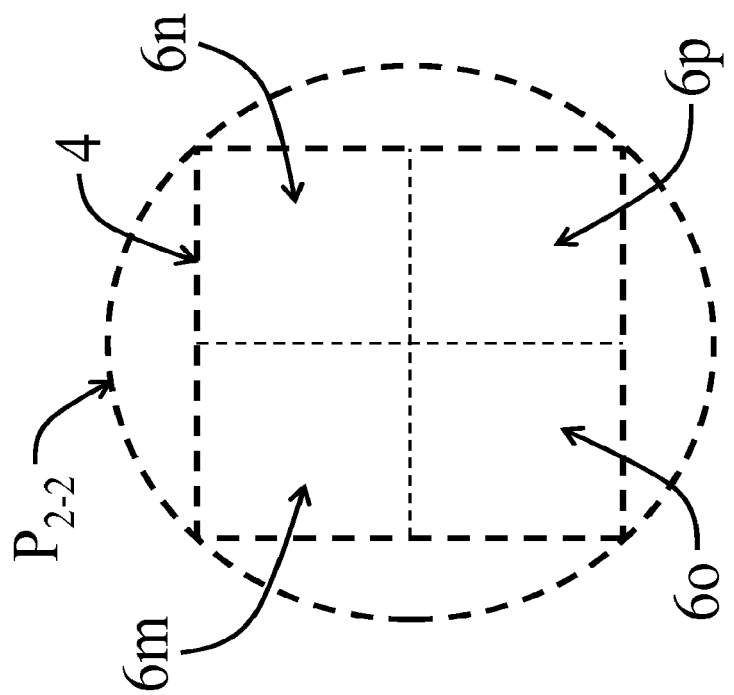

For detailed description of the steps S11-S16, the square 4 inscribed in the moving window 2 with the radius Rm is divided into, e.g., four small squares 6 each having width Wsq as shown in FIG. 3A, and in the step S2, the computation region 12 for the probability map is defined with, e.g., nine computation voxels V1 through V9 shown in FIG. 9 based on the width Wsq of the four small squares 6 in the moving window 2. Each of the nine computation voxels V1-V9 used to compose the probability map is defined as a square with the width Wsq. Next, referring to FIGS. 10B, 10D, 10F and 10H, the moving window 2 moves across the computation region 12 at a regular step or interval of a fixed distance in the x and y directions, and measures of the specific MRI parameters for four stops $P_{1\text{-}1}$, $P_{1\text{-}2}$, $P_{2\text{-}1}$ and $P_{2\text{-}2}$ of the moving window 2 are obtained from the MRI image 10 or the registered imaging dataset. In the example, the fixed distance is substantially equal to the width Wsq. Referring to FIGS. 10A and 10B, four small squares 6a, 6b, 6c and 6d, i.e., the four squares 6, within the square 4 inscribed in the stop $P_{1\text{-}1}$ of the moving window 2 overlap or cover the four computation voxels V1, V2, V4 and V5, respectively, and each of the squares 6a, 6b, 6c and 6d has an area less than 25% of that of the stop $P_{1\text{-}1}$ of the moving window 2. Referring to FIGS. 10C and 10D, four small squares 6e, 6f, 6g and 6h, i.e., the four squares 6, within the square 4 inscribed in the stop $P_{1\text{-}2}$ of the moving window 2 overlap or cover the four computation voxels V2, V3, V5 and V6, respectively, and each of the squares 6e, 6f, 6g and 6h has an area less than 25% of that of the stop $P_{1\text{-}2}$ of the moving window 2. Referring to FIGS. 10E and 10F, four small squares 6i, 6j, 6k and 6l, i.e., the four squares 6, within the square 4 inscribed in the stop $P_{2\text{-}1}$ of the moving window 2 overlap or cover the four computation voxels V4, V5, V7 and V8, respectively, and each of the squares 6i, 6j, 6k and 6l has an area less than 25% of that of the stop $P_{2\text{-}1}$ of the moving window 2. Referring to FIGS. 10G and 10H, four small squares 6m, 6n, 6o and 6p, i.e., the four squares 6, within the square 4 inscribed in the stop $P_{2\text{-}2}$ of the moving window 2 overlap or cover the four computation voxels V5, V6, V8 and V9, respectively, and each of the squares 6m, 6n, 6o and 6p has an area less than 25% of that of the stop $P_{2\text{-}2}$ of the moving window 2. For details about the squares 6a-6p, please refer to the squares 6 illustrated in FIG. 3A.

After the measures of the specific MRI parameters for the stops $P_{1\text{-}1}$, $P_{1\text{-}2}$, $P_{2\text{-}1}$ and $P_{2\text{-}2}$ of the moving window 2 are obtained, the step S5 is performed to obtain the probabilities PWs of the event for the respective stops $P_{1\text{-}1}$, $P_{1\text{-}2}$, $P_{2\text{-}1}$ and $P_{2\text{-}2}$ of the moving window 2. The probabilities PWs of the event for the four stops $P_{1\text{-}1}$, $P_{1\text{-}2}$, $P_{2\text{-}1}$ and $P_{2\text{-}2}$ of the moving window 2, for example, are 0.8166, 0.5928, 0.4407 and 0.5586, respectively. In the example, the four probabilities PWs of the event for the four stops $P_{1\text{-}1}$, $P_{1\text{-}2}$, $P_{2\text{-}1}$ and $P_{2\text{-}2}$ of the moving window 2 are assumed to be those for the four squares 4 inscribed in the respective stops $P_{1\text{-}1}$, $P_{1\text{-}2}$, $P_{2\text{-}1}$ and $P_{2\text{-}2}$ of the moving window 2, respectively. In other words, the four probabilities of the event for the four squares 4 inscribed in the four stops $P_{1\text{-}1}$, $P_{1\text{-}2}$, $P_{2\text{-}1}$ and $P_{2\text{-}2}$ of the moving window 2 are 0.8166, 0.5928, 0.4407 and 0.5586, respectively.

Next, the algorithm depicted in FIG. 8 is performed based on the probabilities PWs of the event for the respective stops $P_{1\text{-}1}$, $P_{1\text{-}2}$, $P_{2\text{-}1}$ and $P_{2\text{-}2}$ of the moving window 2 to obtain or calculate optimal probabilities of the event for the computation voxels V1-V9, as described in the following specification. First of all, the probabilities PVs of the event for the computation voxels V1-V9 as shown in FIG. 11A are assumed by the step S11. In the step S11, referring to FIGS. 10A-10H and 11A, because the only stop $P_{1\text{-}1}$ of the moving window 2 has the square 6a overlapping the computation voxel V1, the probability PV of the event for the computation voxel V1 is assumed to be the probability PW, i.e., 0.8166, of the event for the stop $P_1$ of the moving window 2. Similarly, the probabilities PVs of the event for the computation voxels V3, V7 and V9 are assumed to be the probabilities PWs, i.e., 0.5928, 0.4407 and 0.5586, of the event for the stops $P_{1\text{-}2}$, $P_{2\text{-}1}$, and $P_{2\text{-}2}$ of the moving window 2, respectively. Because the only two stops $P_{1\text{-}1}$ and $P_{1\text{-}2}$ of the moving window 2 have the squares 6b and 6e overlapping the computation voxel V2, the probability PV of the event for the computation voxel V2 is assumed to be the average, i.e., 0.7047, of the two probabilities PWs, i.e., 0.8166 and 0.5928, of the event for the stops $P_{1-1}$ and $P_{1-2}$ of the moving window 2. Similarly, the probability PV of the event for the computation voxel V4 is assumed to be the average, i.e., 0.6286, of the probabilities PWs, i.e., 0.8166 and 0.4407, of the event for the stops $P_{1-1}$ and $P_{2-1}$ of the moving window 2. The probability PV of the event for the computation voxel V6 is assumed to be the average, i.e., 0.5757, of the probabilities PWs, i.e., 0.5928 and 0.5586, of the event for the stops $P_{1-2}$ and $P_{2-2}$ of the moving window 2. The probability PV of the event for the computation voxel V8 is assumed to be the average, i.e., 0.4996, of the probabilities PWs, i.e., 0.4407 and 0.5586, of the event for the stops $P_{2-1}$ and $P_{2-2}$ of the moving window 2. Because the only four stops $P_{1-1}$, $P_{1-2}$, $P_{2-1}$ and $P_{2-2}$ of the moving window 2 have four squares 6d, 6g, 6j and 6m overlapping the computation voxel V5, the probability PV of the event for the computation voxel V5 is assumed to be the average, i.e., 0.6022, of the four probabilities PWs, i.e., 0.8166, 0.5928, 0.4407 and 0.5586, of the event for the stops $P_{1-1}$, $P_{1-2}$, $P_{2-1}$ and $P_{2-2}$ of the moving window 2.

After the probabilities PVs of the event for the computation voxels V1-V9 are assumed, the step S12 is performed to obtain a first probability guess PG, i.e., 0.6880, for the stop $P_{1-1}$ of the moving window 2, a second probability guess PG, i.e., 0.6188, for the stop $P_{1-2}$ of the moving window 2, a third probability guess PG, i.e., 0.5428, for the stop $P_{2-1}$ of the moving window 2, and a fourth probability guess PG, i.e., 0.5590, for the stop $P_{2-2}$ of the moving window 2. The first probability guess PG for the stop $P_{1-1}$ of the moving window 2 is calculated by averaging the probabilities PVs, i.e., 0.8166, 0.7047, 0.6286 and 0.6022, of the event for the computation voxels V1, V2, V4 and V5 inside the stop $P_{1-1}$ of the moving window 2. The second probability guess PG for the stop $P_{1-2}$ of the moving window 2 is calculated by averaging the probabilities PVs, i.e., 0.7047, 0.5928, 0.6022 and 0.5757, of the event for the computation voxels V2, V3, V5 and V6 inside the stop $P_{1-2}$ of the moving window 2. The third probability guess PG for the stop $P_{2-1}$ of the moving window 2 is calculated by averaging the probabilities PVs, i.e., 0.6286, 0.6022, 0.4407 and 0.4996, of the event for the computation voxels V4, V5, V7 and V8 inside the stop $P_{2-1}$ of the moving window 2. The fourth probability guess PG for the stop $P_{2-2}$ of the moving window 2 is calculated by averaging the probabilities PVs, i.e., 0.6022, 0.5757, 0.4996 and 0.5586, of the event for the computation voxels V5, V6, V8 and V9 inside the stop $P_{2-2}$ of the moving window 2.

After the first through fourth probability guesses PGs are obtained or calculated, the step S13 is performed to obtain a first difference DW between the first probability guess PG and the probability PW of the event for the stop $P_{1-1}$ of the moving window 2, a second difference DW between the second probability guess PG and the probability PW of the event for the stop $P_{1-2}$ of the moving window 2, a third difference DW between the third probability guess PG and the probability PW of the event for the stop $P_{2-1}$ of the moving window 2, and a fourth difference DW between the fourth probability guess PG and the probability PW of the event for the stop $P_{2-2}$ of the moving window 2. The first difference DW, i.e., −0.1286, is calculated by subtracting the probability PW, i.e., 0.8166, of the event for the stop $P_{1-1}$ of the moving window 2 from the first probability guess PG, i.e., 0.6880. The second difference DW, i.e., 0.0260, is calculated by subtracting the probability PW, i.e., 0.5928, of the event for the stop $P_{1-2}$ of the moving window 2 from the second probability guess PG, i.e., 0.6188. The third difference DW, i.e., 0.1021, is calculated by subtracting the probability PW, i.e., 0.4407, of the event for the stop $P_{2-1}$ of the moving window 2 from the third probability guess PG, i.e., 0.5428. The fourth difference DW, i.e., 0.0004, is calculated by subtracting the probability PW, i.e., 0.5586, of the event for the stop $P_{2-2}$ from the fourth probability guess PG, i.e., 0.5590.

After the first through fourth differences DWs are obtained or calculated, the step S14 is performed to determine whether absolute values of the first through fourth differences DWs are less than or equal to a preset threshold value of 0.001. Because the absolute values of the first through third differences DWs are greater than the preset threshold value, the step S15 continues in which the probabilities PVs of the event for the computation voxels V1-V9 are updated, as shown in FIG. 11B.

In the step S15, because the only stop $P_{1-1}$ of the moving window 2 has the square 6a covering or overlapping the computation voxel V1, an error correction factor ECF, i.e., −0.03215, for the computation voxel V1 is obtained by calculating an error correction contribution only from the stop $P_{1-1}$ of the moving window 2. The error correction contribution to the computation voxel V1 from the stop $P_{1-1}$ of the moving window 2 is calculated by multiplying the first difference DW, i.e., −0.1286, for the stop $P_{1-1}$ of the moving window 2 by an area ratio, i.e., 1/4, of an overlapped area between the computation voxel V1 and the stop $P_{1-1}$ of the moving window 2 to an area of the square 4 inscribed in the stop $P_{1-1}$ of the moving window 2. Accordingly, the updated probability PV, i.e., 0.8488, of the event for the computation voxel V1 is calculated by subtracting the error correction factor ECF, i.e., −0.03215, for the computation voxel V1 from the probability PV, i.e., 0.8166, of the event for the computation voxel V1. Similarly, the updated probability PV, i.e., 0.5863, of the event for the computation voxel V3 is calculated by subtracting an error correction factor ECF, i.e., 0.0065, for the computation voxel V3 from the probability PV, i.e., 0.5928, of the event for the computation voxel V3, wherein the error correction factor ECF for the computation voxel V3 is obtained by calculating an error correction contribution only from the stop $P_{1-2}$ of the moving window 2. The error correction contribution to the computation voxel V3 from the stop $P_{1-2}$ of the moving window 2 is calculated by multiplying the second difference DW, i.e., 0.0260, for the stop $P_{1-2}$ of the moving window 2 by an area ratio, i.e., 1/4, of an overlapped area between the computation voxel V3 and the stop $P_{1-2}$ of the moving window 2 to an area of the square 4 inscribed in the stop $P_{1-2}$ of the moving window 2. The updated probability PV, i.e., 0.4152, of the event for the computation voxel V7 is calculated by subtracting an error correction factor ECF, i.e., 0.0255, for the computation voxel V7 from the probability PV, i.e., 0.4407, of the event for the computation voxel V7, wherein the error correction factor ECF for the computation voxel V7 is obtained by calculating an error correction contribution only from the stop $P_{2-1}$ of the moving window 2. The error correction contribution to the computation voxel V7 from the stop $P_{24}$ of the moving window 2 is calculated by multiplying the third difference DW, i.e., 0.1021, for the stop $P_{2-1}$ of the moving window 2 by an area ratio, i.e., 1/4, of an overlapped area between the computation voxel V7 and the stop $P_{2-1}$ of the moving window 2 to an area of the square 4 inscribed in the stop $P_{24}$ of the moving window 2. The updated probability PV, i.e., 0.5585, of the event for the computation voxel V9 is calculated by subtracting an error correction factor ECF, i.e., 0.0001, for the computation voxel V9 from the probability PV, i.e., 0.5586, of the event for the computation voxel V9, wherein the error correction factor ECF for the computation voxel V9 is obtained by calculating an error correction contribution only from the stop $P_{2-2}$ of the moving window 2. The error correction contribution to the computation voxel V9 from the stop $P_{2-2}$ of the moving window 2 is calculated by multiplying the fourth difference DW, i.e., 0.0004, for the stop $P_{2-2}$ of the moving window 2 by an area ratio, i.e., 1/4, of an overlapped area between the computation voxel V9 and the stop $P_{2-2}$ of the moving window 2 to an area of the square 4 inscribed in the stop $P_{2-2}$ of the moving window 2.

In addition, because the only two stops $P_{1-1}$ and $P_{1-2}$ of the moving window 2 have the squares 6b and 6e covering or overlapping the computation voxel V2, an error correction factor ECF, i.e., −0.02565, for the computation voxel V2 is obtained by summing error correction contributions from the respective stops $P_{1-1}$ and $P_{1-2}$ of the moving window 2. The error correction contribution to the computation voxel V2 from the stop $P_{1-1}$ of the moving window 2 is calculated by multiplying the first difference DW, i.e., −0.1286, for the stop $P_1$ of the moving window 2 by an area ratio, i.e., 1/4, of an overlapped area between the computation voxel V2 and the stop $P_{1-1}$ of the moving window 2 to the area of the square 4 inscribed in the stop $P_{1-1}$ of the moving window 2. The error correction contribution to the computation voxel V2 from the stop $P_{1-2}$ of the moving window 2 is calculated by multiplying the second difference DW, i.e., 0.0260, for the stop $P_{1-2}$ of the moving window 2 by an area ratio, i.e., 1/4, of an overlapped area between the computation voxel V2 and the stop $P_{1-2}$ of the moving window 2 to the area of the square 4 inscribed in the stop $P_{1-2}$ of the moving window 2. Accordingly, the updated probability PV, i.e., 0.7304, of the event for the computation voxel V2 is calculated by subtracting the error correction factor ECF, i.e., −0.02565, for the computation voxel V2 from the probability PV, i.e., 0.7047, of the event for the computation voxel V2. Similarly, the updated probability PV, i.e., 0.6352, of the event for the computation voxel V4 is calculated by subtracting an error correction factor ECF, i.e., −0.006625, for the computation voxel V4 from the probability PV, i.e., 0.6286, of the event for the computation voxel V4, wherein the error correction factor ECF for the computation voxel V4 is calculated by summing error correction contributions from the respective stops $P_{1-1}$ and $P_{2-1}$ of the moving window 2. The error correction contribution to the computation voxel V4 from the stop $P_{1-1}$ of the moving window 2 is calculated by multiplying the first difference DW, i.e., −0.1286, for the stop $P_{1-1}$ of the moving window 2 by an area ratio, i.e., 1/4, of an overlapped area between the computation voxel V4 and the stop $P_{1-1}$ of the moving window 2 to the area of the square 4 inscribed in the stop $P_{1-1}$ of the moving window 2. The error correction contribution to the computation voxel V4 from the stop $P_{2-1}$ of the moving window 2 is calculated by multiplying the third difference DW, i.e., 0.1021, for the stop $P_{2-1}$ of the moving window 2 by an area ratio, i.e., 1/4, of an overlapped area between the computation voxel V4 and the stop $P_2$ of the moving window 2 to the area of the square 4 inscribed in the stop $P_{2-1}$ of the moving window 2. The updated probability PV, i.e., 0.5691, of the event for the computation voxel V6 is calculated by subtracting an error correction factor ECF, i.e., 0.0066, for the computation voxel V6 from the probability PV, i.e., 0.5757, of the event for the computation voxel V6, wherein the error correction factor ECF for the computation voxel V6 is calculated by summing error correction contributions from the respective stops $P_{1-2}$ and $P_{2-2}$ of the moving window 2. The error correction contribution to the computation voxel V6 from the stop $P_{1-2}$ of the moving window 2 is calculated by multiplying the second difference DW, i.e., 0.0260, for the stop $P_{1-2}$ of the moving window 2 by an area ratio, i.e., 1/4, of an overlapped area between the computation voxel V6 and the stop $P_{1-2}$ of the moving window 2 to the area of the square 4 inscribed in the stop $P_{1-2}$ of the moving window 2. The error correction contribution to the computation voxel V6 from the stop $P_{2-2}$ of the moving window 2 is calculated by multiplying the fourth difference DW, i.e., 0.0004, for the stop $P_{2-2}$ of the moving window 2 by an area ratio, i.e., 1/4, of an overlapped area between the computation voxel V6 and the stop $P_{2-2}$ of the moving window 2 to the area of the square 4 inscribed in the stop $P_{2-2}$ of the moving window 2. The updated probability PV, i.e., 0.4740, of the event for the computation voxel V8 is calculated by subtracting an error correction factor ECF, i.e., 0.025625, for the computation voxel V8 from the probability PV, i.e., 0.4996, of the event for the computation voxel V8, wherein the error correction factor ECF for the computation voxel V8 is calculated by summing error correction contributions from the respective stops $P_{2-1}$ and $P_{2-2}$ of the moving window 2. The error correction contribution to the computation voxel V8 from the stop $P_{2-1}$ of the moving window 2 is calculated by multiplying the third difference DW, i.e., 0.1021, for the stop $P_{2-1}$ of the moving window 2 by an area ratio, i.e., 1/4, of an overlapped area between the computation voxel V8 and the stop $P_2$ of the moving window 2 to the area of the square 4 inscribed in the stop $P_{2-1}$ of the moving window 2. The error correction contribution to the computation voxel V8 from the stop $P_{2-2}$ of the moving window 2 is calculated by multiplying the fourth difference DW, i.e., 0.0004, for the stop $P_{2-2}$ of the moving window 2 by an area ratio, i.e., 1/4, of an overlapped area between the computation voxel V8 and the stop $P_{2-2}$ of the moving window 2 to the area of the square 4 inscribed in the stop $P_{2-2}$ of the moving window 2.

Because the only four stops $P_{1-1}$, $P_{1-2}$, $P_{2-1}$ and $P_{2-2}$ of the moving window 2 have the squares 6d, 6g, 6j and 6m covering or overlapping the computation voxel V5, an error correction factor ECF, i.e., −0.000025, for the computation voxel V5 is obtained by summing error correction contributions from the respective stops $P_{1-1}$, $P_{1-2}$, $P_{2-1}$ and $P_{2-2}$ of the moving window 2. The error correction contribution to the computation voxel V5 from the stop $P_{1-1}$ of the moving window 2 is calculated by multiplying the first difference DW, i.e., −0.1286, for the stop $P_{1-1}$ of the moving window 2 by an area ratio, i.e., 1/4, of an overlapped area between the computation voxel V5 and the stop $P_{1-1}$ of the moving window 2 to the area of the square 4 inscribed in the stop $P_{1-1}$ of the moving window 2. The error correction contribution to the computation voxel V5 from the stop $P_{1-2}$ of the moving window 2 is calculated by multiplying the second difference DW, i.e., 0.0260, for the stop $P_{1-2}$ of the moving window 2 by an area ratio, i.e., 1/4, of an overlapped area between the computation voxel V5 and the stop $P_{1-2}$ of the moving window 2 to the area of the square 4 inscribed in the stop $P_{1-2}$ of the moving window 2. The error correction contribution to the computation voxel V5 from the stop $P_{2-1}$ of the moving window 2 is calculated by multiplying the third difference DW, i.e., 0.1021, for the stop $P_{2-1}$ of the moving window 2 by an area ratio, i.e., 1/4, of an overlapped area between the computation voxel V5 and the stop $P_{2-1}$ of the moving window 2 to the area of the square 4 inscribed in the stop $P_{2-1}$ of the moving window 2. The error correction contribution to the computation voxel V5 from the stop $P_{2-2}$ of the moving window 2 is calculated by multiplying the fourth difference DW, i.e., 0.0004, for the stop $P_{2-2}$ of the moving window 2 by an area ratio, i.e., 1/4, of an overlapped area between the computation voxel V5 and the stop $P_{2-2}$ of the moving window 2 to the area of the square 4 inscribed in the stop $P_{2-2}$ of the moving window 2. Accordingly, the updated probability PV, i.e., 0.6022, of the event for the computation voxel V5 is calculated by subtracting the error correction factor ECF, i.e., −0.000025, for the computation voxel V5 from the probability PV, i.e., 0.6022, of the event for the computation voxel V5.

After the updated probabilities PVs of the event for the computation voxels V1-V9 are obtained or calculated, the steps S12-S15 are performed repeatedly based on the updated probabilities PVs of the event for the computation voxels V1-V9 in the step S15, until the absolute values of the first through fourth differences DWs are less than or equal to the preset threshold value. Accordingly, the optimal probabilities of the event for the computation voxels V1-V9, as shown in FIG. 11C, are obtained and form the probability map for the event.

Figure 12:
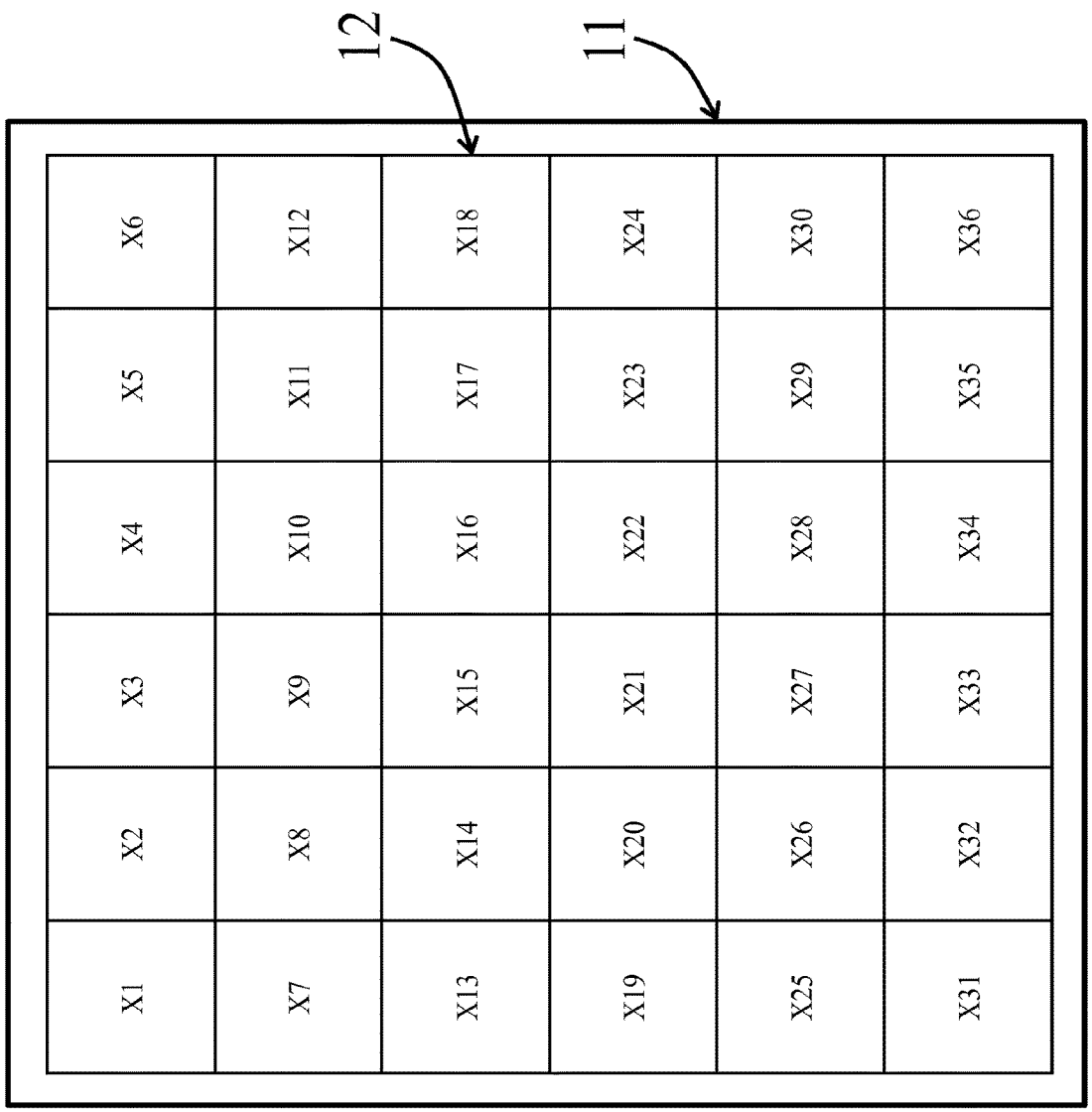
FIG. 12 shows a computation region defined with thirty-six computation voxels for a probability map in accordance with an embodiment of the present invention.

In an alternative example, the square 4 inscribed in the moving window 2 with the radius Rm is divided into, e.g., nine small squares 6 each having width Wsq as shown in FIG. 3B, and in the step S2, the computation region 12 for the probability map is defined with, e.g., 36 computation voxels X1 through X36 as shown in FIG. 12 based on the width Wsq of the nine small squares 6 in the moving window 2. Each of the 36 computation voxels X1-X36 used to compose the probability map is defined as a square with the width Wsq. Next, referring to FIGS. 13B, 13D, 13F, 13H, 14B, 14D, 14F, 14H, 15B, 15D, 15F, 15H, 16B, 16D, 16F, and 16H, the moving window 2 moves across the computation region 12 at a regular step or interval of a fixed distance in the x and y directions, and measures of the specific MRI parameters for sixteen stops $P_{1-1}$, $P_{1-2}$, $P_{1-3}$, $P_{1-4}$, $P_{2-1}$, $P_{2-2}$, $P_{2-3}$, $P_{2-4}$, $P_{3-1}$, $P_{3-2}$, $P_{3-3}$, $P_{3-4}$, $P_{4-1}$, $P_{4-2}$, $P_{4-3}$, and $P_{4-4}$ of the moving window 2 are obtained from the MRI image 10 or the registered imaging dataset. In the example, the fixed distance is substantially equal to the width Wsq.

Figure 13B:
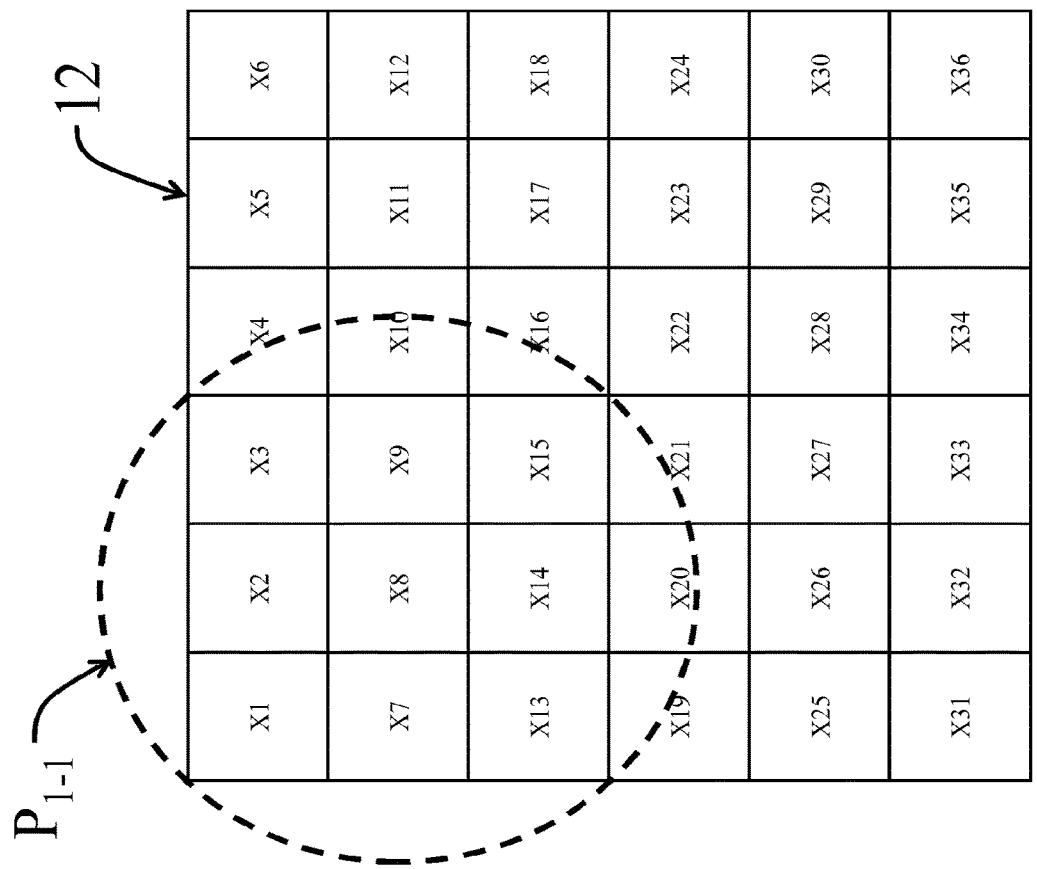
Figure 13A:
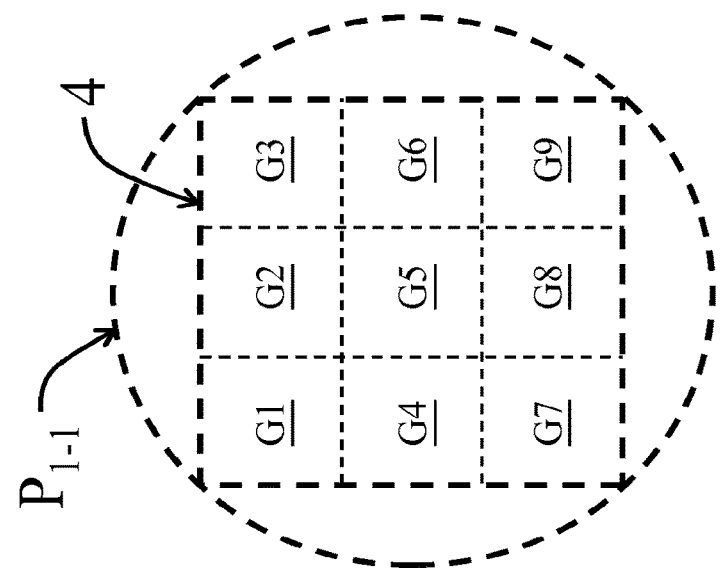
Figure 13F:
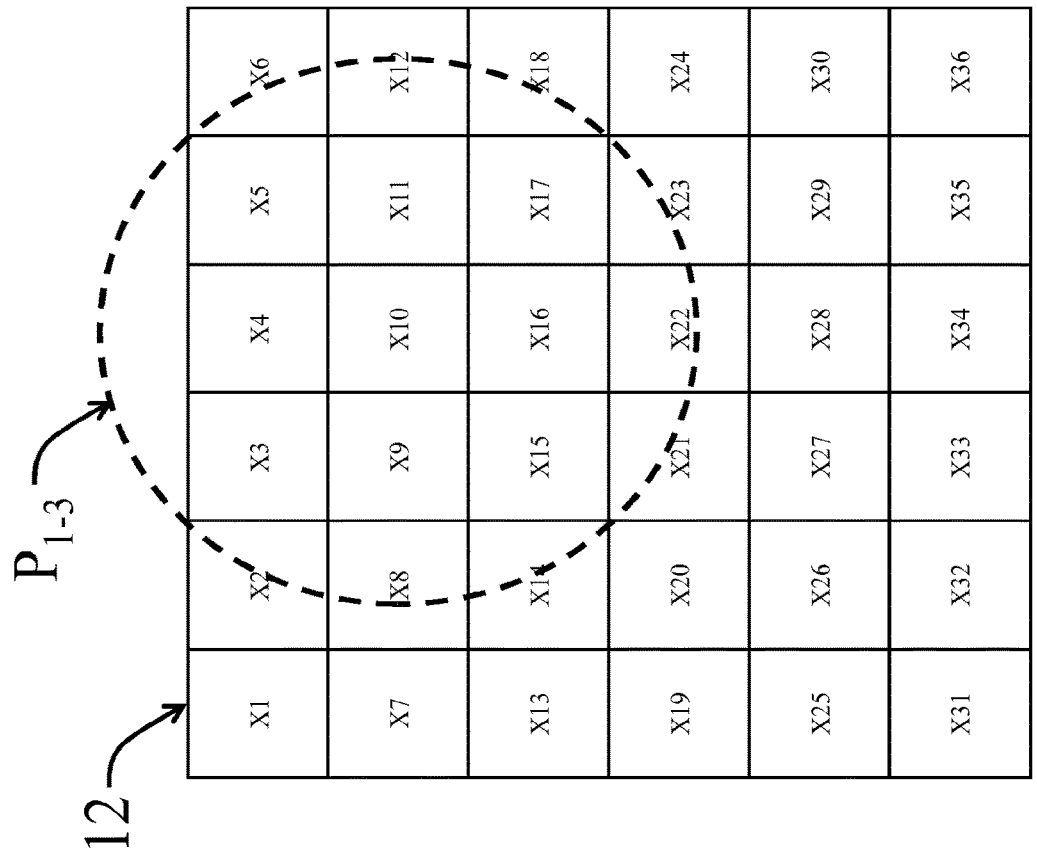
Figure 13E:
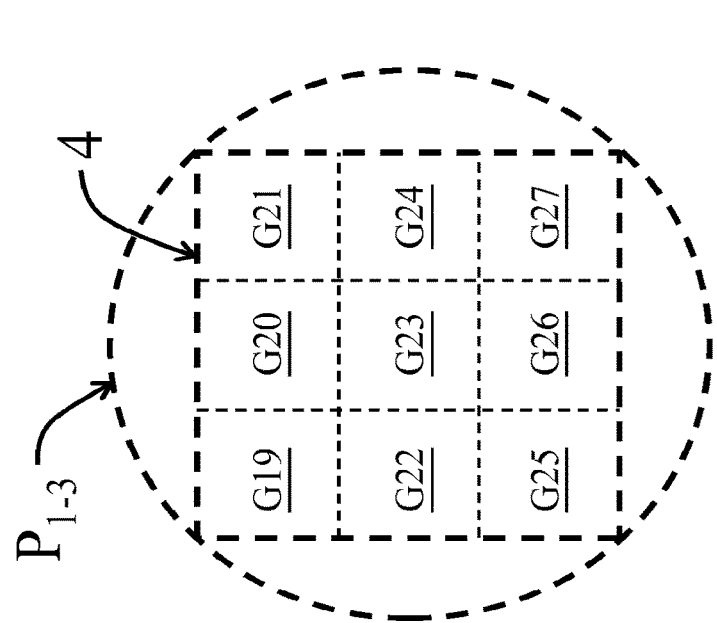
Figure 13H:
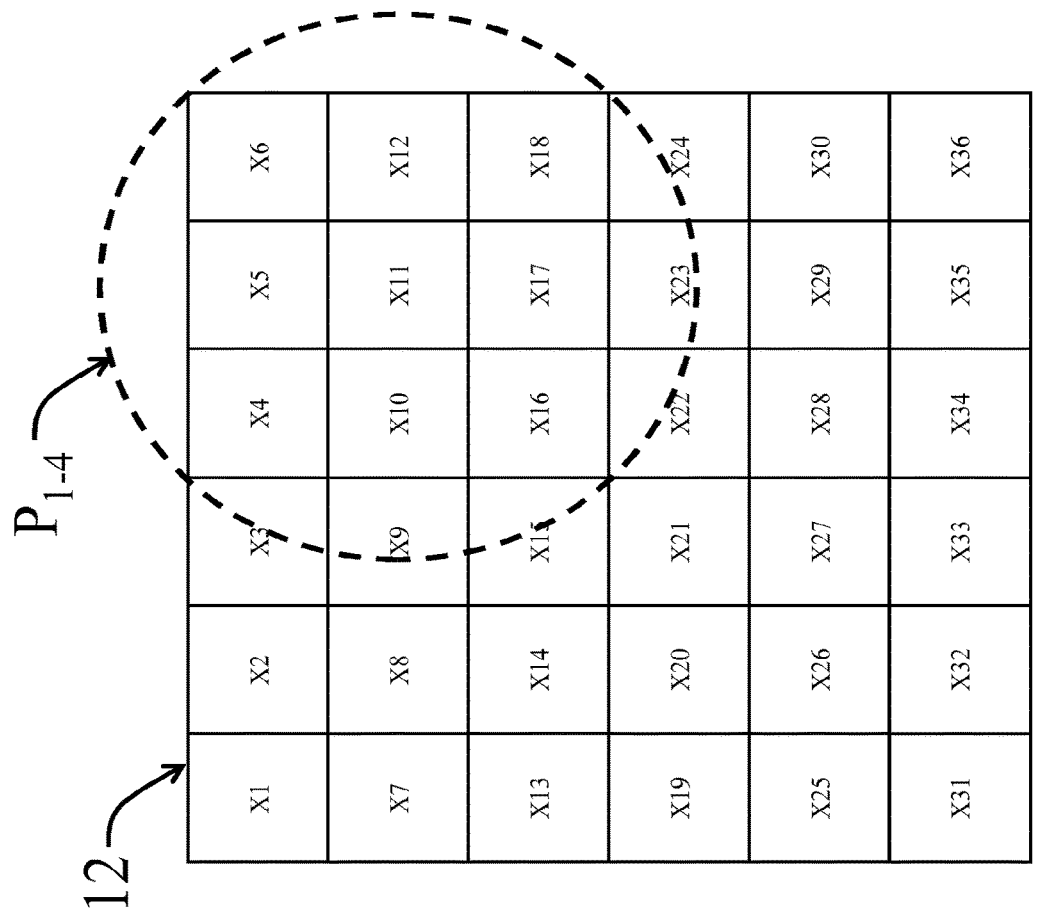
Figure 13G:
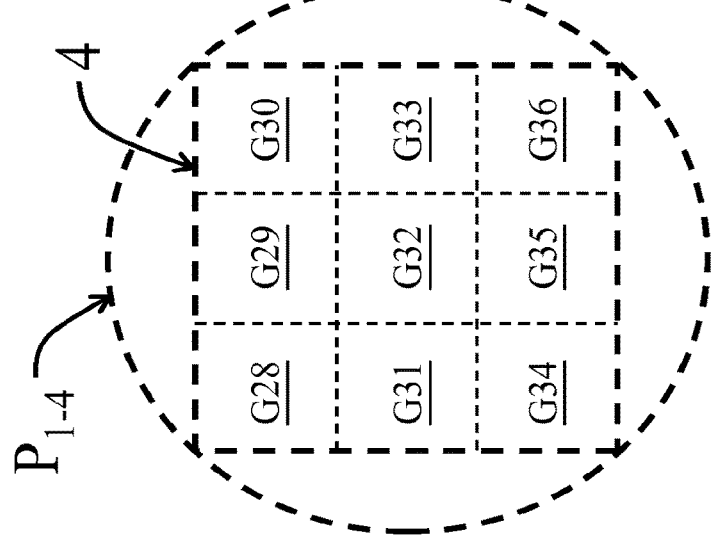

Referring to FIGS. 13A and 13B, nine small squares G1 through G9, i.e., the nine squares 6, within the square 4 inscribed in the stops $P_{1-1}$ of the moving window 2 overlap or cover the nine computation voxels X1, X2, X3, X7, X8, X9, X13, X14 and X15, respectively, and each of the squares G1-G9 may have an area less than 10% of that of the stop $P_{1-1}$ of the moving window 2. For details about the squares G1-G9, please refer to the squares 6 illustrated in FIG. 3B. Referring to FIGS. 13C and 13D, nine small squares G10 through G18, i.e., the nine squares 6, within the square 4 inscribed in the stop $P_{1-2}$ of the moving window 2 overlap or cover the nine computation voxels X2, X3, X4, X8, X9, X10, X14, X15 and X16, respectively, and each of the squares G10-G18 may have an area less than 10% of that of the stop $P_{1-2}$ of the moving window 2. For details about the squares G10-G18, please refer to the squares 6 illustrated in FIG. 3B. Referring to FIGS. 13E and 13F, nine small squares G19 through G27, i.e., the nine squares 6, within the square 4 inscribed in the stop $P_{1-3}$ of the moving window 2 overlap or cover the nine computation voxels X3, X4, X5, X9, X10, X11, X15, X16 and X17, respectively, and each of the squares G19-G27 may have an area less than 10% of that of the stop $P_{1-3}$ of the moving window 2. For details about the squares G19-G27, please refer to the squares 6 illustrated in FIG. 3B. Referring to FIGS. 13G and 13H, nine small squares G28 through G36, i.e., the nine squares 6, within the square 4 inscribed in the stop $P_{1-4}$ of the moving window 2 overlap or cover the nine computation voxels X4, X5, X6, X10, X11, X12, X16, X17 and X18, respectively, and each of the squares G28-G36 may have an area less than 10% of that of the stop $P_{1-4}$ of the moving window 2. For details about the squares G28-G36, please refer to the squares 6 illustrated in FIG. 3B.

Figures 14A, 14B:
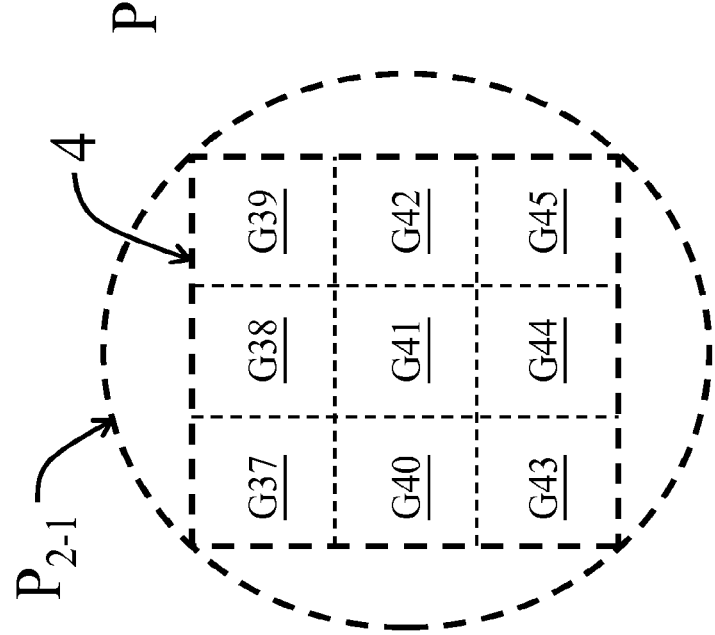
Figures 14C, 14D:
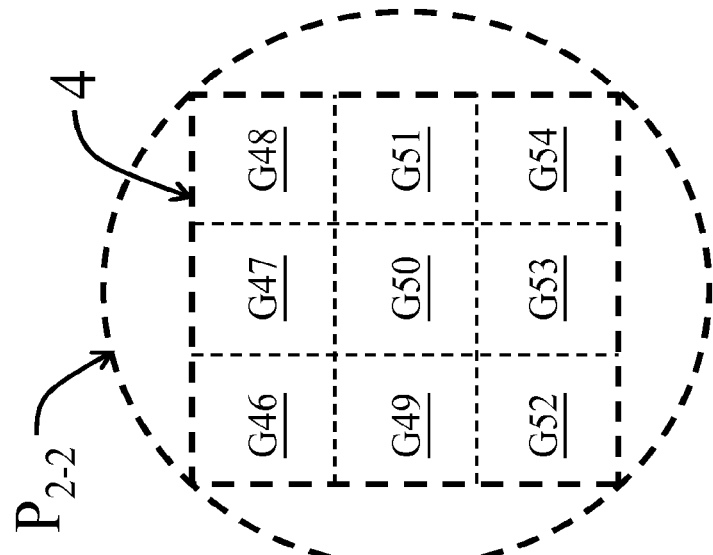
Figures 14E, 14F:
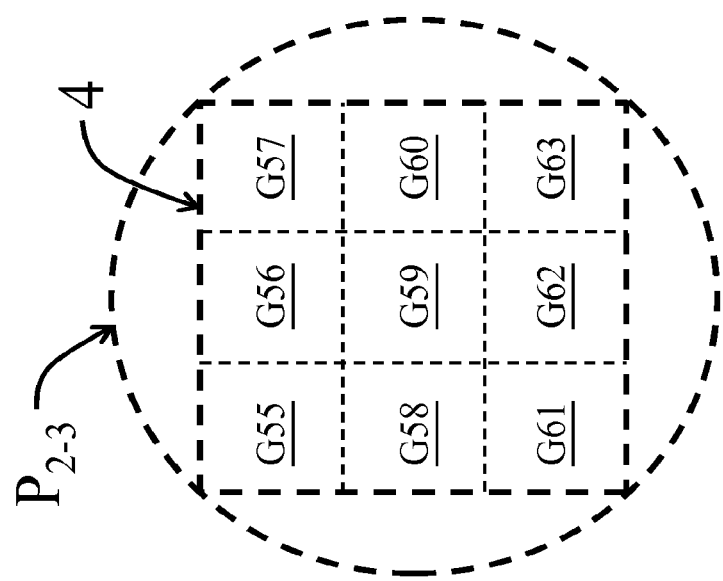
Figure 14H:
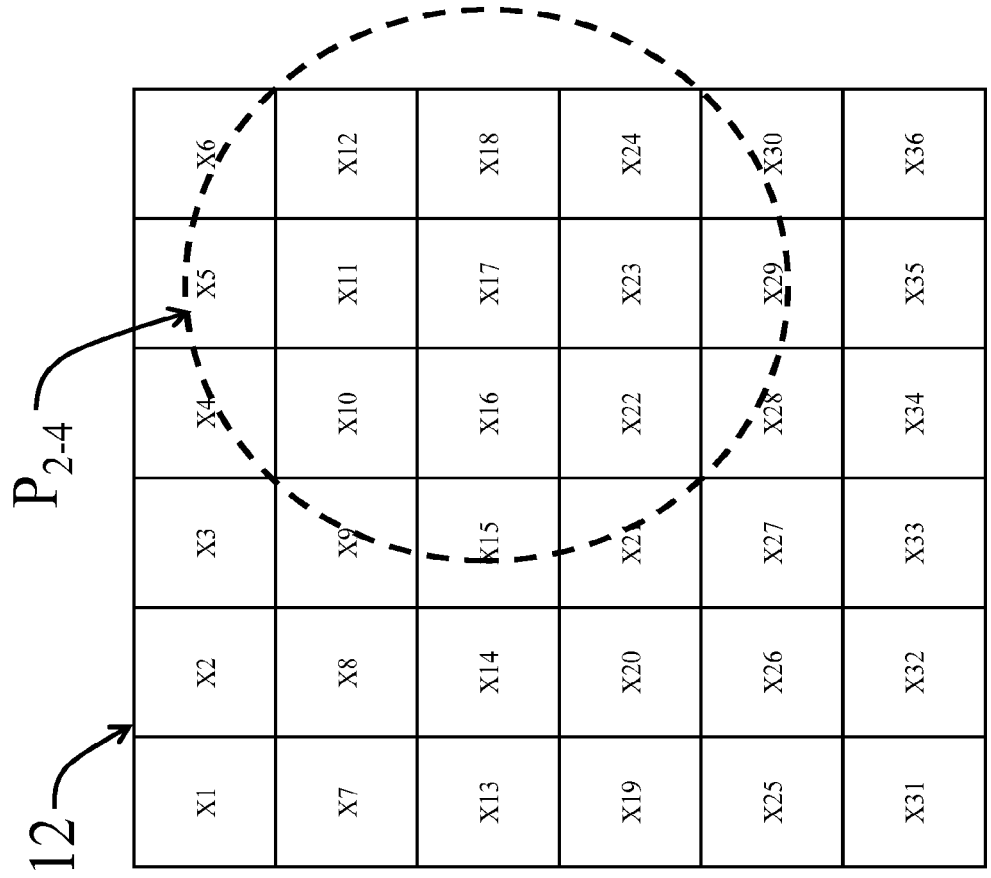
Figure 14G:
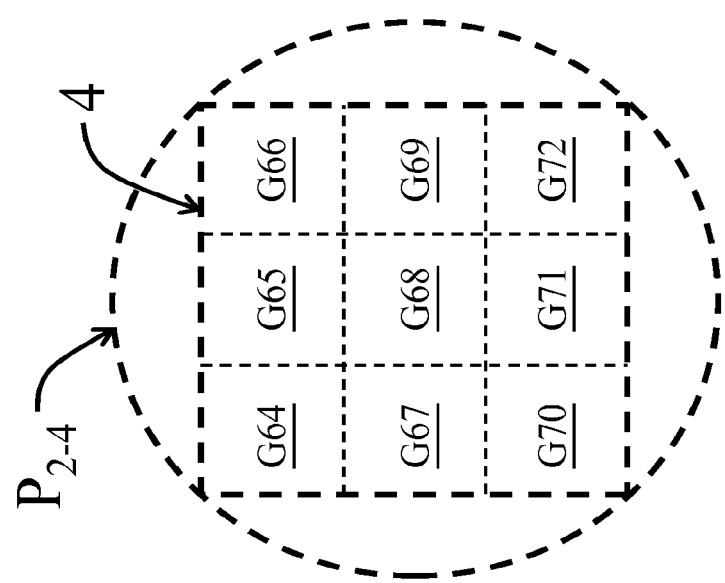

Referring to FIGS. 14A and 14B, nine small squares G37 through G45, i.e., the nine squares 6, within the square 4 inscribed in the stop $P_{2-1}$ of the moving window 2 overlap or cover the nine computation voxels X7, X8, X9, X13, X14, X15, X19, X20 and X21, respectively, and each of the squares G37-G45 may have an area less than 10% of that of the stop $P_{2-1}$ of the moving window 2. For details about the squares G37-G45, please refer to the squares 6 illustrated in FIG. 3B. Referring to FIGS. 14C and 14D, nine small squares G46 through G54, i.e., the nine squares 6, within the square 4 inscribed in the stop $P_{2-2}$ of the moving window 2 overlap or cover the nine computation voxels X8, X9, X10, X14, X15, X16, X20, X21 and X22, respectively, and each of the squares G46-G54 may have an area less than 10% of that of the stop $P_{2-2}$ of the moving window 2. For details about the squares G46-G54, please refer to the squares 6 illustrated in FIG. 3B. Referring to FIGS. 14E and 14F, nine small squares G55 through G63, i.e., the nine squares 6, within the square 4 inscribed in the stop $P_{2-3}$ of the moving window 2 overlap or cover the nine computation voxels X9, X10, X11, X15, X16, X17, X21, X22 and X23, respectively, and each of the squares G55-G63 may have an area less than 10% of that of the stop $P_{2-3}$ of the moving window 2. For details about the squares G55-G63, please refer to the squares 6 illustrated in FIG. 3B. Referring to FIGS. 14G and 14H, nine small squares G64 through G72, i.e., the nine squares 6, within the square 4 inscribed in the stop $P_{2-4}$ of the moving window 2 overlap or cover the nine computation voxels X10, X11, X12, X16, X17, X18, X22, X23 and X24, respectively, and each of the squares G64-G72 may have an area less than 10% of that of the stop $P_{2-4}$ of the moving window 2. For details about the squares G64-G72, please refer to the squares 6 illustrated in FIG. 3B.

Figures 15A, 15B:
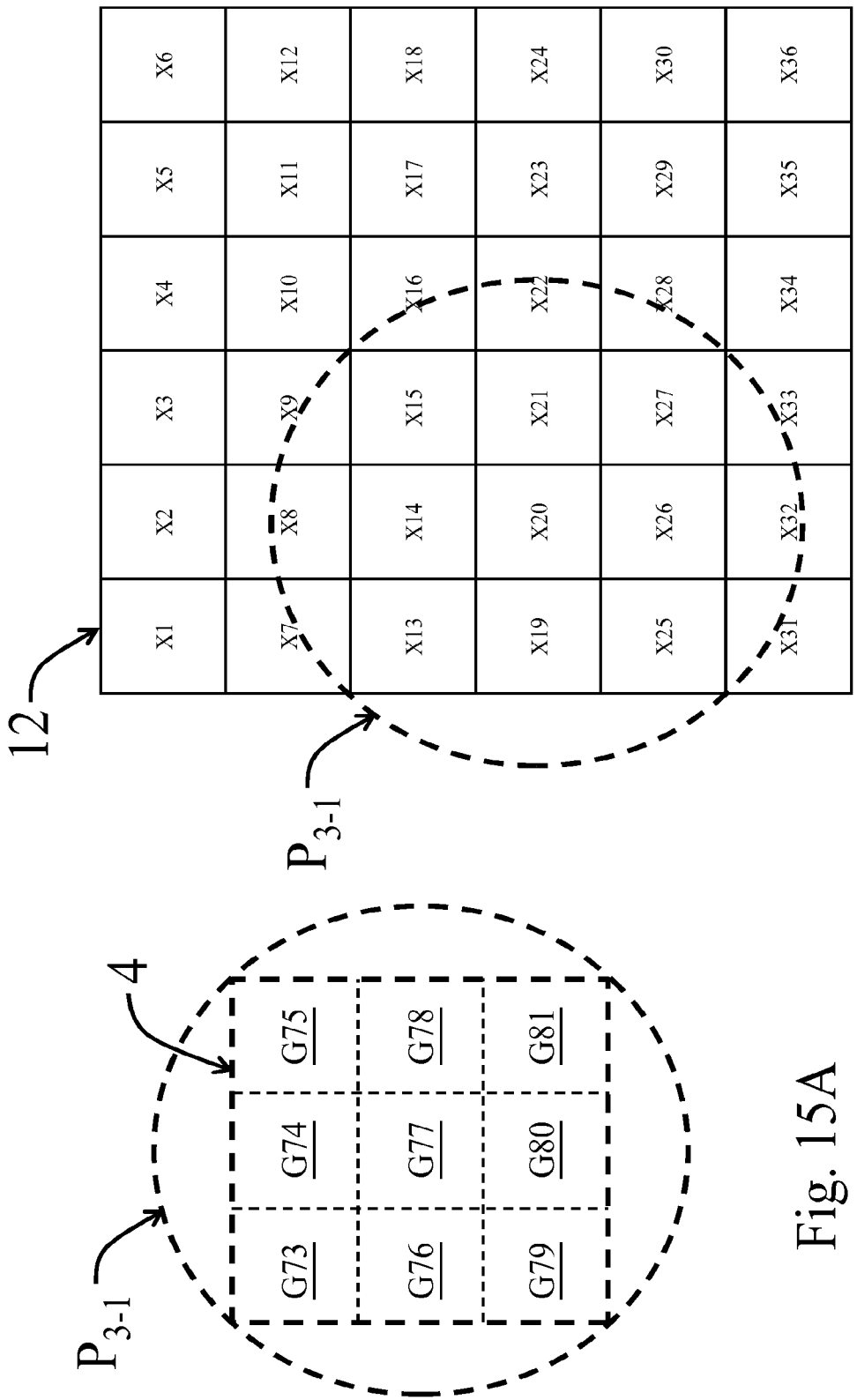
Figure 15D:
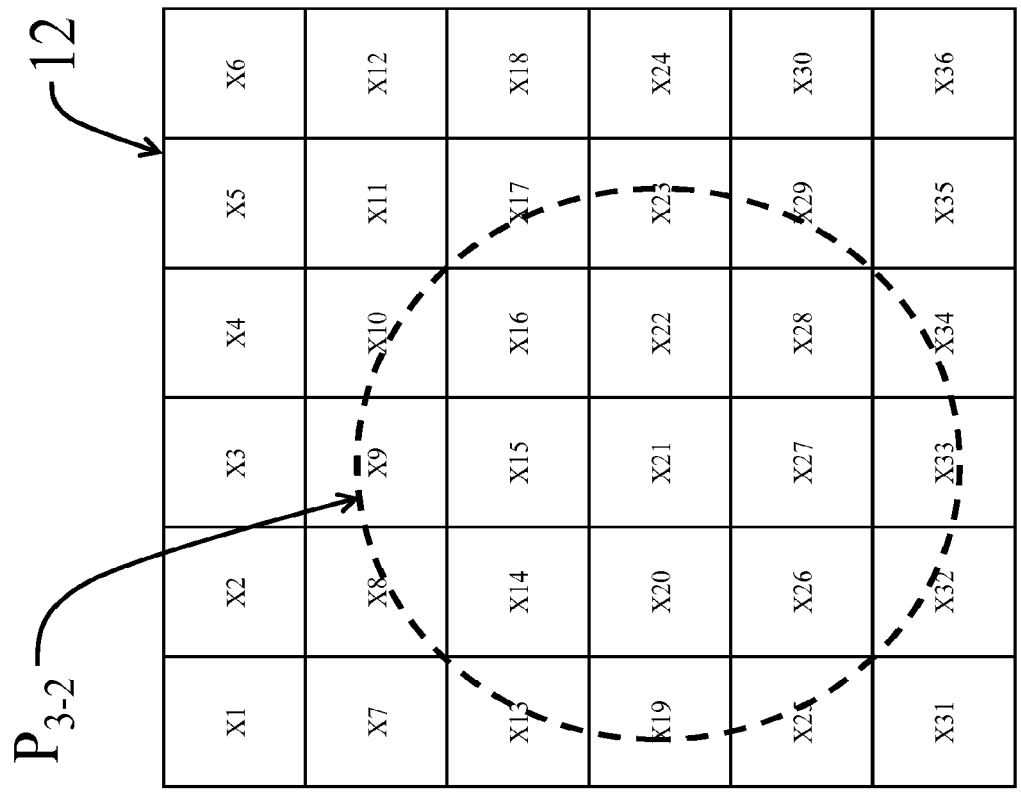
Figure 15C:
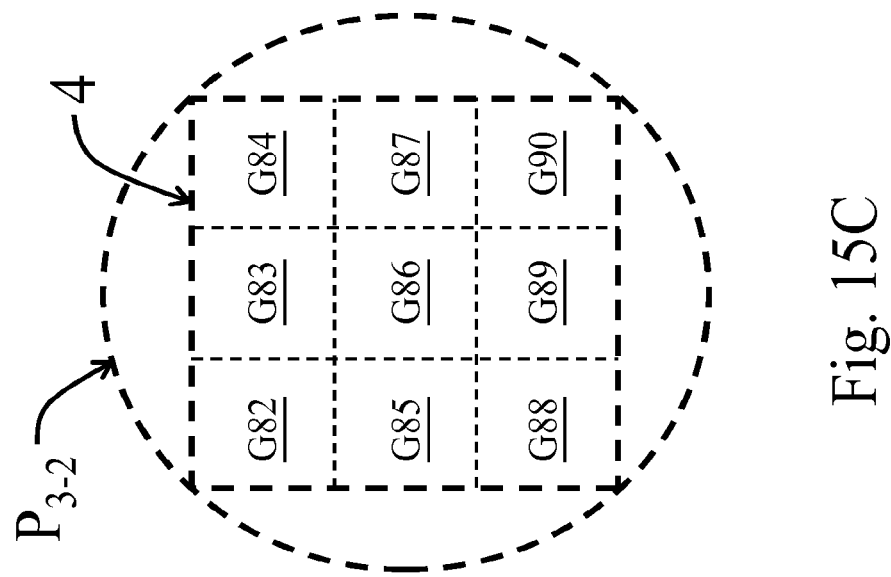
Figure 15F:
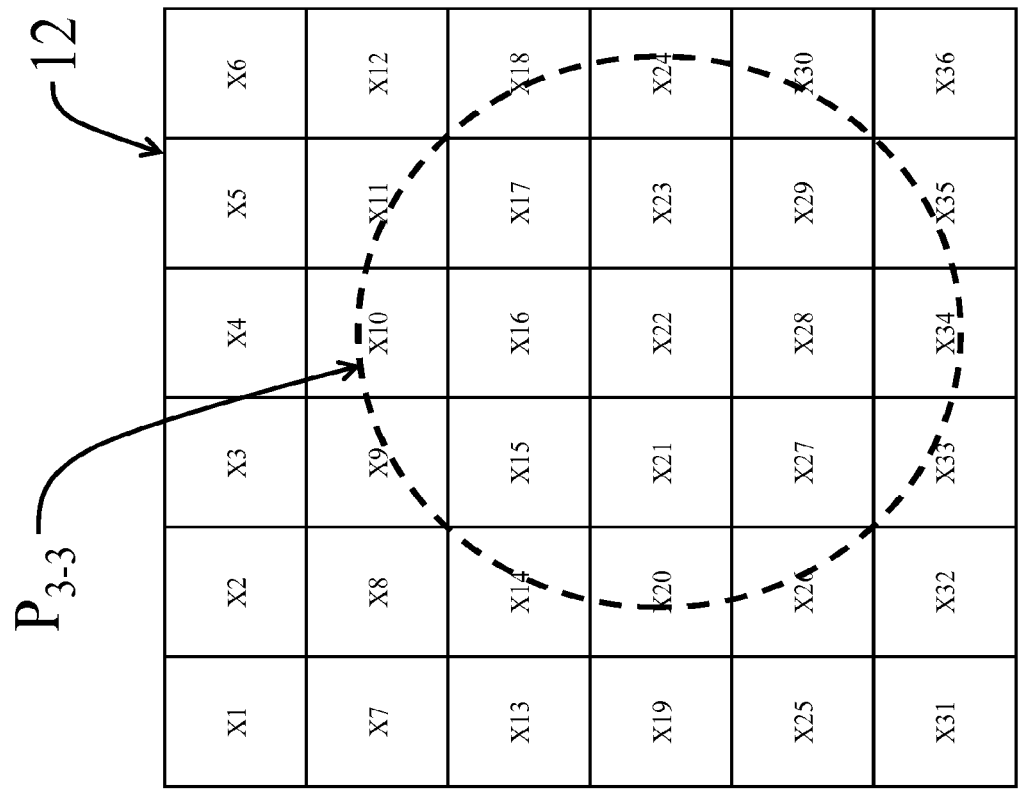
Figure 15E:
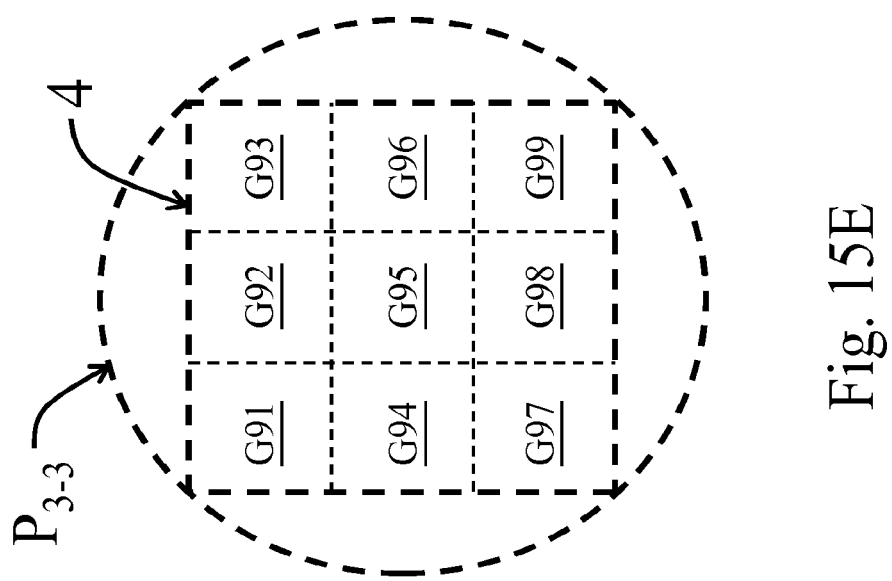
Figures 15G, 15H:
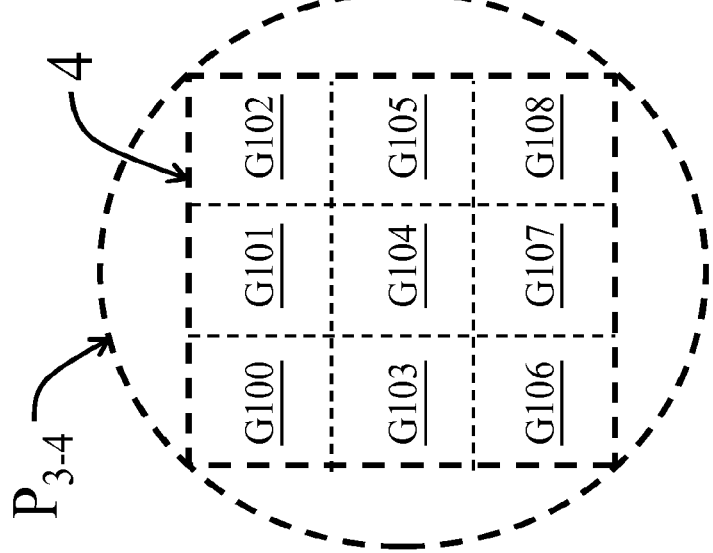

Referring to FIGS. 15A and 15B, nine small squares G73 through G81, i.e., the nine squares 6, within the square 4 inscribed in the stop $P_{3-1}$ of the moving window 2 overlap or cover the nine computation voxels X13, X14, X15, X19, X20, X21, X25, X26 and X27, respectively, and each of the squares G73-G81 may have an area less than 10% of that of the stop $P_{3-1}$ of the moving window 2. For details about the squares G73-G81, please refer to the squares 6 illustrated in FIG. 3B. Referring to FIGS. 15C and 15D, nine small squares G82 through G90, i.e., the nine squares 6, within the square 4 inscribed in the stop $P_{3-2}$ of the moving window 2 overlap or cover the nine computation voxels X14, X15, X16, X20, X21, X22, X26, X27 and X28, respectively, and each of the squares G82-G90 may have an area less than 10% of that of the stop $P_{3-2}$ of the moving window 2. For details about the squares G82-G90, please refer to the squares 6 illustrated in FIG. 3B. Referring to FIGS. 15E and 15F, nine small squares G91 through G99, i.e., the nine squares 6, within the square 4 inscribed in the stop $P_{3-3}$ of the moving window 2 overlap or cover the nine computation voxels X15, X16, X17, X21, X22, X23, X27, X28 and X29, respectively, and each of the squares G91-G99 may have an area less than 10% of that of the stop $P_{3-3}$ of the moving window 2. For details about the squares G91-G99, please refer to the squares 6 illustrated in FIG. 3B. Referring to FIGS. 15G and 15H, nine small squares G100 through G108, i.e., the nine squares 6, within the square 4 inscribed in the stop $P_{3-4}$ of the moving window 2 overlap or cover the nine computation voxels X16, X17, X18, X22, X23, X24, X28, X29 and X30, respectively, and each of the squares G100-G108 may have an area less than 10% of that of the stop $P_{3-4}$ of the moving window 2. For details about the squares G100-G108, please refer to the squares 6 illustrated in FIG. 3B.

Figures 16A, 16B:
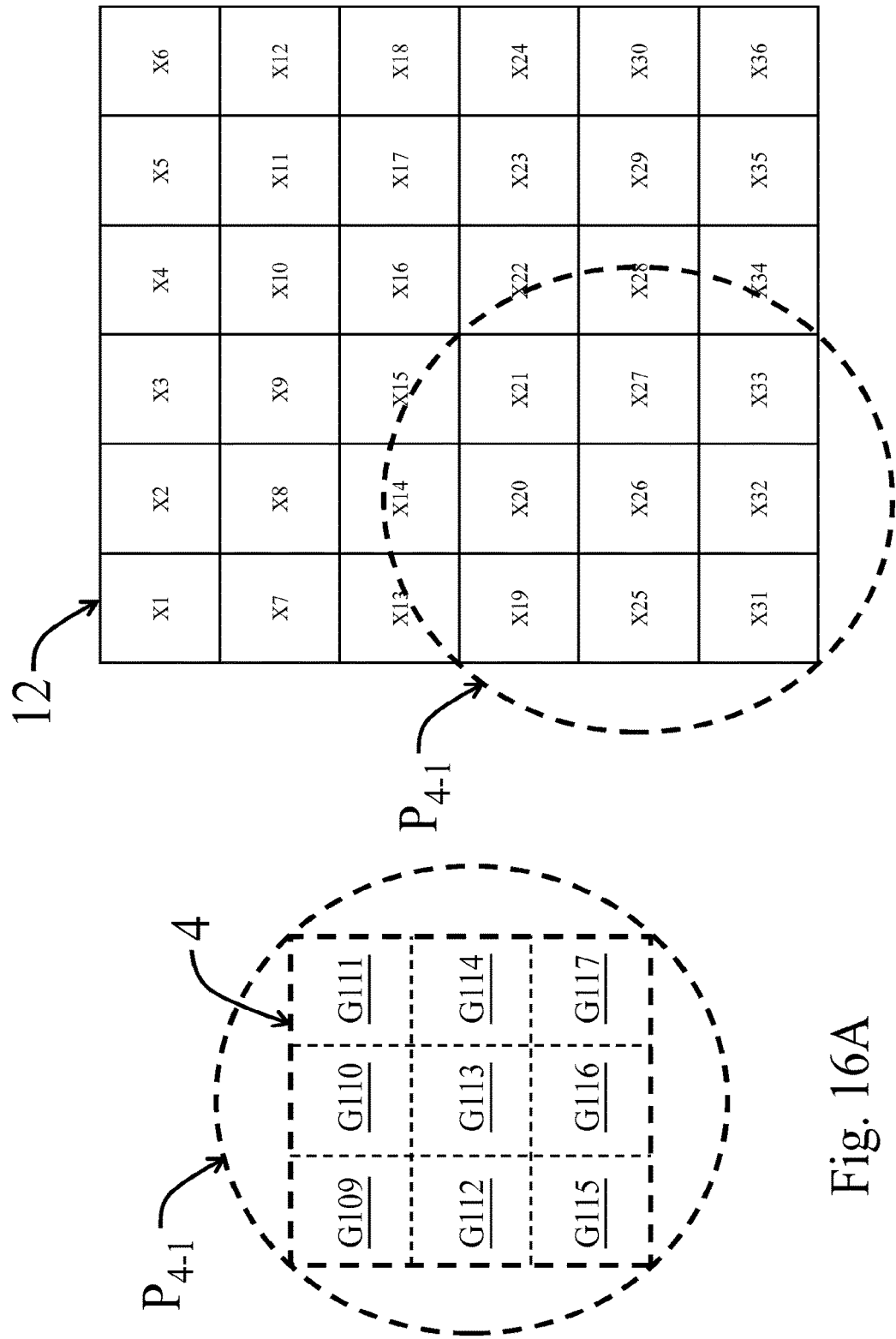
Figure 16D:
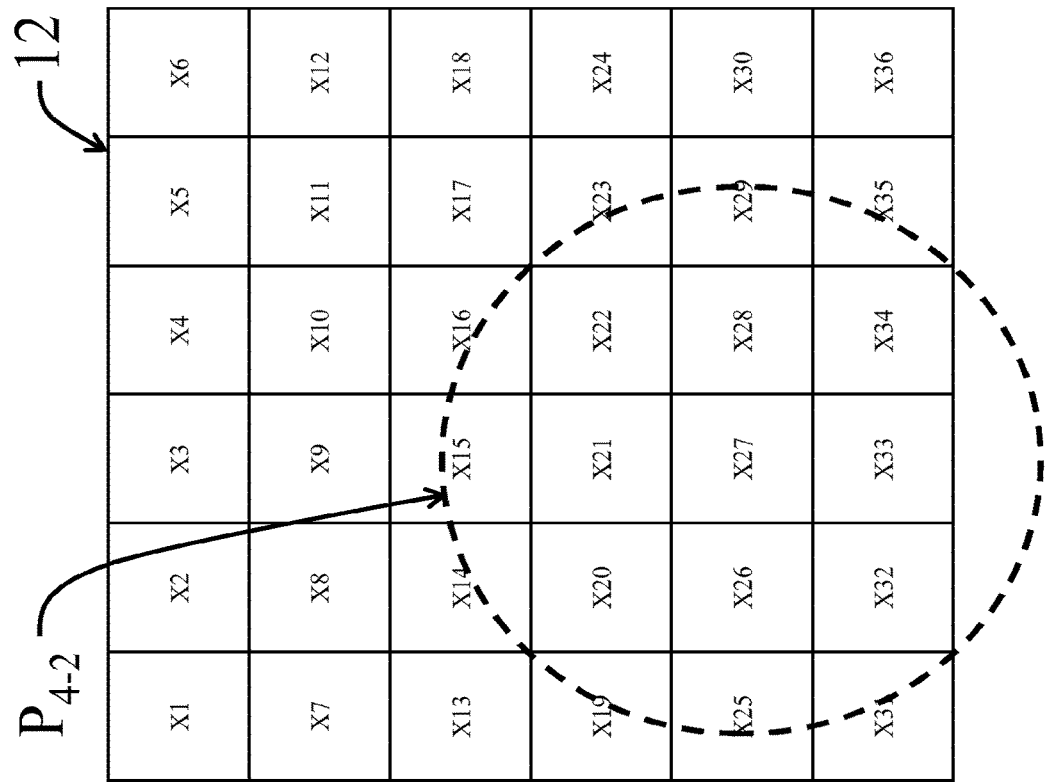
Figure 16C:
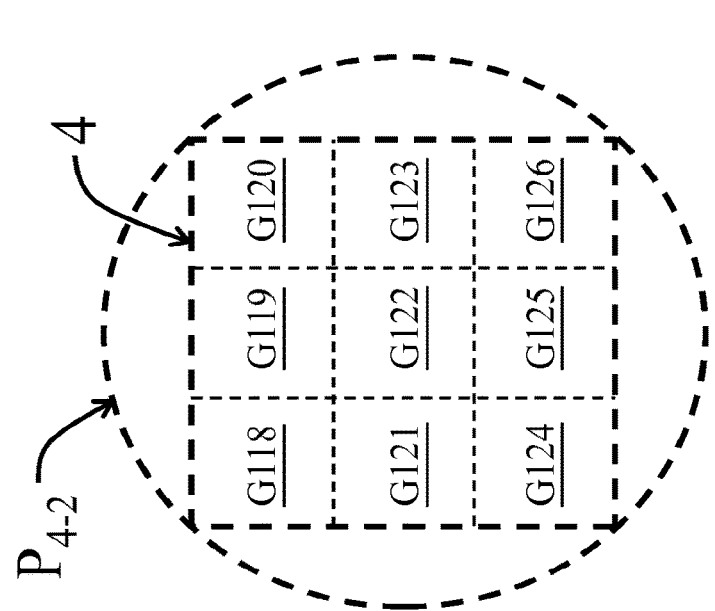
Figure 16F:
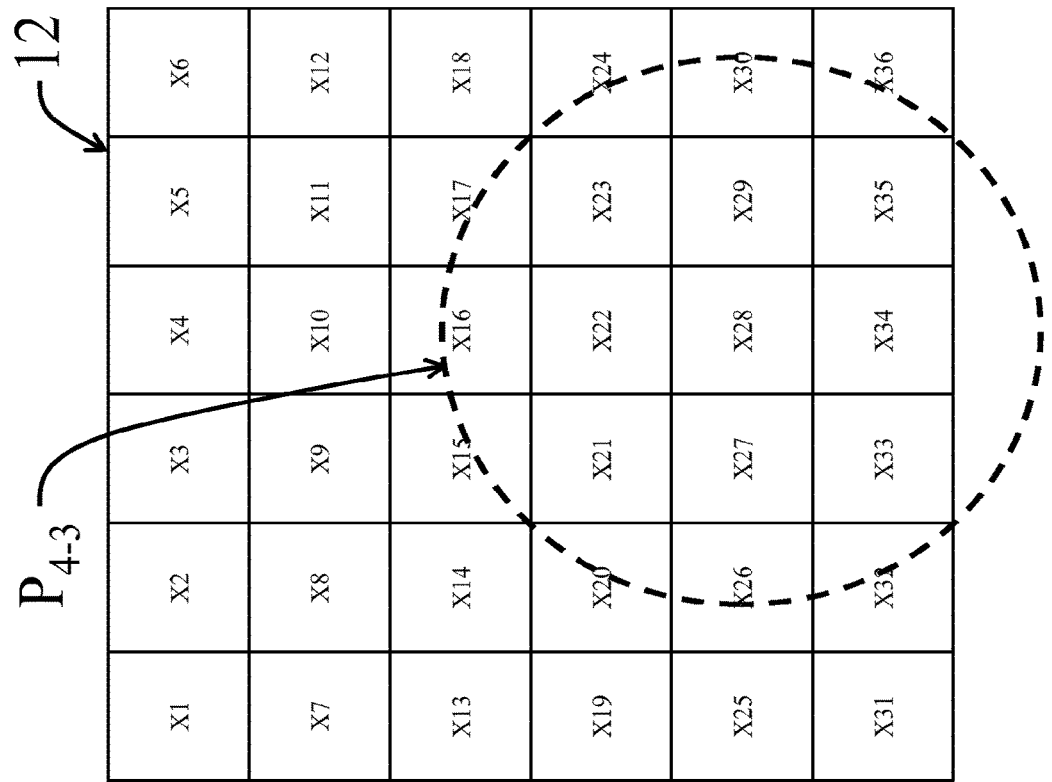
Figure 16E:
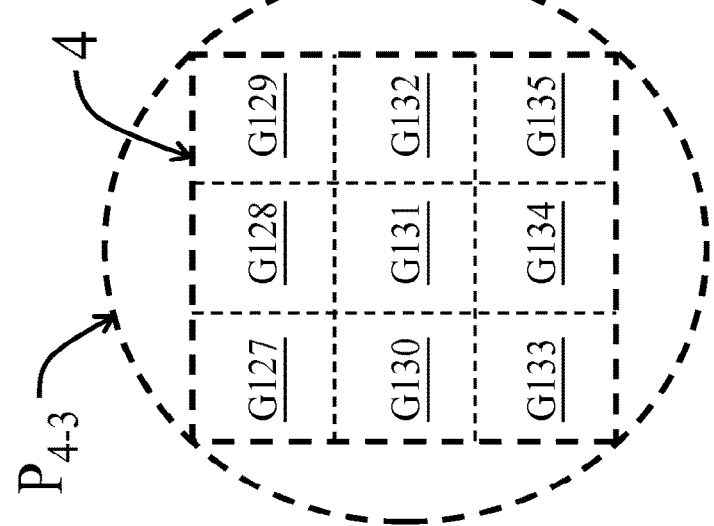
Figure 16H:
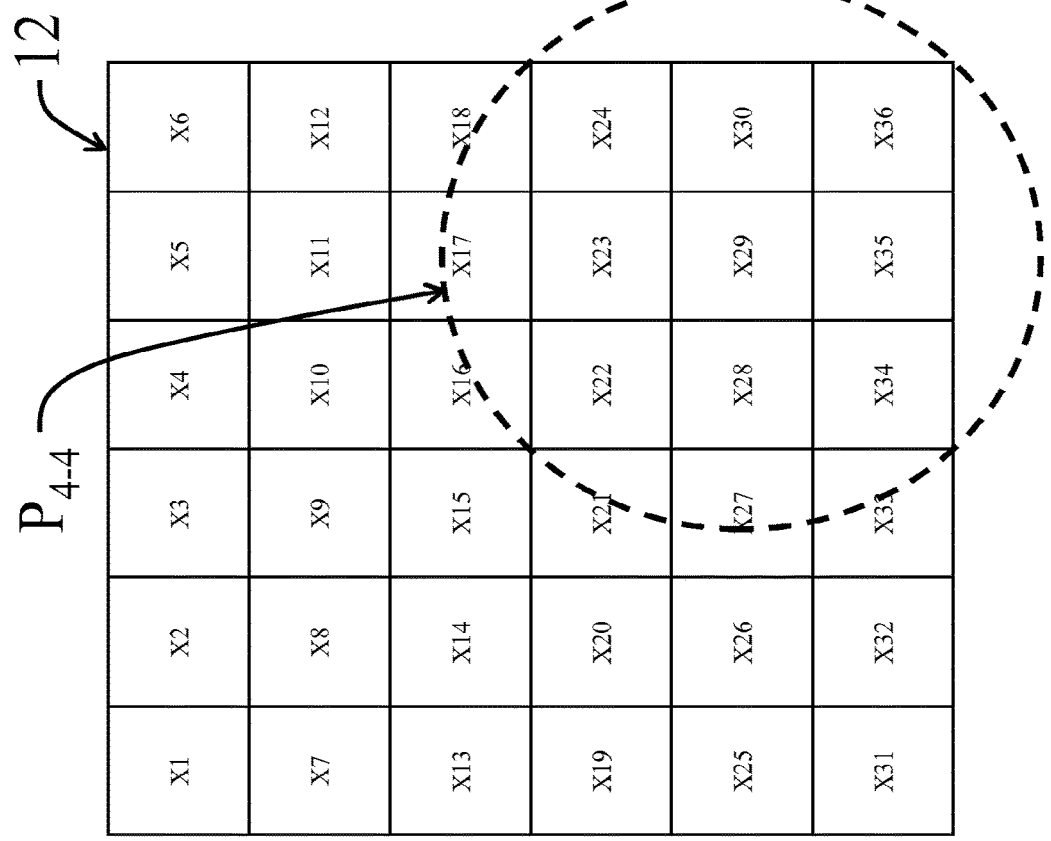
Figure 16G:
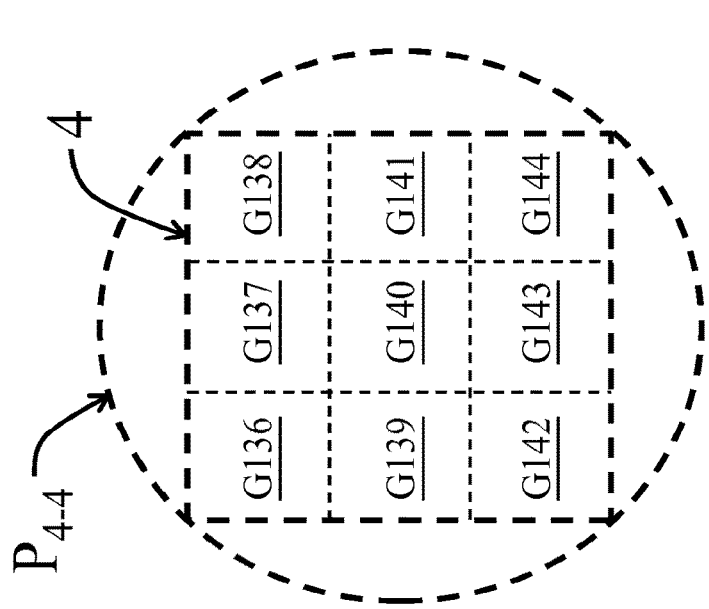

Referring to FIGS. 16A and 16B, nine small squares G109 through G117, i.e., the nine squares 6, within the square 4 inscribed in the stop $P_{4-1}$ of the moving window 2 overlap or cover the nine computation voxels X19, X20, X21, X25, X26, X27, X31, X32 and X33, respectively, and each of the squares G109-G117 may have an area less than 10% of that of the stop $P_{4-1}$ of the moving window 2. For details about the squares G109-G117, please refer to the squares 6 illustrated in FIG. 3B. Referring to FIGS. 16C and 16D, nine small squares G118 through G126, i.e., the nine squares 6, within the square 4 inscribed in the stop $P_{4-2}$ of the moving window 2 overlap or cover the nine computation voxels X20, X21, X22, X26, X27, X28, X32, X33 and X34, respectively, and each of the squares G118-G126 may have an area less than 10% of that of the stop $P_{4-2}$ of the moving window 2. For details about the squares G118-G126, please refer to the squares 6 illustrated in FIG. 3B. Referring to FIGS. 16E and 16F, nine small squares G127 through G135, i.e., the nine squares 6, within the square 4 inscribed in the stop $P_{4-3}$ of the moving window 2 overlap or cover the nine computation voxels X21, X22, X23, X27, X28, X29, X33, X34 and X35, respectively, and each of the squares G127-G135 may have an area less than 10% of that of the stop $P_{4-3}$ of the moving window 2. For details about the squares G127-G135, please refer to the squares 6 illustrated in FIG. 3B. Referring to FIGS. 16G and 16H, nine small squares G136 through G144, i.e., the nine squares 6, within the square 4 inscribed in the stop $P_{4-4}$ of the moving window 2 overlap or cover the nine computation voxels X22, X23, X24, X28, X29, X30, X34, X35 and X36, respectively, and each of the squares G136-G144 may have an area less than 10% of that of the stop $P_{4-4}$ of the moving window 2. For details about the squares G136-G144, please refer to the squares 6 illustrated in FIG. 3B.

After the measures of the specific MRI parameters for the sixteen stops $P_{1-1}$-$P_{4-4}$ of the moving window 2 are obtained, the step S5 is performed to obtain the probabilities PWs of the event for the respective stops $P_{1-1}$-$P_{4-4}$ of the moving window 2. The probabilities PWs of the event for the sixteen stops $P_{1-1}$, $P_{1-2}$, $P_{1-3}$, $P_{1-4}$, $P_{2-1}$, $P_{2-2}$, $P_{2-3}$, $P_{2-4}$, $P_{3-1}$, $P_{3-2}$, $P_{3-3}$, $P_{3-4}$, $P_{4-1}$, $P_{4-2}$, $P_{4-3}$, and $P_{4-4}$ of the moving window 2, for example, are 0.6055, 0.5628, 0.5366, 0.4361, 0.4982, 0.5534, 0.5521, 0.4227, 0.4618, 0.5132, 0.6214, 0.5810, 0.4371, 0.4698, 0.5774, and 0.5613, respectively. In the example, the sixteen probabilities PWs of the event for the sixteen stops $P_{1-1}$-$P_{4-4}$ of the moving window 2 are assumed to be those for the sixteen squares 4 inscribed in the respective stops $P_{1-1}$-$P_{4-4}$ of the moving window 2, respectively. In other words, the sixteen probabilities of the event for the sixteen squares 4 inscribed in the sixteen stops $P_{1-1}$-$P_{4-4}$ of the moving window 2 are 0.6055, 0.5628, 0.5366, 0.4361, 0.4982, 0.5534, 0.5521, 0.4227, 0.4618, 0.5132, 0.6214, 0.5810, 0.4371, 0.4698, 0.5774, and 0.5613, respectively.

Figure 17A:
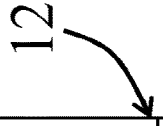
FIGS. 17A, 17B, and 17C show initial probabilities for computation voxels, updated probabilities for the computation voxels, and optimal probabilities for the computation voxels, respectively, in accordance with an embodiment of the present invention.

Next, the algorithm depicted in FIG. 8 is performed based on the probabilities PWs of the event for the sixteen stops $P_{1-1}$-$P_{4-4}$ of the moving window 2 to obtain or calculate optimal probabilities of the event for the computation voxels X1-X36, as described in the following specification. First of all, the probabilities PVs of the event for the computation voxels X1-X36 as shown in FIG. 17A are assumed by the step S11. In the step S11, referring to FIGS. 13A-13H, 14A-14H, 15A-15H, 16A-16H, and 17A, because the only stop $P_{1-1}$ of the moving window 2 has the square G1 overlapping the computation voxel X1, the probability PV of the event for the computation voxel X1 is assumed to be the probability PW, i.e., 0.6055, of the event for the stop $P_{1-1}$ of the moving window 2. Similarly, the probabilities PVs of the event for the computation voxels X6, X31 and X36 are assumed to be the probabilities PWs, i.e., 0.4361, 0.4371 and 0.5613, of the event for the stops $P_{1-4}$, $P_{4-1}$, and $P_{4-4}$ of the moving window 2, respectively.

Because the only two stops $P_{1-1}$ and $P_{1-2}$ of the moving window 2 have the squares G2 and G10 overlapping the computation voxel X2, the probability PV of the event for the computation voxel X2 is assumed to be the average, i.e., 0.5841, of the two probabilities PWs, i.e., 0.6055 and 0.5628, of the event for the stops $P_{1-1}$ and $P_{1-2}$ of the moving window 2. Similarly, the probability PV of the event for the computation voxel X5 is assumed to be the average, i.e., 0.4863, of the probabilities PWs, i.e., 0.5366 and 0.4361, of the event for the stops $P_{1-3}$ and $P_{1-4}$ of the moving window 2. The probability PV of the event for the computation voxel X7 is assumed to be the average, i.e., 0.5519, of the probabilities PWs, i.e., 0.6055 and 0.4982, of the event for the stops $P_{1-1}$ and $P_{2-1}$ of the moving window 2. The probability PV of the event for the computation voxel X12 is assumed to be the average, i.e., 0.4294, of the probabilities PWs, i.e., 0.4361 and 0.4227, of the event for the stops $P_{1-4}$ and $P_{2-4}$ of the moving window 2. The probability PV of the event for the computation voxel X25 is assumed to be the average, i.e., 0.4495, of the probabilities PWs, i.e., 0.4618 and 0.4371, of the event for the stops $P_{3-1}$ and $P_{4-1}$ of the moving window 2. The probability PV of the event for the computation voxel X30 is assumed to be the average, i.e., 0.5711, of the probabilities PWs, i.e., 0.5810 and 0.5613, of the event for the stops $P_{3-4}$ and $P_{4-4}$ of the moving window 2. The probability PV of the event for the computation voxel X32 is assumed to be the average, i.e., 0.4535, of the probabilities PWs, i.e., 0.4371 and 0.4698, of the event for the stops $P_{4-1}$ and $P_{4-2}$ of the moving window 2. The probability PV of the event for the computation voxel X35 is assumed to be the average, i.e., 0.5693, of the probabilities PWs, i.e., 0.5774 and 0.5613, of the event for the stops $P_{4-3}$ and $P_{4-4}$ of the moving window 2.

Because the only three stops $P_{1-1}$, $P_{1-2}$ and $P_{1-3}$ of the moving window 2 have the squares G3, G11 and G19 overlapping the computation voxel X3, the probability PV of the event for the computation voxel X3 is assumed to be the average, i.e., 0.5683, of the three probabilities PWs, i.e., 0.6055, 0.5628 and 0.5366, of the event for the stops $P_{1-1}$, $P_{1-2}$ and $P_{1-3}$ of the moving window 2. Similarly, the probability PV of the event for the computation voxel X4 is assumed to be the average, i.e., 0.5118, of the probabilities PWs of the event for the stops $P_{1-2}$, $P_{1-3}$ and $P_{1-4}$ of the moving window 2. The probability PV of the event for the computation voxel X13 is assumed to be the average, i.e., 0.5219, of the probabilities PWs of the event for the stops $P_{1-1}$, $P_{2-1}$ and $P_{3-1}$ of the moving window 2. The probability PV of the event for the computation voxel X18 is assumed to be the average, i.e., 0.4799, of the probabilities PWs of the event for the stops $P_{1-4}$, $P_{2-4}$ and $P_{3-4}$ of the moving window 2. The probability PV of the event for the computation voxel X19 is assumed to be the average, i.e., 0.4657, of the probabilities PWs of the event for the stops $P_{2-1}$, $P_{3-1}$ and $P_{4-1}$ of the moving window 2. The probability PV of the event for the computation voxel X24 is assumed to be the average, i.e., 0.5216, of the probabilities PWs of the event for the stops $P_{2-4}$, $P_{3-4}$ and $P_{4-4}$ of the moving window 2. The probability PV of the event for the computation voxel X33 is assumed to be the average, i.e., 0.4948, of the probabilities PWs of the event for the stops $P_{4-1}$, $P_{4-2}$ and $P_{4-3}$ of the moving window 2. The probability PV of the event for the computation voxel X34 is assumed to be the average, i.e., 0.5362, of the probabilities PWs of the event for the stops $P_{4-2}$, $P_{4-3}$ and $P_{4-4}$ of the moving window 2.

Because the only four stops $P_{1-1}$, $P_{1-2}$, $P_{2-1}$ and $P_{2-2}$ of the moving window 2 have the squares G5, G13, G38 and G46 overlapping the computation voxel X8, the probability PV of the event for the computation voxel X8 is assumed to be the average, i.e., 0.5550, of the four probabilities PWs, i.e., 0.6055, 0.5628, 0.4982 and 0.5534, of the event for the stops $P_{1-1}$, $P_{1-2}$, $P_{2-1}$ and $P_{2-2}$ of the moving window 2. Similarly, the probability PV of the event for the computation voxel X11 is assumed to be the average, i.e., 0.4869, of the probabilities PWs of the event for the stops $P_{1-3}$, $P_{1-4}$, $P_{2-3}$ and $P_{2-4}$ of the moving window 2. The probability PV of the event for the computation voxel X26 is assumed to be the average, i.e., 0.4705, of the probabilities PWs of the event for the stops $P_{3-1}$, $P_{3-2}$, $P_{4-1}$ and $P_{4-2}$ of the moving window 2. The probability PV of the event for the computation voxel X29 is assumed to be the average, i.e., 0.5852, of the probabilities PWs of the event for the stops $P_{3-3}$, $P_{3-4}$, $P_{4-3}$ and $P_{4-4}$ of the moving window 2.

Because the only six stops $P_{1-1}$, $P_{1-2}$, $P_{1-3}$, $P_{2-1}$, $P_{2-2}$ and $P_{2-3}$ of the moving window 2 have the squares G6, G14, G22, G39, G47 and G55 overlapping the computation voxel X9, the probability PV of the event for the computation voxel X9 is assumed to be the average, i.e., 0.5514, of the six probabilities PWs, i.e., 0.6055, 0.5628, 0.5366, 0.4982, 0.5534 and 0.5521, of the event for the stops $P_{1-1}$, $P_{1-2}$, $P_{1-3}$, $P_{2-1}$, $P_{2-2}$ and $P_{2-3}$ of the moving window 2. Similarly, the probability PV of the event for the computation voxel X10 is assumed to be the average, i.e., 0.5106, of the probabilities PWs of the event for the stops $P_{1-2}$, $P_{1-3}$, $P_{1-4}$, $P_{2-2}$, $P_{2-3}$ and $P_{2-4}$ of the moving window 2. The probability PV of the event for the computation voxel X14 is assumed to be the average, i.e., 0.5325, of the probabilities PWs of the event for the stops $P_{1-1}$, $P_{1-2}$, $P_{2-1}$, $P_{2-2}$, $P_{3-1}$ and $P_{3-2}$ of the moving window 2. The probability PV of the event for the computation voxel X17 is assumed to be the average, i.e., 0.5250, of the probabilities PWs of the event for the stops $P_{1-3}$, $P_{1-4}$, $P_{2-3}$, $P_{2-4}$, $P_{3-3}$ and $P_{3-4}$ of the moving window 2. The probability PV of the event for the computation voxel X20 is assumed to be the average, i.e., 0.4889, of the probabilities PWs of the event for the stops $P_{2-1}$, $P_{2-2}$, $P_{3-1}$, $P_{3-2}$, $P_{4-1}$ and $P_{4-2}$ of the moving window 2. The probability PV of the event for the computation voxel X23 is assumed to be the average, i.e., 0.5526, of the probabilities PWs of the event for the stops $P_{2-3}$, $P_{2-4}$, $P_{3-3}$, $P_{3-4}$, $P_{4-3}$ and $P_{4-4}$ of the moving window 2. The probability PV of the event for the computation voxel X27 is assumed to be the average, i.e., 0.5134, of the probabilities PWs of the event for the stops $P_{3-1}$, $P_{3-2}$, $P_{3-3}$, $P_{4-1}$, $P_{4-2}$ and $P_{4-3}$ of the moving window 2. The probability PV of the event for the computation voxel X28 is assumed to be the average, i.e., 0.5540, of the probabilities PWs of the event for the stops $P_{3-2}$, $P_{3-3}$, $P_{3-4}$, $P_{4-2}$, $P_{4-3}$ and $P_{4-4}$ of the moving window 2.

Because the only nine stops $P_{1-1}$, $P_{1-2}$, $P_{1-1}$, $P_{2-1}$, $P_{2-2}$, $P_{2-3}$, $P_{3-1}$, $P_{3-2}$ and $P_{3-3}$ of the moving window 2 have the squares G9, G17, G25, G42, G50, G58, G75, G83 and G91 overlapping the computation voxel X15, the probability PV of the event for the computation voxel X15 is assumed to be the average, i.e., 0.5450, of the nine probabilities PWs, i.e., 0.6055, 0.5628, 0.5366, 0.4982, 0.5534, 0.5521, 0.4618, 0.5132 and 0.6214, of the event for the stops $P_{1-1}$, $P_{1-2}$, $P_{1-3}$, $P_{2-1}$, $P_{2-2}$, $P_{2-3}$, $P_{3-1}$, $P_{3-2}$ and $P_{3-3}$ of the moving window 2. Similarly, the probability PV of the event for the computation voxel X16 is assumed to be the average, i.e., 0.5310, of the probabilities PWs of the event for the stops $P_{1-2}$, $P_{1-3}$, $P_{1-4}$, $P_{2-2}$, $P_{2-3}$, $P_{2-4}$, $P_{3-2}$, $P_{3-3}$ and $P_{3-4}$ of the moving window 2. The probability PV of the event for the computation voxel X21 is assumed to be the average, i.e., 0.5205, of the probabilities PWs of the event for the stops $P_{2-1}$, $P_{2-2}$, $P_{2-3}$, $P_{3-1}$, $P_{3-2}$, $P_{3-3}$, $P_{4-1}$, $P_{4-2}$ and $P_{4-3}$ of the moving window 2. The probability PV of the event for the computation voxel X22 is assumed to be the average, i.e., 0.5391, of the probabilities PWs of the event for the stops $P_{2-2}$, $P_{2-3}$, $P_{2-4}$, $P_{3-2}$, $P_{3-3}$, $P_{3-4}$, $P_{4-2}$, $P_{4-3}$ and $P_{4-4}$ of the moving window 2.

After the probabilities PVs of the event for the respective computation voxels X1-X36 are assumed, the step S12 is performed to obtain sixteen probability guesses PGs for the respective stops $P_{1-1}$, $P_{1-2}$, $P_{1-3}$, $P_{1-4}$, $P_{2-1}$, $P_{2-2}$, $P_{2-3}$, $P_{2-4}$, $P_{3-1}$, $P_{3-2}$, $P_{3-3}$, $P_{1-4}$, $P_{4-1}$, $P_{4-2}$, $P_{4-1}$, and $P_{4-4}$ of the moving window 2. The probability guess PG for each of the sixteen stops $P_{1-1}$-$P_{4-4}$ of the moving window 2 is calculated by averaging the nine probabilities PVs of the event for respective nine of the computation voxels X1-X36 overlapping or covering the respective nine small squares 6 within the square 4 inscribed in said each of the sixteen stops $P_{1-1}$-$P_{4-4}$ of the moving window 2. For example, because the nine small squares G1-G9 within the square 4 inscribed in the stop $P_{1-1}$ of the moving window 2 overlap or cover the respective computation voxels X1, X2, X3, X7, X8, X9, X13, X14 and X15, the probability guess PG for the stop $P_{1-1}$ of the moving window 2 is calculated by averaging the nine probabilities PVs, i.e., 0.6055, 0.5841, 0.5683, 0.5519, 0.5550, 0.5514, 0.5219, 0.5325 and 0.5450, of the event for the computation voxels X1, X2, X3, X7, X8, X9, X13, X14 and X15 inside the stop $P_{1-1}$ of the moving window 2. Accordingly, the probability guesses PGs for the stops $P_{1-1}$, $P_{1-2}$, $P_{1-3}$, $P_{1-4}$, $P_{2-1}$, $P_{2-2}$, $P_{2-3}$, $P_{2-4}$, $P_{3-1}$, $P_{3-2}$, $P_{3-3}$, $P_{3-4}$, $P_{4-1}$, $P_{4-2}$, $P_{4-3}$, and $P_{4-4}$ of the moving window 2 are 0.5573, 0.5433, 0.5240, 0.4886, 0.5259, 0.5305, 0.5291, 0.5085, 0.5009, 0.5217, 0.5407, 0.5400, 0.4771, 0.5079, 0.5406, and 0.5545, respectively.

After the sixteen probability guesses PGs are obtained or calculated, the step S13 is performed to obtain sixteen differences DWs for the sixteen stops $P_{1-1}$-$P_{4-4}$ of the moving window 2. Each of the sixteen differences DWs is calculated by, e.g., subtracting the probability PW of the event for a corresponding one of the sixteen stops $P_{1-1}$-$P_{4-4}$ of the moving window 2 from the probability guess PG for the corresponding one of the sixteen stops $P_{1-1}$-$P_{4-4}$ of the moving window 2. For example, the difference DW for the stop $P_{hi}$ of the moving window 2 is calculated by subtracting the probability PW, i.e., 0.6055, of the event for the stop $P_{1-1}$ of the moving window 2 from the probability guess PG, i.e., 0.5573, for the stop $P_{1-1}$ of the moving window 2. Accordingly, the differences DWs for the stops $P_{1-1}$, $P_{1-2}$, $P_{1-3}$, $P_{1-4}$, $P_{2-1}$, $P_{2-2}$, $P_{2-3}$, $P_{2-4}$, $P_{3-1}$, $P_{3-2}$, $P_{3-3}$, $P_{3-4}$, $P_{4-1}$, $P_{4-2}$, $P_{4-3}$, and $P_{4-4}$ of the moving window 2 are −0.0482, −0.0194, −0.0126, 0.0525, 0.0276, −0.0230, −0.0230, 0.0858, 0.0391, 0.0085, −0.0807, −0.0410, 0.0400, 0.0380, −0.0368, and −0.0068, respectively.

Figure 17B:
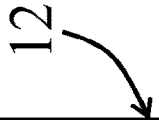

After the sixteen differences DWs are obtained or calculated, the step S14 is performed to determine whether absolute values of the sixteen differences DWs are less than or equal to a preset threshold value of 0.0001. Because the absolute values of the sixteen differences DWs are greater than the preset threshold value, the step S15 continues in which the probabilities PVs of the event for the computation voxels X1-X36 are updated, as shown in FIG. 17B.

In the step S15, the updated probability PV of the event for each of the computation voxels X1-X36 is calculated by, e.g., subtracting an error correction factor ECF for said each of the computation voxels X1-X36 from the probability PV of the event for said each of the computation voxels X1-X36. The error correction factor ECF for each of the 4 computation voxels X1, X6, X31 and X36 is obtained by, e.g., calculating an error correction contribution only from a corresponding one of the stops $P_{1-1}$, $P_{1-4}$, $P_{4-1}$ and $P_{4-4}$ of the moving window 2, which has one of its squares 6 covering or overlapping said each of the 4 computation voxels X1, X6, X31 and X36. For example, because the only stop $P_{1-1}$ of the moving window 2 has the small square G1 covering or overlapping the computation voxel X1, the error correction factor ECF, i.e., −0.0054, for the computation voxel X1 is obtained by calculating the error correction contribution only from the stop $P_{1-1}$ of the moving window 2. The error correction contribution to the computation voxel X1 from the stop $P_{1-1}$ of the moving window 2 is calculated by multiplying the difference DW, i.e., −0.0482, for the stop $P_{1-1}$ of the moving window 2 by an area ratio, i.e., 1/9, of an overlapped area between the computation voxel X1 and the stop $P_{1-1}$ of the moving window 2 to an area of the square 4 inscribed in the stop $P_{1-1}$ of the moving window 2. Accordingly, the updated probability PV of the event for the computation voxel X1 is calculated by subtracting the error correction factor ECF, i.e., −0.0054, for the computation voxel X1 from the probability PV, i.e., 0.6055, of the event for the computation voxel X1.

The error correction factor ECF for each of the 32 computation voxels X2-X5, X7-X30 and X32-X35 is calculated by, e.g., summing error correction contributions from overlapping ones of the stops $P_{1-1}$-$P_{4-4}$ of the moving window 2, each having one of its squares 6 covering or overlapping said each of the 32 computation voxels X2-X5, X7-X30 and X32-X35; each of the error correction contributions to said each of the 32 computation voxels X2-X5, X7-X30 and X32-X35 is calculated by multiplying the difference DW for a corresponding one of the overlapping ones of the stops $P_{1-1}$-$P_{44}$ of the moving window 2 by an area ratio of an overlapped area between said each of the 32 computation voxels X2-X5, X7-X30 and X32-X35 and the corresponding one of the overlapping ones of the stops $P_{1-1}$-$P_{4-4}$ of the moving window 2 to an area of the square 4 inscribed in the corresponding one of the overlapping ones of the stops $P_{1-1}$-$P_{4-4}$ of the moving window 2. For example, because the only nine stops $P_{1-1}$, $P_{1-2}$, $P_{1-3}$, $P_{2-1}$, $P_{2-2}$, $P_{2-3}$, $P_{3-1}$, $P_{3-2}$, and $P_{3-3}$ of the moving window 2 have the squares G9, G17, G25, G42, G50, G58, G75, G83 and G91 covering or overlapping the computation voxel X15, the error correction factor ECF, i.e., −0.0146, for the computation voxel X15 is obtained by summing error correction contributions from the respective stops $P_{1-1}$, $P_{1-2}$, $P_{1-3}$, $P_{2-1}$, $P_{2-2}$, $P_{2-3}$, $P_{3-1}$, $P_{3-2}$, and $P_{3-3}$ of the moving window 2. The error correction contribution, i.e., −0.0053, from the stop $P_{1-1}$ of the moving window 2 to the computation voxel X15 is calculated by multiplying the difference DW, i.e., −0.0482, for the stop $P_{1-1}$ of the moving window 2 by an area ratio, i.e., 1/9, of an overlapped area between the computation voxel X15 and the stop $P_{1-1}$ of the moving window 2 to the area of the square 4 inscribed in the stop $P_{1-1}$ of the moving window 2. The error correction contribution, i.e., −0.0021, from the stop $P_{1-2}$ of the moving window 2 to the computation voxel X15 is calculated by multiplying the difference DW, i.e., −0.0194, for the stop $P_{1-2}$ of the moving window 2 by an area ratio, i.e., 1/9, of an overlapped area between the computation voxel X15 and the stop $P_{1-2}$ of the moving window 2 to the area of the square 4 inscribed in the stop $P_{1-2}$ of the moving window 2. The error correction contribution, i.e., −0.0014, from the stop $P_{1-3}$ of the moving window 2 to the computation voxel X15 is calculated by multiplying the difference DW, i.e., −0.0126, for the stop $P_{1-3}$ of the moving window 2 by an area ratio, i.e., 1/9, of an overlapped area between the computation voxel X15 and the stop $P_{1-3}$ of the moving window 2 to the area of the square 4 inscribed in the stop $P_{1-3}$ of the moving window 2. The error correction contribution, i.e., 0.0031, from the stop $P_{2-1}$ of the moving window 2 to the computation voxel X15 is calculated by multiplying the difference DW, i.e., 0.0276, for the stop $P_{2-1}$ of the moving window 2 by an area ratio, i.e., 1/9, of an overlapped area between the computation voxel X15 and the stop $P_{2-1}$ of the moving window 2 to the area of the square 4 inscribed in the stop $P_{2-1}$ of the moving window 2. The error correction contribution, i.e., −0.0026, from the stop $P_{2-2}$ of the moving window 2 to the computation voxel X15 is calculated by multiplying the difference DW, i.e., −0.0230, for the stop $P_{2-2}$ of the moving window 2 by an area ratio, i.e., 1/9, of an overlapped area between the computation voxel X15 and the stop $P_{2-2}$ of the moving window 2 to the area of the square 4 inscribed in the stop $P_{2-2}$ of the moving window 2. The error correction contribution, i.e., −0.0026, from the stop $P_{2-3}$ of the moving window 2 to the computation voxel X15 is calculated by multiplying the difference DW, i.e., −0.0230, for the stop $P_{2-3}$ of the moving window 2 by an area ratio, i.e., 1/9, of an overlapped area between the computation voxel X15 and the stop $P_{2-3}$ of the moving window 2 to the area of the square 4 inscribed in the stop $P_{2-3}$ of the moving window 2. The error correction contribution, i.e., 0.0043, from the stop $P_{3-1}$ of the moving window 2 to the computation voxel X15 is calculated by multiplying the difference DW, i.e., 0.0391, for the stop $P_{3-1}$ of the moving window 2 by an area ratio, i.e., 1/9, of an overlapped area between the computation voxel X15 and the stop $P_{3-1}$ of the moving window 2 to the area of the square 4 inscribed in the stop $P_{3-1}$ of the moving window 2. The error correction contribution, i.e., 0.0009, from the stop $P_{3-2}$ of the moving window 2 to the computation voxel X15 is calculated by multiplying the difference DW, i.e., 0.0085, for the stop $P_{3-2}$ of the moving window 2 by an area ratio, i.e., 1/9, of an overlapped area between the computation voxel X15 and the stop $P_{3-2}$ of the moving window 2 to the area of the square 4 inscribed in the stop $P_{3-2}$ of the moving window 2. The error correction contribution, i.e., −0.0089, from the stop $P_{3-3}$ of the moving window 2 to the computation voxel X15 is calculated by multiplying the difference DW, i.e., −0.0807, for the stop $P_{3-3}$ of the moving window 2 by an area ratio, i.e., 1/9, of an overlapped area between the computation voxel X15 and the stop $P_{3-3}$ of the moving window 2 to the area of the square 4 inscribed in the stop $P_{3-3}$ of the moving window 2. Accordingly, the updated probability PV of the event for the computation voxel X15 is calculated by subtracting the error correction factor ECF, i.e., −0.0146, for the computation voxel X15 from the probability PV, i.e., 0.5450, of the event for the computation voxel X15.

Figure 17C:
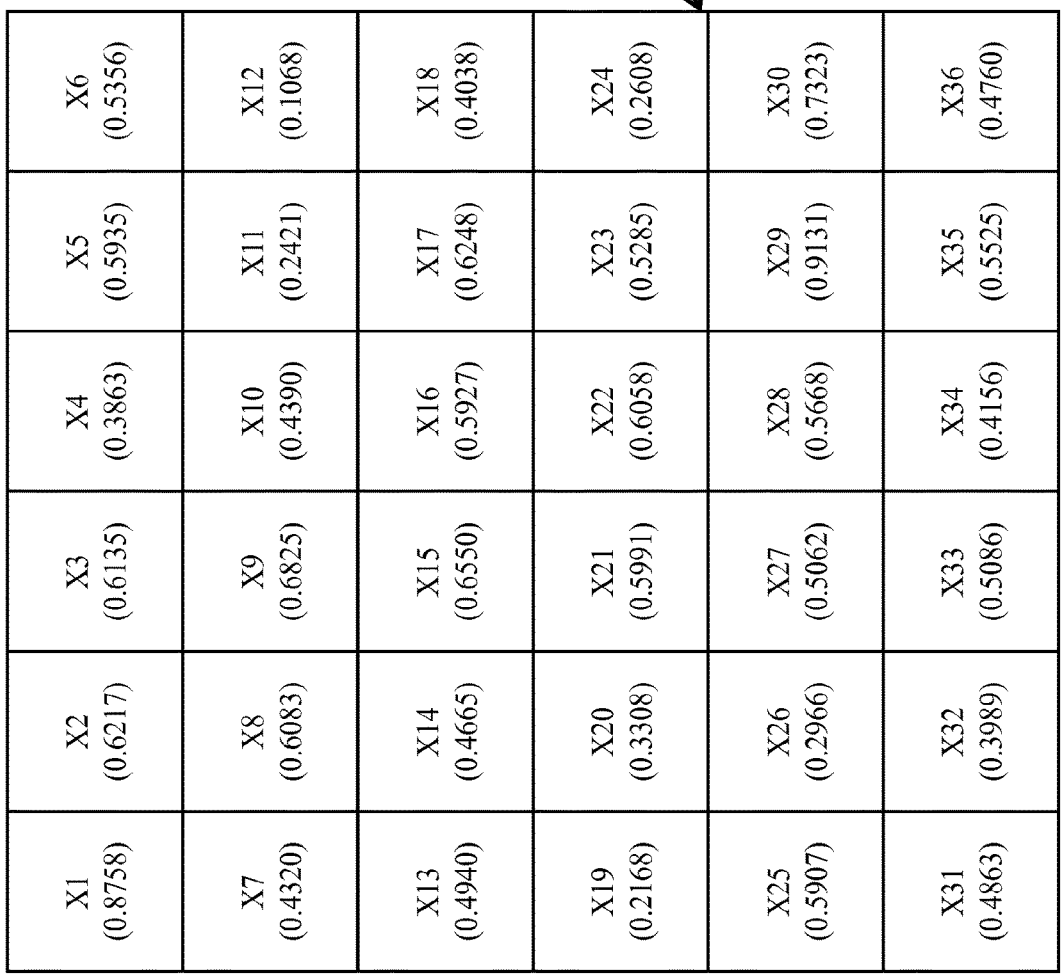

After the updated probabilities PVs of the event for the computation voxels X1-X36 are obtained or calculated, the steps S12-S15 are performed repeatedly based on the updated probabilities PVs of the event for the computation voxels X1-X36 in the step S15, until the absolute values of the sixteen differences DWs for the sixteen stops $P_{1-1}$-$P_{4-4}$ of the moving window 2 are less than or equal to the preset threshold value. Accordingly, the optimal probabilities of the event for the computation voxels X1-X36, as shown in FIG. 17C, are obtained and form the probability map for the event.

The above process, including the steps S1-S6, is performed to generate the moving window 2 across the computation regions 12 of the MRI slice 10 along the x and y directions to create a two-dimensional (2D) probability map. In order to obtain a three-dimensional (3D) probability map, the above process, including the steps S1-S6, may be applied to each of all MRI slices (including the MRI slice 10) of the subject arranged in the z direction perpendicular to the x and y directions.

The invention provides a computing method, i.e., the steps S1-S6, to obtain measures of the specific MRI parameters for multiple large regions or volumes of the MRI image 10 (i.e., the stops of the moving window 2), each including multiple voxels of the MRI image 10, and obtain a probability map having small regions (i.e., computation voxels) with extremely accurate probabilities based on the measures of the specific MRI parameters for the large regions or volumes, which overlaps, of the MRI image 10. Because of calculation for the probabilities based on the large regions or volumes of the MRI image 10, registered or aligned errors between the registered image sets (or registered parameter maps) can be compensated.

In the algorithm depicted in FIG. 8, some of the steps S11-S16, for example, may be performed on one or more MRI machines. In the computing method depicted in FIG. 4, the steps S1-S6, for example, may be performed on a MRI system, which may include one or more MRI machines to perform some or all of the steps S11-S16. A probability map for occurrence of prostate cancer, for example, may be formed by the MRI system to perform the steps S1-S6 and shows a probability of cancer for a small portion of the prostate.

Figure 18C:
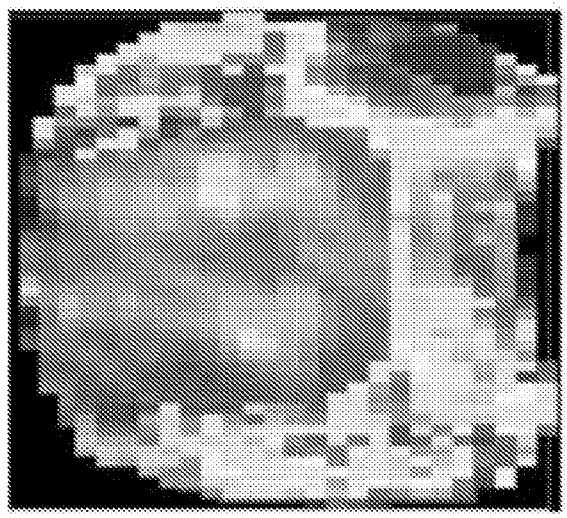
FIGS. 18A-18C show three probability maps.
Figure 18B:
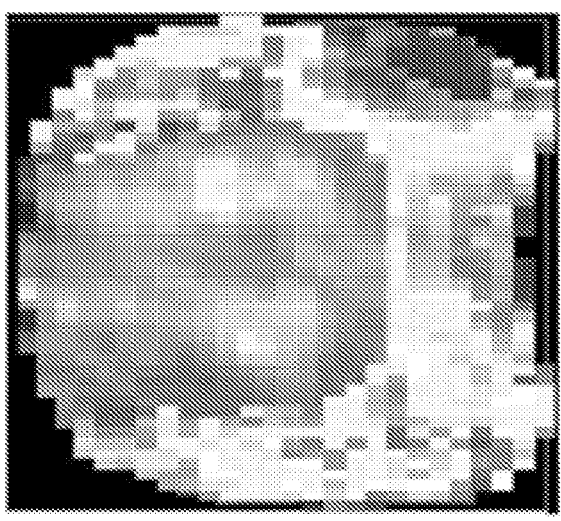
Figure 18A:
Figure 18D:
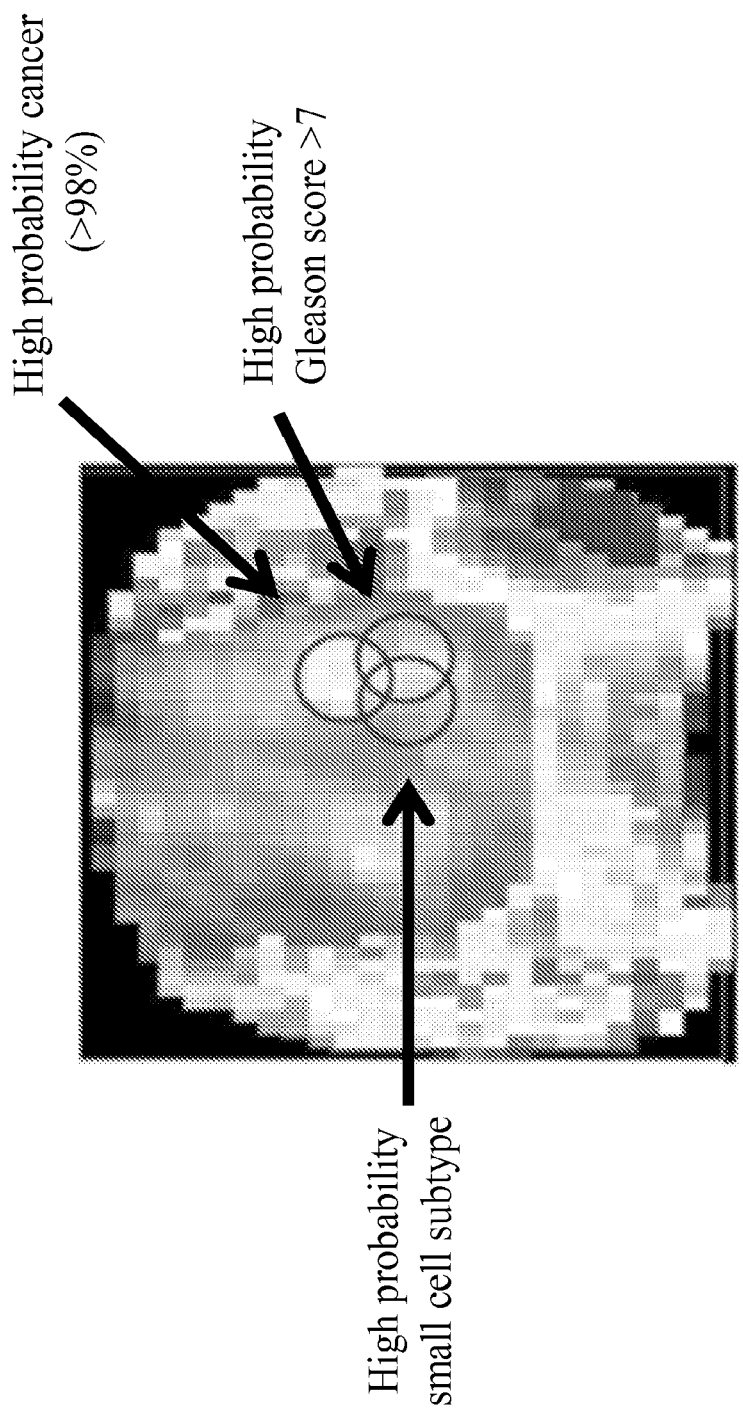
FIG. 18D shows a composite probability image or map.

By repeating the stops S1-S6 or the steps S5 and S6 for various events such as occurrence of prostate cancer, occurrence of small cell subtype, and occurrence of Gleason scores greater than 7, multiple probability maps for the various events are obtained or formed. The probability maps, for example, include a prostate cancer probability map shown in FIG. 18A, a small cell subtype probability map shown in FIG. 18B, and a probability map of Gleason scores greater than 7 shown in FIG. 18C. Some or all of the probability maps may be selected to be combined into a composite probability image or map to provide most useful information to interpreting Radiologist and Oncologist. The composite probability image or map may show areas of interest. For example, the composite probability image or map shows areas with high probability of cancer (>98%), high probability of small cell subtype, and high probability of Gleason score >7, as shown in FIG. 18D.

In an alternative embodiment, the subset data DB-1 may further include measures for a PET parameter (e.g., SUVmax) and a SPECT parameter. In this case, the classifier CF, e.g., Bayesian classifier, for the event (e.g., occurrence of prostate cancer) may be created based on data associated with the event and specific variables, including, e.g., the PET parameter, the SPECT parameter, some or all of the MRI parameters depicted in the section of the "description of classifier CF", and the processed parameters of average Ve and average Ktrans, in the subset data DB-1. Next, by using the computing method depicted in FIG. 4, the probability map for the event may be generated or formed based on measures of the specific variables for each stop of the moving window 2.

In the invention, the computing method (i.e., the steps S1-S6) depicted in FIG. 4, for example, may be performed on a software, a device, or a system including, e.g., hardware, one or more computing devices, computers, processors, software, and/or tools to obtain the above-mentioned probability map(s) for the event(s) and/or the above-mentioned composite probability image or map. Accordingly, a doctor questions the software, device or system about a suspected region of an image such as MRI slice image, and the latter provides a probability map for the event (e.g., occurrence of prostate cancer) and/or a likelihood measurement of cancer (e.g., malignancy) as an answer.

Second Embodiment

In the case of the MRI image 10 obtained from the subject (e.g., human patient) that has been given a treatment, such as neoadjuvant chemotherapy or (preoperative) radiation therapy, or has taken or been injected with one or more drugs for a treatment, such as neoadjuvant chemotherapy, the effect of the treatment or the drugs on the subject may be evaluated, identified, or determined by analyzing the probability map(s) for the event(s) depicted in the first embodiment and/or the composite probability image or map depicted in the first embodiment. Accordingly, a method of evaluating, identifying, or determining the effect of the treatment or the drugs on the subject may include the following steps: (a) administering to the subject the treatment or the drugs, (b) after the step (a), obtaining the MRI image 10 from the subject by the MRI system, (c) after the step (b), performing the steps S2-S6 to obtain the probability map(s) for the event(s) depicted in the first embodiment and/or obtaining the composite probability image or map depicted in the first embodiment, and (d) after the step (c), analyzing the probability map(s) for the event(s) and/or the composite probability image or map.

Third Embodiment

The steps S1-S6 may be employed to generate a probability map of breast cancer. In this case, in the steps S1 and S2, the MRI image 10 shows the breast anatomical structure of the subject as shown in FIG. 19, and the computation region 12, set in the desired or anticipated region 11 of the MRI image 10, is defined with the computation voxels and covers at least 10, 25, 50, 80, 90 or 95 percent of the FOV of the MRI image 10, which includes the breast anatomical structure. The steps S3 and S4 are then sequentially performed. Next, in the step S5, a probability of breast cancer for each stop of the moving window 2 may be obtained by matching the parameter set for said each stop of the moving window 2 from the step S4 (or the measures of some or all of the specific MRI parameters for said each stop of the moving window 2 from the step S3) to the classifier CF created for breast cancer. In the step S6, the algorithm including the steps S11-S16 illustrated in FIG. 8 is performed based on the probabilities of breast cancer for the stops of the moving window 2 to compute probabilities of breast cancer for the respective computation voxels, and the probabilities of breast cancer for the respective computation voxels form the probability map of breast cancer.

Fourth Embodiment

Figure 21:
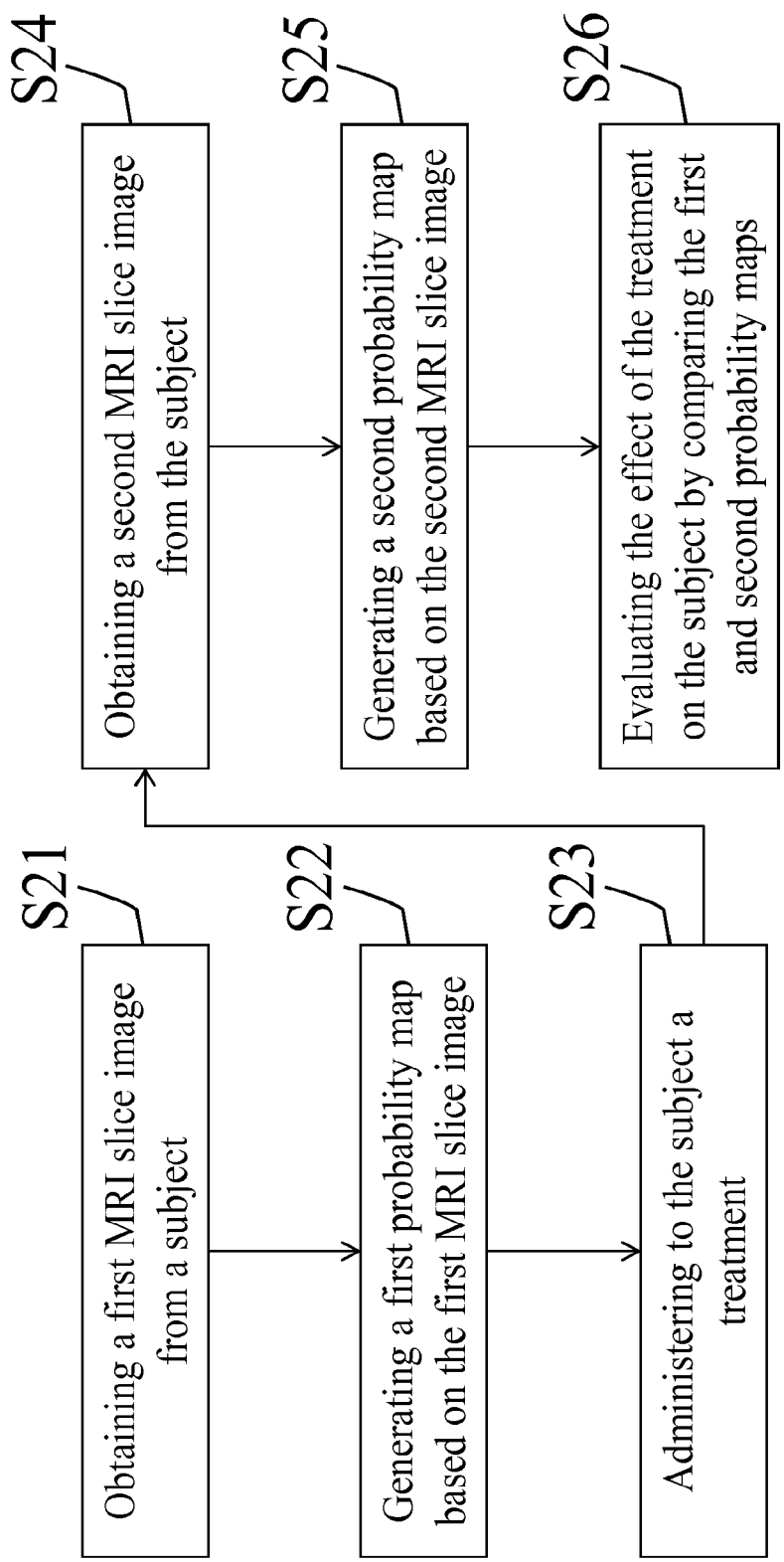
FIG. 21 is a flow chart depicting a method of evaluating, identifying, or determining the effect of a treatment (e.g., neoadjuvant chemotherapy or minimally invasive treatment of prostate cancer) or a drug used in the treatment on a subject in accordance with an embodiment of the present invention.

FIG. 21 is a flow chart of evaluating, identifying, or determining the effect of a treatment, such as neoadjuvant chemotherapy or (preoperative) radiation therapy, or a drug for the treatment on a subject (e.g., human or animal). Referring to FIG. 21, in a step S21, a first MRI slice image is obtained from the subject by the MRI device or system. The first MRI slice image is composed of multiple voxels in its field of view (FOV) to show an anatomical region of the subject, such as prostate or breast. In a step S22, the steps S2-S6 are performed on the first MRI slice image to generate a first probability map.

After the step S21 or S22 is performed, step S23 is performed. In the step S23, the subject is given the treatment, such as a drug given intravenously or orally. For certain cancers such as prostate cancer, the treatment may be the (preoperative) radiation therapy (or called radiotherapy), a proton beam therapy, a minimally invasive treatment (such as ablation or radiation), or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S24, after the subject gets or receives the treatment such as an oral or intravenous drug, a second MRI slice image is obtained from the subject by the MRI device or system. The second MRI slice image is composed of multiple voxels in its FOV to show the same anatomical region of the subject as the first MRI slice image shows. In a step S25, the steps S2-S6 are performed on the second MRI slice image to generate a second probability map. The first and second probability maps may be generated for an event or data type, such as prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent). Next, in a step S26, by comparing the first and second probability maps, the effect of the treatment or the drug used in the treatment on the subject may be identified, determined, or evaluated as effective or ineffective. Based on the result from the step S26, a doctor can decide or judge whether the treatment or the drug should be adjusted or changed. The method depicted in the steps S21-S26 can detect responses or progression after the treatment or the drug within less than one week or two weeks, allowing earlier adjustments to the treatment regime.

Fifth Embodiment

Figure 22:
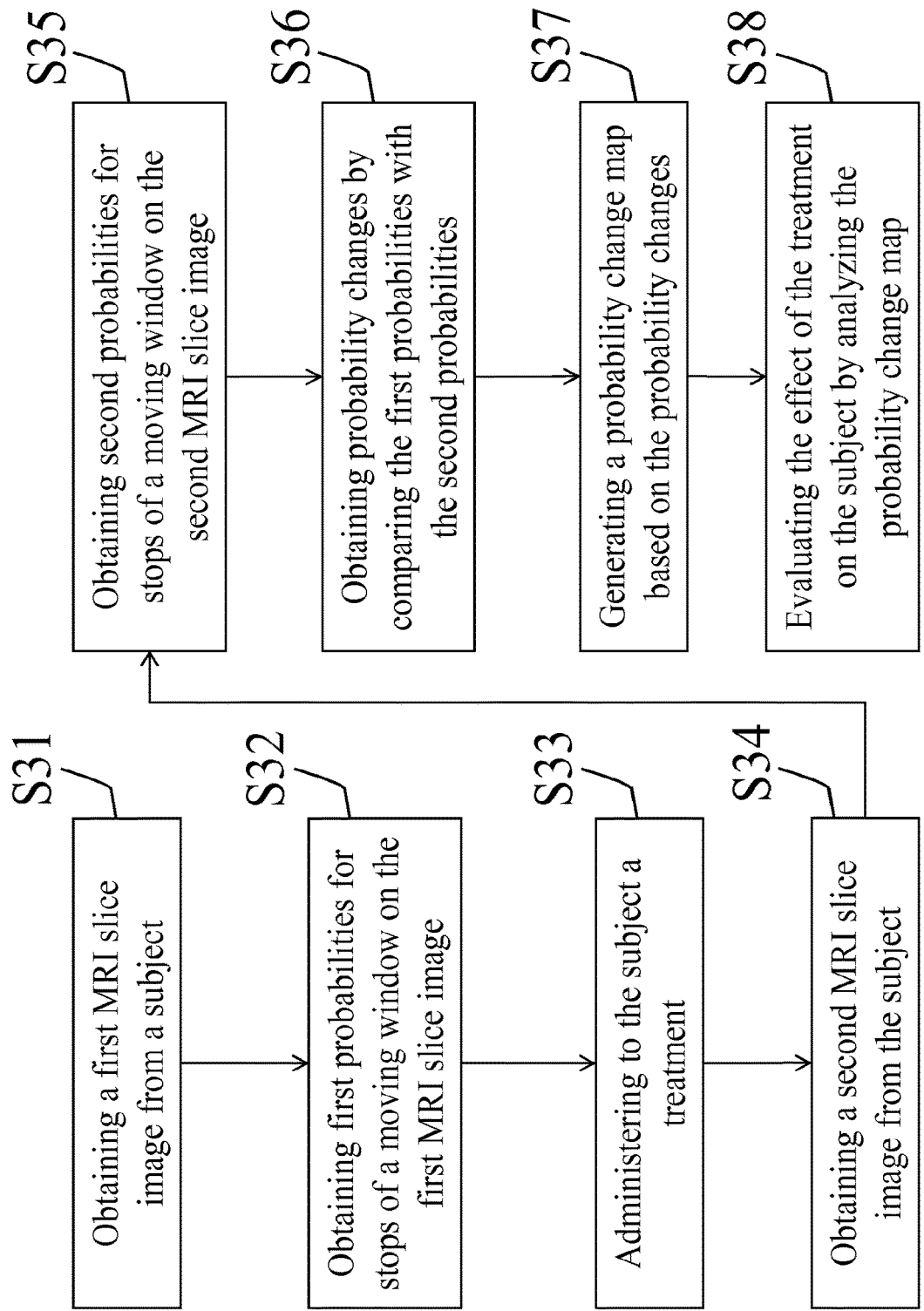
FIG. 22 is a flow chart depicting a method of evaluating, identifying, or determining the effect of a treatment or a drug used in the treatment on a subject in accordance with an embodiment of the present invention.

FIG. 22 is a flow chart of evaluating, identifying, or determining the effect of a treatment, such as neoadjuvant chemotherapy or (preoperative) radiation therapy, or a drug for the treatment on a subject (e.g., human or animal). Referring to FIG. 22, in a step S31, a first MRI slice image is obtained from the subject by the MRI device or system. The first MRI slice image is composed of multiple voxels in its field of view (FOV) to show an anatomical region of the subject, such as prostate or breast. In a step S32, the steps S2-S5 are performed on the first MRI slice image to obtain first probabilities of an event or data type for stops of the moving window 2 for the computation region 12 of the first MRI slice image. In other words, the first probabilities of the event or data type for the stops of the moving window 2 on the first MRI slice image for the subject before the treatment are obtained based on measures of the specific MRI parameters for the stops of the moving window 2 on the first MRI slice image to match a matching dataset from the established classifier CF or biomarker library. The measures of the specific MRI parameters for the stops of the moving window 2 on the first MRI slice image, for example, may be obtained from a registered (multi-parametric) image dataset including, e.g., the first MRI slice image and/or different parameter maps registered to the first MRI slice. The event or data type, for example, may be prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

After the step S31 or S32 is performed, step S33 is performed. In the step S33, the subject is given the treatment, such as a drug given intravenously or orally. For certain cancers such as prostate cancer, the treatment may be the (preoperative) radiation therapy (or called radiotherapy), a proton beam therapy, a minimally invasive treatment (such as ablation or radiation), or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S34, after the subject gets or receives the treatment such as an oral or intravenous drug, a second MRI slice image is obtained from the subject by the MRI device or system. The second MRI slice image is composed of multiple voxels in its FOV to show the same anatomical region of the subject as the first MRI slice image shows. In a step S35, the steps S2-S5 are performed on the second MRI slice image to obtain second probabilities of the event or data type for stops of the moving window 2 for the computation region 12 of the second MRI slice image. In other words, the second probabilities of the event or data type for the stops of the moving window 2 on the second MRI slice image for the subject after the treatment are obtained based on measures of the specific MRI parameters for the stops of the moving window 2 on the second MRI slice image to match the matching dataset from the established classifier CF or biomarker library. The measures of the specific MRI parameters for the stops of the moving window 2 on the second MRI slice image, for example, may be obtained from a registered (multi-parametric) image dataset including, e.g., the second MRI slice image and/or different parameter maps registered to the second MRI slice.

The stops of the moving window 2 for the computation region 12 of the first MRI slice may substantially correspond to or may be substantially aligned with or registered to the stops of the moving window 2 for the computation region 12 of the second MRI slice, respectively. Each of the stops of the moving window 2 for the computation region 12 of the first MRI slice and the registered or aligned one of the stops of the moving window 2 for the computation region 12 of the second MRI slice may substantially cover the same anatomical region of the subject.

Next, in a step S36, the first and second probabilities of the event or data type for each aligned or registered pair of the stops of the moving window 2 on the first and second MRI slice images are subtracted from each other into a corresponding probability change PMC for said each aligned or registered pair of the stops of the moving window 2 on the first and second MRI slice images. For example, for each aligned or registered pair of the stops of the moving window 2 on the first and second MRI slice images, the probability change PMC may be obtained by subtracting the first probability of the event or data type from the second probability of the event or data type.

In a step S37, the algorithm, including the steps S11-S16, depicted in the step S6 is performed based on the probability changes PMCs for the aligned or registered pairs of the stops of the moving window 2 on the first and second MRI slice images to compute probability changes PVCs for respective computation voxels used to compose a probability change map for the event or data type, as described below. Referring to FIG. 8, in the step S11, the probability change PVC for each of the computation voxels is assumed by, e.g., averaging the probability changes PMCs of the aligned or registered pairs, of the stops of the moving window 2 on the first and second MRI slice images, each having their aligned or registered squares 6 overlapping or covering said each of the computation voxels. In the step S12, a probability guess PG for each aligned or registered pair of the stops of the moving window 2 on the first and second MRI slice images is calculated by, e.g., averaging the probability changes PVCs for all the computation voxels inside said each aligned or registered pair of the stops of the moving window 2 on the first and second MRI slice images.

In the step S13, a difference DW between the probability guess PG and the probability change PMC for each aligned or registered pair of the stops of the moving window 2 on the first and second MRI slice images is calculated by, e.g., subtracting the probability change PMC for said each aligned or registered pair of the stops of the moving window 2 on the first and second MRI slice images from the probability guess PG for said each aligned or registered pair of the stops of the moving window 2 on the first and second MRI slice images. In the step S14, an absolute value of the difference DW for each aligned or registered pair of the stops of the moving window 2 on the first and second MRI slice images is compared with the preset threshold error or value to determine whether an error, i.e., the absolute value of the difference DW, between the probability guess PG and the probability change PMC for each aligned or registered pair of the stops of the moving window 2 on the first and second MRI slice images is less than or equal to the preset threshold error or value. If the absolute values of the differences DWs for all the aligned or registered pairs of the stops of the moving window 2 on the first and second MRI slice images are determined in the step S14 to be less than or equal to the preset threshold error or value, the step S16 continues. In the step S16, the probability changes PVCs for the computation voxels are determined to be optimal, which are called optimal probability changes hereinafter, and the optimal probability changes of the computation voxels form the probability change map for the event or data type. After the optimal probability changes for the computation voxels are obtained in the step S16, the algorithm is completed.

If any one of the absolute values of the differences DWs for all the aligned or registered pairs of the stops of the moving window 2 on the first and second MRI slice images is determined in the step S14 to be greater than the preset threshold error or value, the step S15 continues. In the step S15, the probability change PVC for each of the computation voxels is updated or adjusted by, e.g., subtracting an error correction factor ECF for said each of the computation voxels from the probability change PVC for said each of the computation voxels. The error correction factor ECF for each of the computation voxels is calculated by, e.g., summing error correction contributions from the aligned or registered pairs, of the stops of the moving window 2 on the first and second MRI slice images, each having their aligned or registered squares 6 covering or overlapping said each of the computation voxels; each of the error correction contributions to said each of the computation voxels, for example, may be calculated by multiplying the difference DW for a corresponding one of the aligned or registered pairs of the stops of the moving window 2 on the first and second MRI slice images by an area ratio of an overlapped area between said each of the computation voxels and the corresponding one of the aligned or registered pairs of the stops of the moving window 2 on the first and second MRI slice images to a common area of the squares 4 inscribed in the corresponding one of the aligned or registered pairs of the stops of the moving window 2 on the first and second MRI slice images. After the probability changes PVCs for the computation voxels are updated, the steps S12-S15 are performed repeatedly based on the updated probability changes PVCs for the computation voxels in the step S15, until the absolute values of the differences DWs for all the aligned or registered pairs of the stops of the moving window 2 on the first and second MRI slice images are determined in the step S14 to be less than or equal to the preset threshold error or value.

The above process uses the moving window 2 in the x and y directions to create a 2D probability change map. In addition, the above process may be applied to multiple MRI slices of the subject registered in the z direction, perpendicular to the x and y directions, to form a 3D probability change map.

In a step S38, by analyzing the probability change map, the effect of the treatment or the drug used in the treatment on the subject may be identified, determined, or evaluated as effective or ineffective. Based on the result from the step S38, a doctor can decide or judge whether the treatment or the drug should be adjusted or changed. The method depicted in the steps S31-S38 can detect responses or progression after the treatment or the drugs within less than one week or two weeks, allowing earlier adjustments to the treatment regime.

Sixth Embodiment

Figure 23:
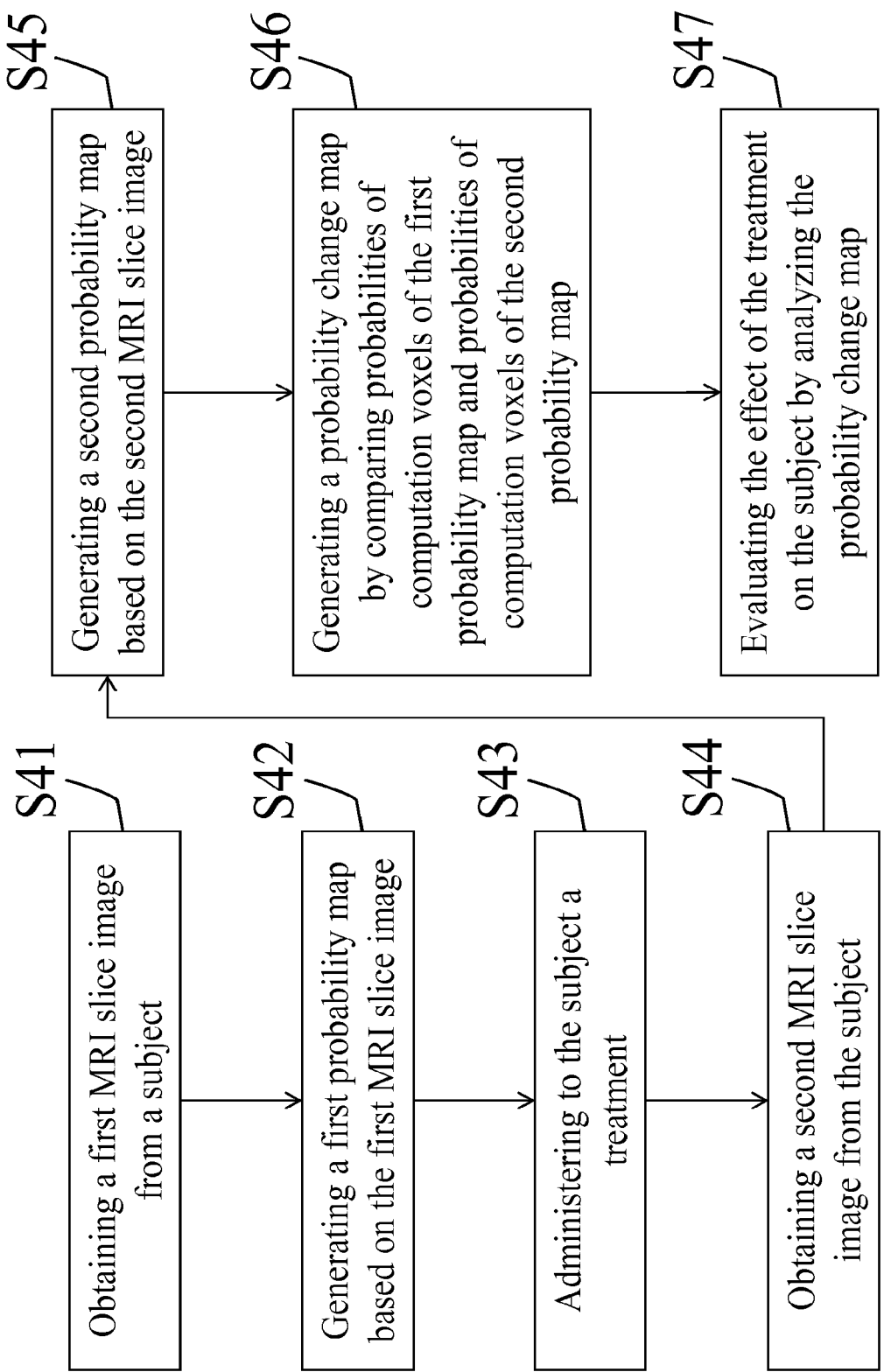
FIG. 23 is a flow chart depicting a method of evaluating, identifying, or determining the effect of a treatment or a drug used in the treatment on a subject in accordance with an embodiment of the present invention.

FIG. 23 is a flow chart of evaluating, identifying, or determining the effect of a treatment, such as neoadjuvant chemotherapy or (preoperative) radiation therapy, or a drug used in the treatment on a subject (e.g., human or animal). Referring to FIG. 23, in a step S41, a first MRI slice image is obtained from the subject by the MRI device or system. The first MRI slice image is composed of multiple voxels in its field of view (FOV) to show an anatomical region of the subject, such as prostate or breast. In a step S42, the steps S2-S6 are performed on the first MRI slice image to generate a first probability map composed of first computation voxels.

After the step S41 or S42 is performed, step S43 is performed. In the step S43, the subject is given a treatment such as an oral or intravenous drug. For certain cancers such as prostate cancer, the treatment may be the (preoperative) radiation therapy (or called radiotherapy), a proton beam therapy, or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S44, after the subject gets or receives the treatment such as an oral or intravenous drug, a second MRI slice image is obtained from the subject by the MRI device or system. The second MRI slice image is composed of multiple voxels in its FOV to show the same anatomical region of the subject as the first MRI slice image shows. In a step S45, the steps S2-S6 are performed on the second MRI slice image to generate a second probability map composed of second computation voxels. Each of the second computation voxels may substantially correspond to or may be substantially aligned with or registered to one of the first computation voxels. The first and second probability maps may be generated for an event or data type such as prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

In a step S46, by subtracting a probability for each of the first computation voxels from a probability for the corresponding, registered or aligned one of the second computation voxels, a corresponding probability change is obtained or calculated. Accordingly, a probability change map is formed or generated based on the probability changes. Next, in a step S47, by analyzing the probability change map, the effect of the treatment or the drug used in the treatment on the subject may be identified, determined, or evaluated as effective or ineffective. Based on the result from the step S47, a doctor can decide or judge whether the treatment or the drug should be adjusted or changed. The method depicted in the steps S41-S47 can detect responses or progression after the treatment or the drug within less than one week or two weeks, allowing earlier adjustments to the treatment regime.

The steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different steps, features, benefits and advantages. These also include embodiments in which the steps are arranged and/or ordered differently.

What is claimed is:

1. A method for assessing a medical image, the method comprising:
   determining, by an image processing system, a computation region associated with the medical image, wherein the computation region comprises a plurality of voxels;
   generating, by the image processing system, a moving window;
   moving, by the image processing system, the moving window across the computation region in incremental steps to obtain measures of imaging parameters at each stop of the moving window, wherein two neighboring ones of said stops of said moving window are partially overlapped with each other, and wherein the moving window overlaps at least a portion of multiple voxels of the computation region at each stop of the moving window;
   weighting, by the image processing system, the measures corresponding to respective associated voxels of the computation region based on an amount of overlap between the moving window and the respective associated voxel at each respective stop;
   determining, by the image processing system, first probabilities of a biomarker for said stops of said moving window by matching said measures of said imaging parameters to a classifier; and
   determining, by the image processing system, a probability of an event corresponding to particular voxels of the computation region based on the first probabilities of the biomarker.

2. The method of claim 1, wherein said imaging parameters comprise at least four types of magnetic resonance imaging (MRI) parameters.

3. The method of claim 1, wherein two neighboring ones of said stops of said moving window are shifted from each other by a distance substantially equal to a side length of one of said voxels.

4. The method of claim 1, wherein said event is the presence of a cancer.

5. The method of claim 1, further comprising obtaining second probabilities of the event for multiple voxels based on information associated with the first probabilities, wherein said obtaining said second probabilities of said event comprises:
   calculating multiple assumed probabilities for said respective voxels of a probability map based on said first probabilities of said event for said stops of said moving window covering said respective voxels;
   calculating multiple probability guesses for said respective stops of said moving window based on said assumed probabilities for said voxels of said probability map within said respective stops of said moving window;
   calculating multiple differences each between one of said probability guesses and one of said first probabilities for one of said stops of said moving window; and
   updating said assumed probabilities for said respective voxels of said probability map based on said differences for said stops of said moving window covering said respective voxels of said probability map.

6. An image processing system comprising:
   a processing device configured to:
      determine a computation region associated with an image, wherein the computation region comprises a plurality of voxels;
      generate a moving window;
      move the moving window across the computation region in incremental steps to obtain measures of imaging parameters at each stop of the moving window, wherein two neighboring ones of said stops of said moving window are partially overlapped with each other, and wherein the moving window overlaps at least a portion of multiple voxels of the computation region at each stop of the moving window;
      weight the measures corresponding to respective associated voxels of the computation region based on an amount of overlap between the moving window and the respective associated voxel at each respective stop;
      determine first probabilities of a biomarker for said stops of said moving window by matching said measures of said imaging parameters to a classifier; and
      determine a probability of an event corresponding to particular voxels of the computation region based on the first probabilities of the biomarker.

7. The imaging system of claim 6, wherein said image comprises a magnetic resonance imaging (MRI) image.

8. The imaging system of claim 6, wherein said imaging parameters comprise at least four types of magnetic resonance imaging (MRI) parameters.

9. The imaging system of claim 6, wherein the processing device is further configured to generate a probability map based on the first probabilities of the biomarker, wherein said first stop said moving window is shifted from a next stop by a distance substantially equal to a side length of a voxel of said probability map.

10. The imaging system of claim 6, wherein said moving window has a size defined based on volumes of multiple biopsy tissues.

11. The imaging system of claim 6, wherein said moving window has a volume defined based on a volume of a biopsy tissue.

12. The imaging system of claim 6, wherein said moving window has a circular shape with a radius defined based on information associated with volumes of multiple biopsy tissues.

13. The imaging system of claim 6, wherein said first classifier comprises a Bayesian classifier.

14. The imaging system of claim 6, wherein said first classifier is created based on information associated with multiple third measures of said imaging parameters for multiple biopsy tissues and multiple diagnoses for said biopsy tissues.

15. The imaging system of claim 9, wherein the processing device is further configured to obtain second measures of the imaging parameters for a second stop of the moving window and calculate a third probability of said first event for a voxel of said probability map based on said first and second probabilities of said first event, wherein said first and second stops of said moving window overlap said voxel of said probability map.

16. The imaging system of claim 9, wherein the processing device is further configured to obtain second measures of the imaging parameters for a second stop of the moving window and calculate a third probability of said first event for one of multiple voxels of said probability map, wherein said calculating said third probability of said first event comprises:

assuming said third probability of said first event by averaging said first and second probabilities;

calculating a first probability guess for said first stop of said moving window by averaging a first group of probabilities of said first event for a first group of said voxels inside said first stop of said moving window, wherein said first group of probabilities of said first event comprise said third probability of said first event;

calculating a second probability guess for said second stop of said moving window by averaging a second group of probabilities of said first event for a second group of said voxels inside said second stop of said moving window, wherein said second group of probabilities of said first event comprise said third probability of said first event; and determining whether a first absolute value of a first difference between said first probability guess and said first probability of said first event and a second absolute value of a second difference between said second probability guess and said second probability of said first event are less than or equal to a preset threshold value.

17. The imaging system of claim 16, wherein said calculating said third probability of said first event further comprises updating said third probability of said first event based on information associated with said first and second differences.

18. The imaging system of claim 15, wherein the processing device is further configured to:

obtain a third probability of a second event for said first stop of said moving window by matching said first measures to a second classifier;

obtain a fourth probability of said second event for said second stop of said moving window by matching said second measures to said second classifier;

calculate a fifth probability of said first event based on said first and second probabilities of said first event;

calculate a sixth probability of said second event based on said third and fourth probabilities of said second event; and create a composite probability map based on information associated with said fifth probability of said first event and said sixth probability of said second event.

19. The method of claim 1, wherein generating the moving window comprises determining a shape of the moving window.

20. The method of claim 19, wherein the shape comprises a circle.

* * * * *